United States Patent
Melikian et al.

(10) Patent No.: US 7,417,062 B2
(45) Date of Patent: Aug. 26, 2008

(54) SUBSTITUTED ARYLAMIDES

(75) Inventors: Anita Melikian, San Francisco, CA (US); John J. Kim Wright, Redwood City, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 305 days.

(21) Appl. No.: 11/202,961

(22) Filed: Aug. 11, 2005

(65) Prior Publication Data
US 2006/0074071 A1  Apr. 6, 2006

Related U.S. Application Data

(60) Provisional application No. 60/614,563, filed on Sep. 29, 2004.

(51) Int. Cl.
| C07D 417/02 | (2006.01) |
| A61K 31/541 | (2006.01) |
| A61K 31/5377 | (2006.01) |
| A61K 31/496 | (2006.01) |

(52) U.S. Cl. .................. 514/414; 514/422; 514/428; 514/248; 514/249; 514/266.1; 514/300; 514/307; 514/314; 548/455; 548/517; 548/518; 548/525; 548/527; 548/567; 546/122; 546/148; 546/176; 544/235; 544/283; 544/353

(58) Field of Classification Search .............. 548/455, 548/517, 518, 525, 527, 567; 514/414, 422, 514/428, 248, 249, 266.1, 300, 307, 314; 546/122, 148, 176; 544/235, 283, 353
See application file for complete search history.

(56) References Cited

U.S. PATENT DOCUMENTS

2004/0102431 A1   5/2004  Boss et al.

FOREIGN PATENT DOCUMENTS

| WO | WO 03/055876 A1 | 7/2003 |
| WO | WO 2004/058705 A2 | 7/2004 |
| WO | WO 2005/074645 A2 | 8/2005 |
| WO | WO 2005/087236 A1 | 9/2005 |
| WO | WO 2004/096771 A1 | 11/2005 |

OTHER PUBLICATIONS

Ruchelman et al. Bioorganic & Medicinal Chemistry 12 (2004) 795-806.*

* cited by examiner

*Primary Examiner*—Kahsay T Habte
(74) *Attorney, Agent, or Firm*—Townsend and Townsend and Crew LLP

(57) ABSTRACT

Substituted benzamide compounds are provided along with methods for the use of those compounds for treating cancer.

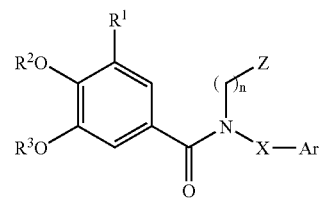

15 Claims, No Drawings

SUBSTITUTED ARYLAMIDES

CROSS-REFERENCES TO RELATED APPLICATIONS

This application claims the benefit of U.S. Provisional Application Ser. No. 60/614,563, filed Sep. 29, 2004, the content of which is incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE OR A COMPUTER PROGRAM LISTING APPENDIX SUBMITTED ON A COMPACT DISK

Attached below.

BACKGROUND OF THE INVENTION

The present invention is directed to novel compounds and pharmaceutical compositions that inhibit the binding of the SDF-1 chemokine (also known as the CXCL12 chemokine) or I-TAC (also known as CXCL11) to the chemokine receptor CCXCKR2. These compounds are useful in preventing tumor cell proliferation, tumor formation, and metastasis.

Chemokines are a superfamily of small, cytokine-like proteins that induce cytoskeletal rearrangement, firm adhesion to endothelial cells, and directional migration and may also effect cell activation and proliferation. Chemokines act in a coordinated fashion with cell surface proteins to direct the specific homing of various subsets of cells to specific anatomical sites.

Early research efforts by a number of groups have indicated a role for the chemokine receptor CXCR4 in metastasis and tumor growth. Muller, et al., "Involvement of Chemokine Receptors in Breast Cancer Metastasis," Nature, 410:50-56 (2001) demonstrated that breast tumor cells use chemokine-mediated mechanisms, such as those regulating leukocyte trafficking, during the process of metastasis. Tumor cells express a distinct, non-random pattern of functionally active chemokine receptors. Signaling through CXCR4 mediates actin polymerization and pseudopodia formation in breast cancer cells, and induces chemotactic and invasive responses. Additionally, the organs representing the main sites of breast cancer metastasis (such as lymph nodes, bone marrow, and lungs) are the most abundant sources of ligand for the CXCR4 receptor.

Using immunodeficient mice, Muller and colleagues succeeded in reducing the metastasis of injected human breast cancer cells by treating mice with an antibody known to bind CXCR4. Their finding suggests that breast cancer metastasis could be reduced by treating a patient with a CXCR4 antagonist.

Bertolini, et al., "CXCR4 Neutralization, a Novel Therapeutic Approach for Non-Hodgkin's Lymphoma," Cancer Research, 62:3106-3112 (2002) demonstrated a reduction of tumor volume as well as prolonged survival of immunodeficient mice injected with human lymphoma cells treated with anti-CXCR4 antibodies. They interpreted their finding to mean that tumor volume could be reduced by treating a patient with a CXCR4 antagonist.

More recent studies suggest that another chemokine receptor, CCXCKR2, may also be a potential candidate in the treatment of cancer. CCXCKR2 is preferentially expressed in transformed cells over normal cells, with detectable expression in a number of human cancers. In vitro studies indicate that proliferation of CCXCKR2 expressing cells can be inhibited by an antagonist of CCXCKR2. In vivo studies in mice indicate that CCXCKR2 antagonists can inhibit tumor formation and tumor growth.

The potential importance of CCXCKR2 is illustrated by an alternative interpretation of the reduction in tumor volume seen by Bertolini and colleagues. This reduction could clearly be the result of an antibody-mediated clearance, and not the result of the anti-CXCR4 antibody as originally believed. In an antibody-mediated clearance, any antibody that recognized a protein on the cell surface of the lymphoma cells would have had the same effect as that attributed to the anti-CXCR4 antibody. Unfortunately, Bertolini and colleagues studies are inconclusive as to whether the observed tumor response was due to antibody-mediated clearance or interaction with CXCR4.

However it is now known that the lymphoma cells used by Bertolini and colleagues express both CXCR4 and CCX-CKR2. SDF-1 is the only ligand for CXCR4. SDF-1 and I-TAC both bind CCXCKR2. Using anti-SDF-1 antibody, it has now been shown that antagonists of CCXCKR2 are responsible for the reduction in tumor load and increased survival rate. Because SDF-1 is the only ligand for CXCR4, one would expect neutralization of SDF-1 with anti-SDF-1 antibody would be equivalent to the neutralization of CXCR4 with anti-CXCR4 antibody. However, experiments using an anti-SDF-1 antibody demonstrated only a partial reduction in tumor load and an increased survival rate. As a result, CCX-CKR2 is the likely target, as the continued activity appears due to the interactions of the second ligand, I-TAC, with CCXCKR2.

Until recently, the possible importance of CCXCKR2 in tumor cell proliferation, tumor growth, and metastasis was unknown. Now, with recent evidence pointing to the ability of certain CCXCKR2 antagonists to prevent the growth and spread of cancer, and expression patterns indicating a limited tissue distribution for the CCXCKR2 receptor, it would be beneficial to provide compounds that are able to bind specifically to the CCXCKR2 receptor on tumor cells with potentially few side effects. Surprisingly, the present invention provides such compounds along with pharmaceutical compositions and related methods for treatment.

BRIEF SUMMARY OF THE INVENTION

The present invention provides, in one aspect, compounds having the formula:

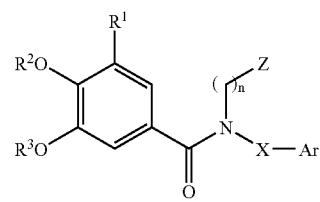

and all pharmaceutically acceptable salts thereof, wherein the subscript n is an integer of from 1 to 3; the symbol $R^1$ represents a hydrogen, halogen, $C_{1-8}$ alkoxy, $C_{1-8}$ alkyl, $C_{1-8}$ haloalkyl, $C_{3-6}$ cycloalkyl, $C_{3-6}$ cycloalkoxy, $C_{3-6}$ cycloalkyl $C_{1-4}$ alkyl or $C_{3-6}$ cycloalkyl $C_{1-4}$ alkoxy; the symbols $R^2$ and $R^3$ are each members independently selected from $C_{1-8}$ alkyl and $C_{1-8}$ haloalkyl, or are optionally combined with the oxygen atoms to which each is attached to from a five- to ten-membered ring optionally substituted with from one to four substituents selected from the group consisting of $C_{1-4}$ alkyl and $C_{1-4}$ haloalkyl; the letter X represents a bond, $CH_2$ or —$CH(CH_3)$—; the symbol Ar represents a linked- or fused-bicyclic aromatic ring system; and the letter Z represents a four-, five-, six- or seven-membered saturated nitrogen heterocyclic ring that is optionally substituted with from one to four $R^4$ substituents independently selected from $C_{1-8}$ alkyl, $C_{1-8}$ haloalkyl, $C_{3-6}$ cycloalkyl, $C_{2-8}$ alkenyl, $C_{2-8}$ alkynyl, —$COR^a$, —$CO_2R^a$, —$CONR^aR^b$, —$NR^aCOR^b$, —$SO_2R^a$, —$X^1COR^a$, —$X^1CO_2R^a$, —$X^1CONR^aR^b$, —$X^1NR^aCOR^b$, —$X^1SO_2R^a$, —$X^1SO_2NR^aR^b$, —$X^1NR^aR^b$, —$X^1OR^a$ and —$X^1R^a$, wherein $X^1$ is selected from $C_{1-4}$ alkylene and $C_{2-4}$ alkenylene and each $R^a$ and $R^b$ is independently selected from hydrogen, $C_{1-8}$ alkyl, $C_{1-8}$ haloalkyl, $C_{3-6}$ cycloalkyl, $C_{3-9}$ heterocycloalkyl and aryl-$C_{1-4}$alkyl, and wherein the aliphatic portions of each of the $R^4$ substituents is optionally substituted with from one to three members selected from —OH, —$OR^m$, —$OC(O)NHR^m$, —$OC(O)N(R^m)_2$, —SH, —$SR^m$, —$S(O)R^m$, —$S(O)_2R^m$, —$SO_2NH_2$, —$S(O)_2NHR^m$, —$S(O)_2N(R^m)_2$, —$NHS(O)_2R^m$, —$NR^mS(O)_2R^m$, —$C(O)NH_2$, —$C(O)NHR^m$, —$C(O)N(R^m)_2$, —$C(O)R^m$, —$NHC(O)R^m$, —$NR^mC(O)R^m$, —$NHC(O)NH_2$, —$NR^mC(O)NH_2$, —$NR^mC(O)NHR^m$, —$NHC(O)NHR^m$, —$NR^mC(O)N(R^m)_2$, —$NHC(O)N(R^m)_2$, —$CO_2H$, —$CO_2R^m$, —$NHCO_2R^m$, —$NR^mCO_2R^m$, —CN, —$NO_2$, —$NH_2$, —$NHR^m$, —$N(R^m)_2$, —$NR^mS(O)NH_2$ and —$NR^mS(O)_2NHR^m$, wherein each $R^m$ is independently an unsubstituted $C_{1-6}$ alkyl; and optionally, two $R^4$ substituents on adjacent carbon atoms are combined to form a fused five- or six-membered ring that is saturated or unsaturated.

The compounds provided herein are useful for binding to CCXCKR2 (also referred to as CXCR7), and treating diseases that are dependent, at least in part, on CCXCKR2 activity. Accordingly, the present invention provides in further aspects, compositions containing one or more of the above-noted compounds in admixture with a pharmaceutically acceptable excipient.

In still another aspect, the present invention provides methods for inhibiting the binding of chemokines I-TAC or SDF-1 to a CCXCKR2 receptor, comprising contacting a compound of the formula above, with a cell that expresses the CCX-CKR2 receptor for a time sufficient to inhibit the binding of the chemokines to the CCXCKR2 receptor.

In yet another aspect, the present invention provides methods of treating cancer comprising administering to a subject in need of such treatment a therapeutically effective amount of a compound of the above formula, for a period of time sufficient to treat the cancer.

BRIEF DESCRIPTION OF THE DRAWINGS

Not applicable

DETAILED DESCRIPTION OF THE INVENTION

I. Abbreviation and Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom or through a carbon atom. Non-limiting examples of aryl groups include phenyl, naphthyl and biphenyl, while non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, benzopyrazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl or heteroaryl group is attached to an alkyl group (e.g., benzyl, phenethyl, pyridylmethyl and the like).

The term "heterocycle" refers to a saturated or unsaturated non-aromatic cyclic group containing at least one sulfur, nitrogen or oxygen heteroatom. Each heterocycle can be attached at any available ring carbon or heteroatom. Each heterocycle may have one or more rings. When multiple rings are present, they can be fused together or linked covalently. Each heterocycle must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Non-limiting examples of heterocycle groups include pyrrolidine, piperidine, imidazolidine, pyrazolidine, butyrolactam, valerolactam, imidazolidinone, hydantoin, dioxolane, phthalimide, 1,4-dioxane, morpholine, thiomorpholine, thiomorpholine-S,S-dioxide, piperazine, pyran, pyridone, 3-pyrroline, thiopyran, pyrone, tetrahydrofuran, tetrahydrothiophene and the like.

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$, in a number ranging from zero to (2 m'+1), where m' is the total number of carbon atoms in such radical. R', R" and R''' each independently refer to hydrogen, unsubstituted C$_{1-8}$ alkyl, unsubstituted heteroalkyl, unsubstituted aryl, aryl substituted with 1-3 halogens, unsubstituted C$_{1-8}$ alkyl, C$_{1-8}$ alkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro(C$_1$-C$_4$)alkoxy, and perfluoro(C$_1$-C$_4$)alkyl, in a number ranging from zero to the total number of open valences on the aromatic ring system; and where R', R" and R''' are independently selected from hydrogen, C$_{1-8}$ alkyl, C$_{3-6}$ cycloalkyl, C$_{2-8}$ alkenyl, C$_{2-8}$ alkynyl, unsubstituted aryl and heteroaryl, (unsubstituted aryl)-C$_{1-4}$ alkyl, and unsubstituted aryloxy-C$_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

"CCXCKR2" also referred to as "RDC1," refers to a seven-transmembrane domain presumed G-protein coupled receptor (GPCR). The CCXCKR2 dog ortholog was originally identified in 1991. See, Libert et al. *Science* 244:569-572 (1989). The dog sequence is described in Libert et al., *Nuc. Acids Res.* 18(7):1917 (1990). The mouse sequence is described in, e.g., Heesen et al., *Immunogenetics* 47:364-370 (1998). The human sequence is described in, e.g., Sreedharan et al., *Proc. Natl. Acad. Sci. USA* 88:4986-4990 (1991), which mistakenly described the protein as a receptor of vasoactive intestinal peptide.

II. General

Compounds of the present invention can inhibit the binding of ligands to the CCXCKR2 receptor and are useful in the treatment of cancer, particularly solid tumor cancers and lymphomas. More recently, the inhibition of ligand binding to CCXCKR2 was noted to reduce the severity of rheumatoid arthritis in an animal model.

III. Embodiments of the Invention

Compounds

In one aspect, the present invention provides compounds having the formula:

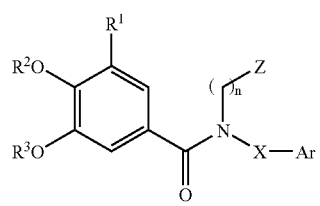

and all pharmaceutically acceptable salts thereof, wherein the subscript n is an integer of from 1 to 3; the symbol $R^1$ represents a hydrogen, halogen, $C_{1-8}$ alkoxy, $C_{1-8}$ alkyl, $C_{1-8}$ haloalkyl, $C_{3-6}$ cycloalkyl, $C_{3-6}$ cycloalkoxy, $C_{3-6}$ cycloalkyl $C_{1-4}$ alkyl or $C_{3-6}$ cycloalkyl $C_{1-4}$ alkoxy; the symbols $R^2$ and $R^3$ are each members independently selected from $C_{1-8}$ alkyl and $C_{1-8}$ haloalkyl, or are optionally combined with the oxygen atoms to which each is attached to from a five- to ten-membered ring optionally substituted with from one to four substituents selected from the group consisting of $C_{1-4}$ alkyl and $C_{1-4}$ haloalkyl; the letter X represents a bond, $CH_2$ or —CH(CH$_3$)—; the symbol Ar represents a linked- or fused-bicyclic aromatic ring system; and the letter Z represents a four-, five-, six- or seven-membered saturated nitrogen heterocyclic ring that is optionally substituted with from one to four $R^4$ substituents independently selected from $C_{1-8}$ alkyl, $C_{1-8}$ haloalkyl, $C_{3-6}$ cycloalkyl, $C_{2-8}$ alkenyl, $C_{2-8}$ alkynyl, —COR$^a$, —CO$_2$R$^a$, —CONR$^a$R$^b$, —NR$^a$COR$^b$, —SO$_2$R$^a$, —X$^1$COR$^a$, —X$^1$CO$_2$R$^a$, —X$^1$CONR$^a$R$^b$, —X$^1$NR$^a$COR$^b$, —X$^1$SO$_2$R$^a$, —X$^1$SO$_2$NR$^a$R$^b$, —X$^1$NR$^a$R$^b$, —X$^1$OR$^a$ and —X$^1$R$^a$, wherein $X^1$ is selected from $C_{1-4}$ alkylene and $C_{2-4}$ alkenylene and each $R^a$ and $R^b$ is independently selected from hydrogen, $C_{1-8}$ alkyl, $C_{1-8}$ haloalkyl, $C_{3-6}$ cycloalkyl, $C_{3-9}$ heterocycloalkyl and aryl-$C_{1-4}$alkyl, and wherein the aliphatic portions of each of the $R^4$ substituents is optionally substituted with from one to three members selected from —OH, —OR$^m$, —OC(O)NHR$^m$, —OC(O)N(R$^m$)$_2$, —SH, —SR$^m$, —S(O)R$^m$, —S(O)$_2$R$^m$, —SO$_2$NH$_2$, —S(O)$_2$NHR$^m$, —S(O)$_2$N(R$^m$)$_2$, —NHS(O)$_2$R$^m$, —NR$^m$S(O)$_2$R$^m$, —C(O)NH$_2$, —C(O)NHR$^m$, —C(O)N(R$^m$)$_2$, —C(O)R$^m$, —NHC(O)R$^m$, —NR$^m$C(O)R$^m$, —NHC(O)NH$_2$, —NR$^m$C(O)NH$_2$, —NR$^m$C(O)NHR$^m$, —NHC(O)NHR$^m$, —NR$^m$C(O)N(R$^m$)$_2$, —NHC(O)N(R$^m$)$_2$, —CO$_2$H, —CO$_2$R$^m$, —NHCO$_2$R$^m$, —NR$^m$CO$_2$R$^m$, —CN, —NO$_2$, —NH$_2$, —NHR$^m$, —N(R$^m$)$_2$, —NR$^m$S(O)NH$_2$ and —NR$^m$S(O)$_2$NHR$^m$, wherein each $R^m$ is independently an unsubstituted $C_{1-6}$ alkyl; and optionally, two $R^4$ substituents on adjacent carbon atoms are combined to form a fused five- or six-membered ring that is saturated or unsaturated.

In some embodiments, Z is selected from

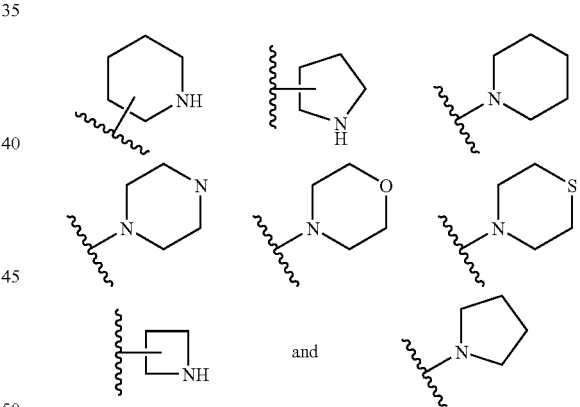

wherein the wavy line indicates the point of attachment to the remainder of the molecule, and each of the Z groups is optionally substituted with from one to four $R^4$ substituents as provided above.

In some embodiments, Z is

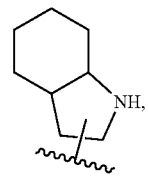

wherein the wavy line indicates the point of attachment to the remainder of the compound, and the Z group is optionally substituted with from one to four $R^4$ substituents as provided above.

In one group of embodiments, Ar is a fused bicyclic aromatic rings system selected from naphthalene, quinoline, benzothiophene, isoquinoline, benzofuran, indole, benzothiazole, benzimidazole, 1,4-benzodioxan, quinoxaline, quinazoline, cinnoline and naphthyridine.

In another group of embodiments, Ar is a linked-bicyclic aromatic ring system selected from biphenyl (wherein the phenyl rings are connected in an ortho- meta- or para-orientation relative to the attachment to the remainder of the compound), phenylthiazolyl, phenylpyrazolyl, pyridylthiazolyl and phenyl substituted with a 5- or 6-membered heteroaryl moiety (e.g., thiazolyl, thienyl, imidazolyl, pyrazolyl, furyl, oxazolyl, pyridyl, pyrimidinyl, pyrazinyl, and the like), wherein each of the above is optionally substituted with from one to six substituents selected from those provided in general for aryl groups (see above). In some preferred embodiments, the 5- or 6-membered heteroaryl group is selected from pyrazolyl, thiazolyl, 1,2,3-triazolyl and pyridyl.

In certain preferred embodiments, the subscript n is 1 or 2. In other preferred embodiments, the symbol $R^1$ represents a hydrogen or $C_{1-8}$ alkoxy. In still other preferred embodiments, the symbols $R^2$ and $R^3$ each independently represent methyl, ethyl, propyl, isopropyl, butyl, sec-butyl, isobutyl, tert-butyl, or their $C_{1-4}$ haloalkyl counterparts (e.g., trifluoromethyl, 2,2,2-trichloroethyl, 3-bromopropyl, and the like).

In still other embodiments, $R^2$ and $R^3$ are combined with the oxygen atoms to which each is attached to form a 5- or 6-membered ring optionally substituted with from one to four methyl groups.

In a particularly preferred group of embodiments, n is 1 or 2; $R^1$ is selected from the group consisting of hydrogen and $C_{1-8}$ alkoxy; $R^2$ and $R^3$ are each independently selected from the group consisting of methyl, ethyl, propyl, isopropyl, butyl, sec-butyl, isobutyl, tert-butyl and $C_{1-4}$ haloalkyl; X is $CH_2$; Ar is a fused bicyclic aromatic ring system selected from the group consisting of naphthalene, quinoline, benzothiophene, isoquinoline, benzofuran, indole, benzothiazole, benzimidazole, 1,4-benzodioxan, quinoxaline, quinazoline, cinnoline and naphthyridine; Z is a member selected from the group consisting of

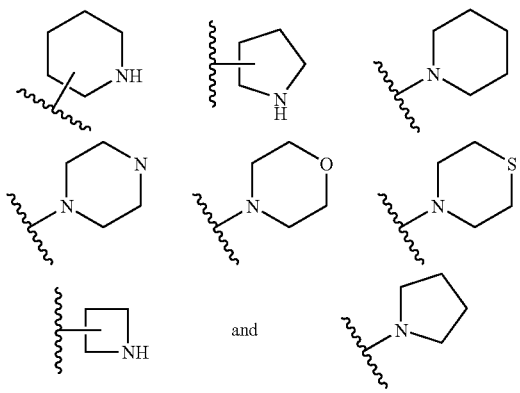

wherein the wavy line indicates the point of attachment to the remainder of the compound and each Z is optionally substituted with one or two $R^4$ substituents independently selected from the group consisting of $C_{1-8}$ alkyl, $C_{3-6}$ cycloalkyl, —$X^1OR^a$ and —$X^1R^a$, wherein $X^1$ is a member selected from the group consisting of $C_{1-4}$ alkylene and $C_{2-4}$ alkenylene and $R^a$ is selected from the group consisting of $C_{1-8}$ alkyl, $C_{3-6}$ cycloalkyl and $C_{3-9}$ heterocycloalkyl.

In another particularly preferred group of embodiments, n is 1 or 2; $R^1$ is selected from the group consisting of hydrogen and $C_{1-8}$ alkoxy; $R^2$ and $R^3$ are each independently selected from the group consisting of methyl, ethyl, propyl, isopropyl, butyl, sec-butyl, isobutyl, tert-butyl and $C_{1-4}$ haloalkyl; X is a bond; Ar is a substituted or unsubstituted linked-bicyclic aromatic ring system selected from the group consisting of biphenyl, phenylthiazolyl, phenylpyrazolyl, pyridylthiazolyl and phenyl substituted with a 5- or 6-membered heteroaryl moiety; Z is a member selected from the group consisting of

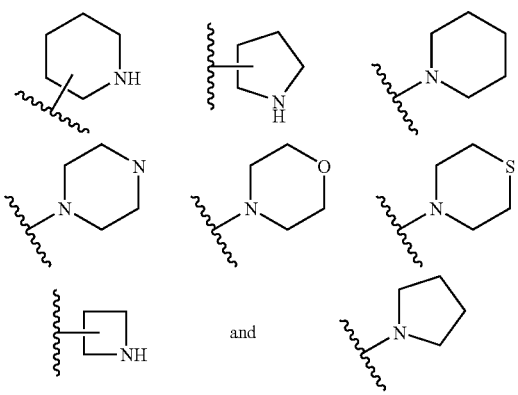

wherein the wavy line indicates the point of attachment to the remainder of the compound and each Z is optionally substituted with one or two $R^4$ substituents independently selected from the group consisting of $C_{1-8}$ alkyl, $C_{3-6}$ cycloalkyl, —$X^1OR^a$ and —$X^1R^a$, wherein $X^1$ is a member selected from the group consisting of $C_{1-4}$ alkylene and $C_{2-4}$ alkenylene and $R^a$ is selected from the group consisting of $C_{1-8}$ alkyl, $C_{3-6}$ cycloalkyl and $C_{3-9}$ heterocycloalkyl.

Compositions

In addition to the compounds provided above, compositions useful for treating cancer, as well as other diseases modulated by CCXCKR2 in humans and animals will typically contain a pharmaceutical carrier or diluent.

The term "composition" as used herein is intended to encompass a product comprising the specified ingredients, preferably in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 20020012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

Methods of Use

While not wishing to be bound by any particular theory, the compositions of the present invention are considered to provide a therapeutic effect by inhibiting the binding of SDF-1 and/or I-TAC to the CCXCKR2 receptor. SDF-1 is known to provide a target for interfering with the development or spread of cancer cells in a mammal, such as a human. Inhibition of the binding of I-TAC to the CCXCKR2 receptor prevents the formation of vascularized tumors. By contacting the compositions described above with a cancer cell that expresses the CCXCKR2 receptor, the invasive response that would otherwise trigger in the cancer cell can be reduced. Accordingly, the present invention is also directed to methods that are useful in the prevention and/or treatment of cancer, particularly solid tumor cancers, more particularly breast cancer.

As determined by radiolabeled SDF-1 binding and I-TAC displacement, CCXCKR2 was preferentially expressed in human transformed cells. Included in Table A are those tissue types in which CCXCKR2 was expressed (CCXCKR2$^+$) as well as those tissue types in which CCXCKR2 was not expressed (CCXCKR2$^-$).

TABLE A

| CCXCKR2$^+$ | CCXCKR2$^-$ |
|---|---|
| Human Cervical Adenocarcinoma | Normal Mouse Adult Progenitors (c-kit+ & CD34+ BM derived) |
| Human Adenocarcinoma, Mammary Gland | Human Acute Lymphoblastic Leukemia, T Cell |
| Human Burkitt's Lymphoma, B Lymphocyte | Normal Murine Bone Marrow |
| Human Glioblastoma Multiforme, Brain | Normal Murine Thymus |
| Human Carcinoma, Prostate | Normal Murine Lung |
| Murine Lymphoblastic Leukemia, B Lymphocyte | Normal Murine Spleen |
| Murine Mammary Gland Tumor | Normal Murine Liver |
| Normal Murine Fetal Liver | Normal Murine PBL |
| Normal Mouse Brain | Normal Human PBL |
| Normal Mouse Kidney | Normal Murine Heart |
| | Normal Murine Pancreas |

In one embodiment, a preferred method of inhibiting the binding of the chemokines SDF-1 and/or I-TAC to a CCXCKR2 receptor includes contacting one or more of the previously mentioned compounds with a cell that expresses the CCXCKR2 receptor for a time sufficient to inhibit the binding of these chemokines to the CCXCKR2 receptor.

Methods of Treating Cancer

More specifically, the present invention also provides a method of treating cancer. A preferred method of treating cancer, includes administering a therapeutically effective amount of one or more of the previously mentioned compounds (or salts thereof) to a cancer patient for a time sufficient to treat the cancer.

For treatment, the compositions of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Standard in vivo assays demonstrating that the compositions of the present invention are useful for treating cancer include those described in Bertolini, F., et al., *Endostatin, an antiangiogenic drug, induces tumor stabilization after chemotherapy or anti-CD20 therapy in a NOD/SCID mouse model of human high-grade non-Hodgkin lymphoma*. Blood, No. 1, Vol. 96, pp. 282-87 (1 Jul. 2000); Pengnian, L., *Anti-angiogenic gene therapy targeting the endothelium-specific receptor tyrosine kinase Tie2*. Proc. Natl. Acad. Sci. USA, Vol. 95, pp. 8829-34 (July 1998); and Pulaski, B. *Cooperativity of Staphylococcal aureus Enterotoxin B Superantigen, Major Histocompatibility Complex Class II, and CD80 for Immunotherapy of Advanced Spontaneous Metastases in a Clinically Relevant Postoperative Mouse Breast Cancer Model*. Cancer Research, Vol. 60, pp. 2710-15 (May 15, 2000).

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

The compounds and compositions of the present invention can be combined with other compounds and compositions having related utilities to prevent and treat cancer and diseases or conditions associated with CCXCKR2 signaling. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: cisplatin, paclitaxel, methotrexate, cyclophosphamide, ifosfamide, chlorambucil, carmustine, carboplatin, vincristine, vinblastine, thiotepa, lomustine, semustine, 5-fluorouracil and cytarabine. The weight ratio of the compound of the present invention to the second active ingredient may be varied and will depend upon the effective dose of each ingredient. Generally, an effective dose of each will be used. Thus, for example, when a compound of the present invention is combined with a second anticancer agent, the weight ratio of the compound of the present invention to the second agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Methods of Treating Inflammation

Still further, the compounds and compositions of the present invention are useful for the treatment of inflammation, and can be combined with other compounds and compositions having therapeutic utilities that may require treatment either before, after or simultaneously with the treatment of cancer or inflammation with the present compounds. Accordingly, combination methods and compositions are also a component of the present invention to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

As noted, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), (l) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

IV. EXAMPLES

Example 1

This example illustrates the preparation of N—(S)-(1-Cyclohexylmethyl-pyrrolidine-2-ylmethyl)-3,4-dimethoxy-N-naphthalen-2-ylmethyl-benzamide.

Step 1: (S)-2-{[Naphthalen-2-ylmethyl]-amino]-methyl}-pyrrolidin-1-carboxylic acid tert-butyl ester.

Under nitrogen, 2-(S)-aminomethyl-pyrrolidin-1-carboxylic acid tert-butyl ester (prepared according to the scheme 1) 2 g (10 mmol) was dissolved in 50 mL anhydrous dichloromethane. To this solution was added naphthalene-2-carbaldehyde 2 g (13 mmol), and molecular sieves. The mixture was stirred overnight. Molecular sieves were filtered and the organic portion was concentrated. The resulting mixture was taken up in 100 mL methanol cooled at 0° C., and sodium borohydride 0.75 g (20 mmol) was added. After 1 hour, thin layer chromatography showed the completion of reaction. To this mixture was added very slowly 10 mL of water, and was extract with dichloromethane 3 times, combined organic layer was washed with brine, dried over magnesium sulfate, filtered and concentrated, gave 2.76 g orange oil (no purification). LC-MSD, m/z for: $C_{21}H_{28}N_2O_2$ [M+H]: 341.1. LC retention time on HPLC, C18 column gradient 20-95% acetonitrile-0.1% TFA in 7 minutes: 3.2 min Step 2: 2-(S)-{[(3,4-Dimethoxy-benzoyl)-naphthalen-2-ylmethyl-amino]-methyl}-pyrrolidine-1-carboxylic acid tert-butyl ester.

3,4-Dimethoxy benzoic acid 1.04 g (5.72 mmol) was dissolved in 30 mL tetrahydrofuran, to this mixture was added 1-ethyl-3-(3-dimethylaminopropyl) carbodiimide hydro-

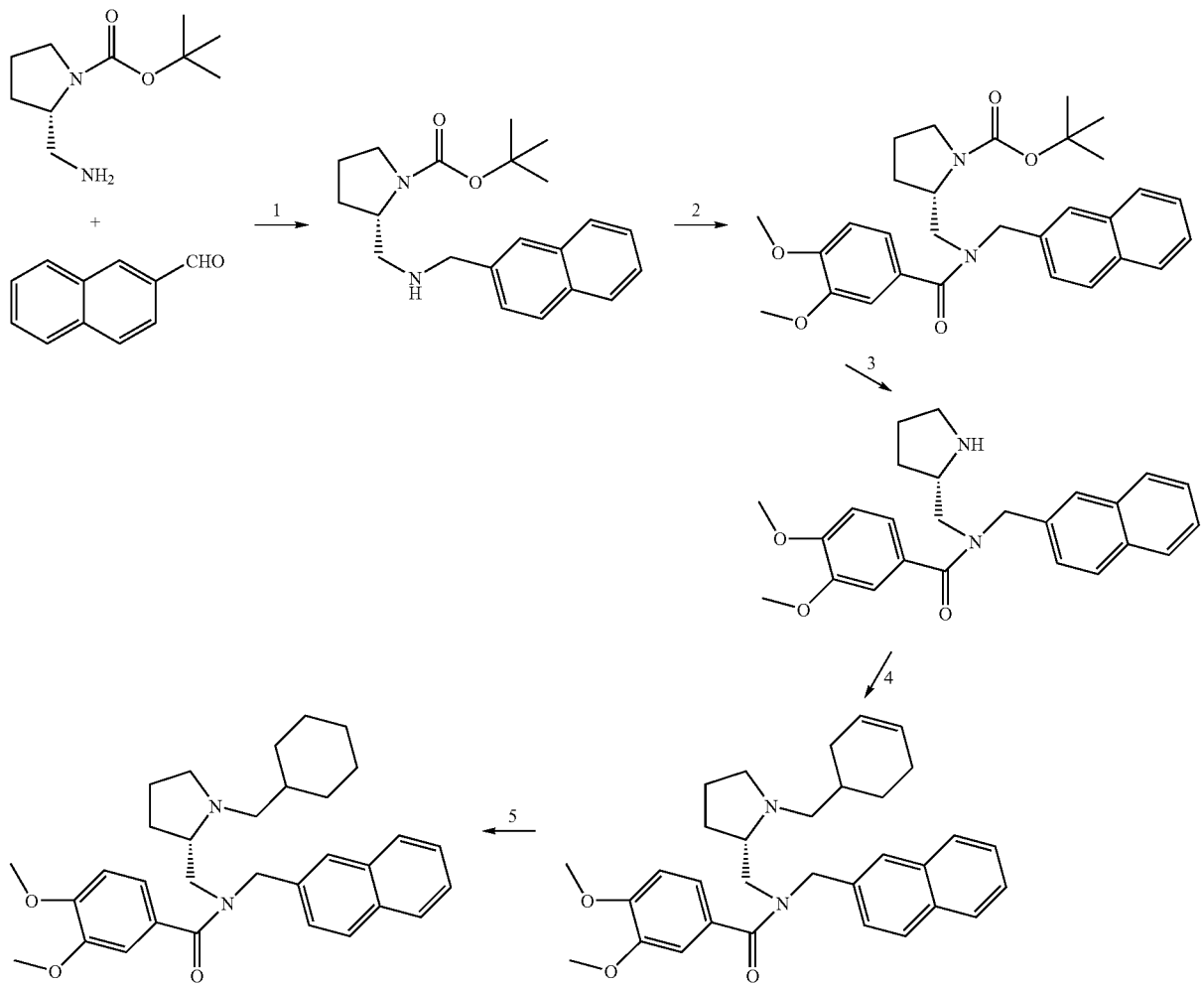

Method 1 chloride 1.4 g (6.6 mmol), triethylamine 0.66 g (5.72 mmol), after 30 minutes 1-hydroxybenzotriazole 0.77 g (5.72 mmol) was added. The mixture was stirred one hour. To this mixture was added 2-{[naphthalen-2-ylmethyl]-amino]-methyl}-pyrrolidin-1-carboxylic acid tert-butyl ester 1.5 g (4.4 mmol). The mixture was stirred 1 night at room temperature. Added 50 mL of saturated sodium bicarbonate and extract with ethyl acetate 3 times 100 mL. The combined organic layer was dried over magnesium sulfate, filtered, and concentrated under vacuum. Purification over silica gel hexane: 1-dichloromethane: 1, lead to 1.1 g white powder. LC-MSD, m/z for: $C_{30}H_{36}N_2O_5$ [M+H]: 505.2. LC retention time on HPLC, C18 column gradient 20-95% acetonitrile with 0.1% TFA in 7 minutes: 5.0 min.

Step 3 (S)-3,4-Dimethoxy-N-naphthalen-2ylmethyl-N-pyrrolidin-2-ylmethyl-benzamide.

In 20 mL mixture of dichloromethane and trifluoroacetic acid 30%, was dissolved 2-{[(3,4-Dimethoxy-benzoyl)-naphthalen-2-ylmethyl-amino]-methyl}-pyrrolidine-1-carboxylic acid tert-butyl ester 1.1 g (2.18 mmol). After 1 hour at room temperature, saturated solution of sodium bicarbonate was added until basic pH, the mixture was extracted with dichlorometane, dried over magnesium sulfate, filtered and concentrated under vacuum, yield to 0.88 g. LC-MSD, m/z for: $C_{25}H_{28}N_2O_3$ [M+H]: 404.2. LC retention time on HPLC, C18 column gradient 20-95% acetonitrile with 0.1% TFA in 7 minutes: 1.37 min.

Step 4: N—(S)-(1-Cyclohex-3-enylmethyl-pyrrolidin-2-ylmethyl)-3,4-dimethoxy-N-naphthalen-2-ylmethyl-benzamide.

3,4-Dimethoxy-N-naphthalen-2ylmethyl-N-(S)-pyrrolidin-2-ylmethyl-benzamide 0.88 g (2.17 mmol) was dissolved in 20 mL anhydrous dichloromethane, to this mixture was added 1,2,3,6-tetrahydrobenzaldehyde 0.26 g (2.39 mmol), sodium triacethoxyborohydride 0.68 g (3.25 mmol), and molecular sieve. The reaction mixture was stirred under nitrogen overnight at room temperature. The molecular sieve was filtered, to this mixture was added saturated sodium bicarbonate, and was extracted 3 times with dichloromethane. Combined organic layer was dried over magnesium sulfate, filtered, and concentrated under vacuum. Gave 0.8 g of oil, which was purified using reverse phase HPLC C18 column, with a gradient of 20 to 90% acetonitrile-0.1% TFA, yield to 0.6 g of white powder. LC-MSD, m/z for: $C_{32}H_{38}N_2O_3$ [M+H]: 499.4. LC retention time on HPLC, C18 column gradient 20-95% acetonitrile with 0.1% TFA in 7 minutes: 3.87 min.

Step 5: N—(S)-(1-Cyclohexylmethyl-pyrrolidin-2-ylmethyl)-3,4-dimethoxy-N-naphthalen-2-ylmethyl-benzamide.

N—(S)-(1-Cyclohex-3-enylmethyl-pyrrolidin-2-ylmethyl)-3,4-dimethoxy-N-naphthalen-2-ylmethyl-benzamide was dissolved in 5 mL methanol, to this solution was added 2 mg palladium 5% on carbon. The mixture was stirred under hydrogen at room temperature, under atmospheric pressure. After 2 hours the reaction goes to completion. The catalyst was filtered, methanol concentrated under vacuum, yield to 10 mg of white powder. LC-MSD, m/z for: $C_{32}H_{40}N_2O_3$ [M+H]: 501.4. LC retention time on HPLC, C18 column gradient 20-95% acetonitrile with 0.1% TFA in 7 minutes: 4.52 min.

Scheme 1:
Preparation of 2-(S)-Aminomethyl-pyrrolidine-1-carboxylic acid tert-butyl ester

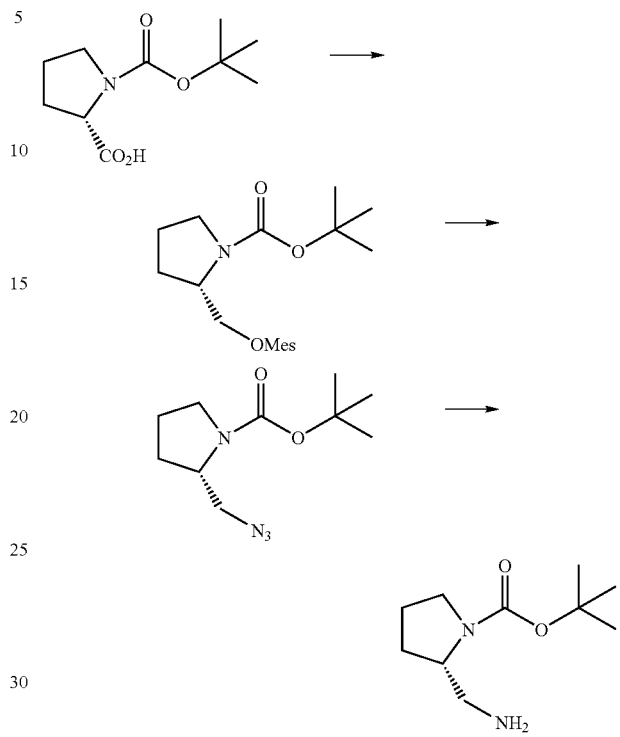

Mehod 2:

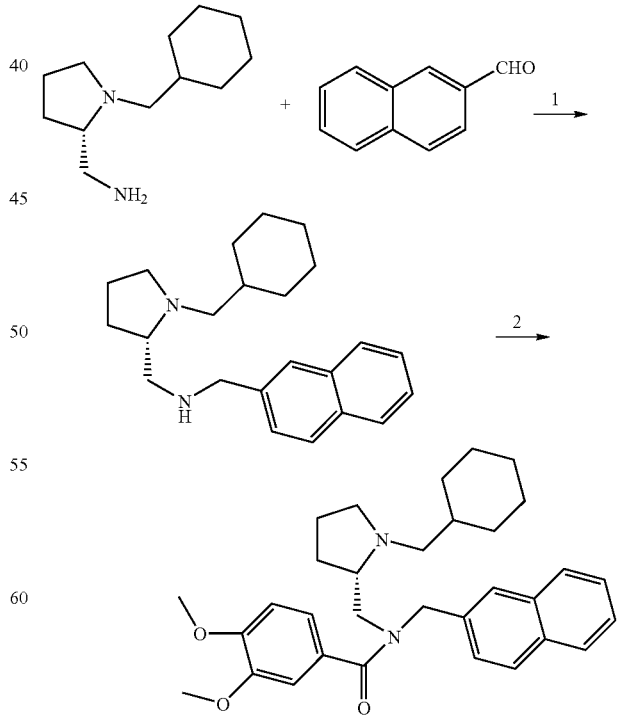

Step 1: (S)-(1-Cyclohexylmethyl-pyrrolidin-2-ylmethyl)-naphthalen-2-ylmethyl-amine (S)—C-(1-Cyclohexylmethyl-pyrrolidin-2-yl)-methylamine (prepared according to scheme 2) 0.24 g (1 mmol), and naphthalene-2-carbaldehyde 0.19 g (1.2 mmol), were dissolved in 10 mL dichloromethane. To this mixture was added sodium triacethoxyborohydride 0.51 g (2 mmol), and molecular sieve. The reaction was stirred overnight under nitrogen. Molecular sieve was filtered, washed with 3 mL HCl, acidic layer was transformed to basic pH, with powder sodium bicarbonate, and extracted with ethyl acetate. The combined organic layer dried over magnesium sulfate, filtered and concentrated, yield to 100 mg of yellow oil.

Step 2: N—(S)-(1-Cyclohexylmethyl-pyrrolidin-2-ylmethyl)-3,4-dimethoxy-N-naphthalen-2-ylmethyl-benzamide.

Prepared according to step 2 of method 1, from 3,4-dimethoxy benzoic acid 40 mg (0.22 mmol), 1-ethyl-3-(3-dimethylaminopropyl) carbodiimide hydrochloride 40 mg (0.22 mmol), 1-hydroxybenzotriazole 20 mg (0.18 mmol), triethylamine 0.03 mL (0.22 mmol) and (S)-(1-cyclohexylmethyl-pyrrolidin-2-ylmethyl)-naphthalen-2-ylmethyl-amine 50 mg (0.15 mmol), in 1 mL tetrahydrofuran. yield to 72 mg of white powder. LC-MSD, m/z for: $C_{32}H_{40}N_2O_3$ [M+H]: 501.4. LC retention time on HPLC, C18 column gradient 20-95% acetonitrile with 0.1% TFA in 7 minutes: 4.2 min.

Scheme 2:
Preparation of C-(1-(S)-Cyclohexylmethyl-pyrrolidin-2-yl)-methylamine

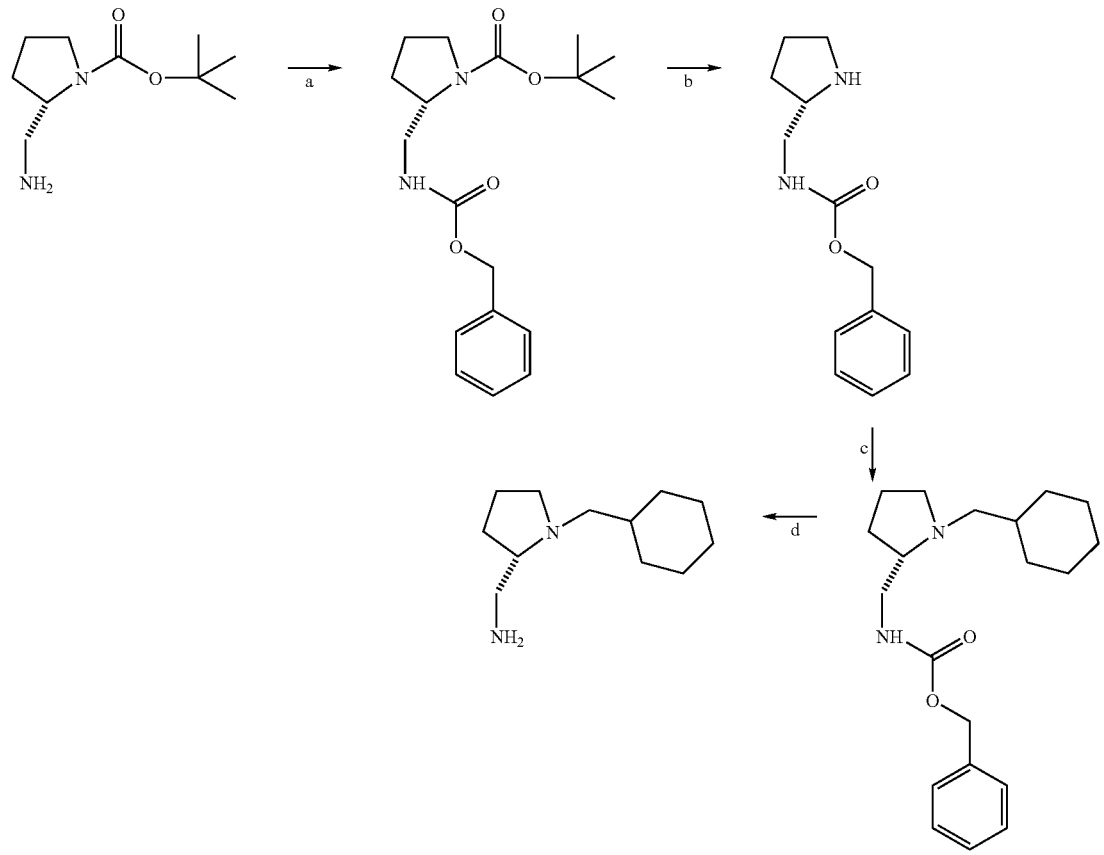

a: Benzylchloroformate, sodium carbonate, THF, 3 h, RT
b: 6N HCl, dioxane, 14 h, RT
c: Cyclohexane carboxaldehyde, methanol, acetic acid, sodiumcyanoborohydride, 0° C. to RT
d: 10% Pd/charcoal, methanol, H₂ 2.5 Kg for 5 h Example 2

This example illustrates the preparation of N—(S)-(1-Cyclohexylmethyl-pyrrolidin-2-ylmethyl)-3,4-dimethoxy-N-quinolin-3-ylmethyl-benzamide.

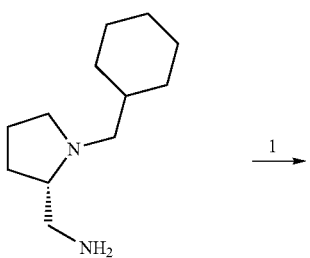

-continued

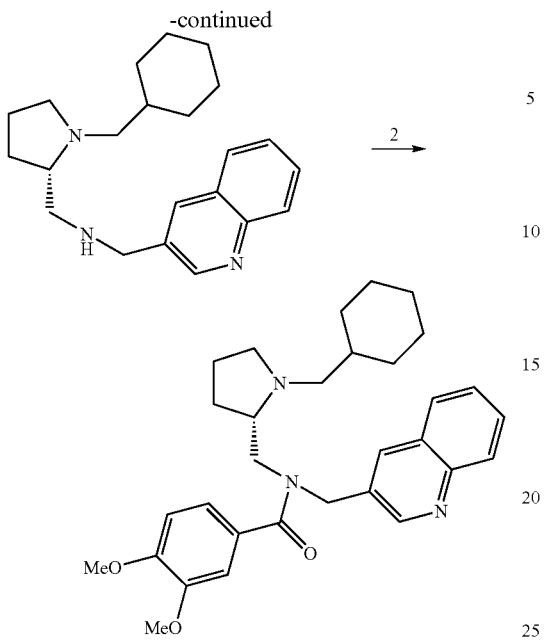

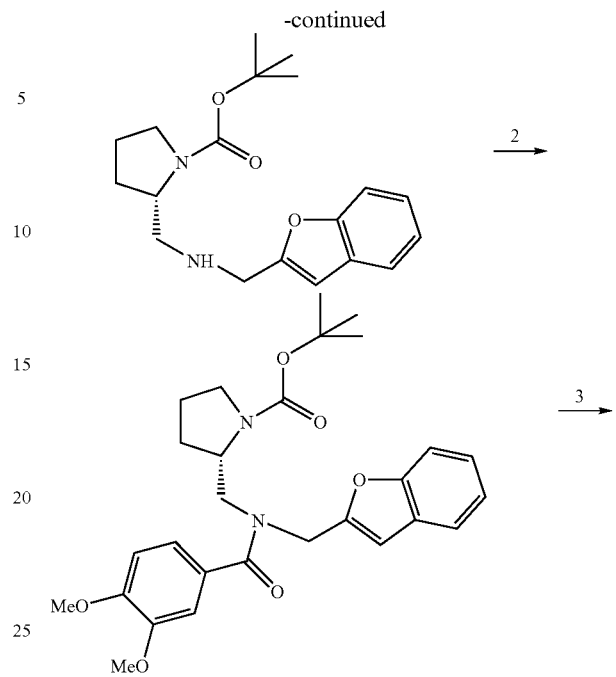

Step 1: (S)-(1-Cyclohexylmethyl-pyrrolidin-2-ylmethyl)-quinolin-3-ylmethyl-amine:

Experimental condition analogous to Example 1, from (S)—C-(1-cyclohexylmethyl-pyrrolidin-2-yl)-methylamine 0.25 g (1.3 mmol), quinoline-3-carbaldehyde 0.2 g (1.3 mmol), sodium triacethoxyborohydride 0.53 g (2.6 mmol), and molecular sieve in 8 mL dichloromethane. Yield to 40 mg of compound.

Step 2: N—(S)-(1-Cyclohexylmethyl-pyrrolidin-2-ylmethyl)-3,4-dimethoxy-N-quinolin-3-ylmethyl-benzamide Experimental condition analogous to Example 1, from 3,4-dimethoxy benzoic acid 32 mg (0.17 mmol), 1-ethyl-3-(3-dimethylaminopropyl) carbodiimide hydrochloride 34 mg (0.17 mmol), 1-hydroxybenzotriazole 19 mg (0.14 mmol), triethylamine 0.24 mL and (S)-(1-cyclohexylmethyl-pyrrolidin-2-ylmethyl)-quinolin-3-ylmethyl-amine 40 mg (0.11 mmol) in 1 mL of tetrahydrofuran, yield after reverse phase HPLC purification with a C18 column, gradient of 20-80% acetonitrile −0.1% TFA, gave 11 mg white solid. LC-MSD, m/z for: $C_{31}H_{39}N_3O_3$ [M+H]: 502.2. LC retention time on HPLC, C18 column gradient 20-95% acetonitrile with 0.1% TFA in 7 minutes: 3.2 min.

Example 3

This example illustrates the preparation of N-benzofuran-2-ylmethyl-N—(S)-(1-cyclohexylmethyl-pyrrolidin-2-ylmethyl)-3,4-dimethoxy-benzamide.

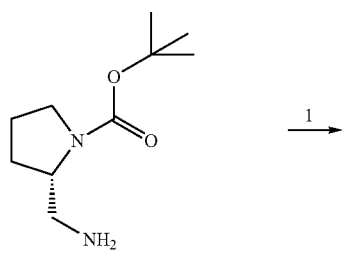

Step 1: 2-(S)-{[(Benzofuran-2-ylmethyl)-amino]-methyl}-pyrrolidin-1-carboxylic acid tert-butyl ester:

Experimental condition analogous to Example 1, from benzofuran-2-carbaldehyde 0.15 g (1 mmol), 2-aminomethyl-pyrrolidine-1-carboxylic acid tert-butyl ester 0.26 g (1.2 mmol), and sodium triacethoxyborohydride 0.43 g (2 mmol), in 10 mL dichloromethane, yield to 0.2 g of oil 88% pure.

Step 2: 2-(S)-{[Benzofuran-2-ylmethyl-(3,4-dimethoxybenzoyl)-amino]-methyl}-pyrrolidine-1-carboxylic acid tert-butyl ester Experimental condition analogous to Example 1, from 3,4,5-trimethoxy benzoic acid 72 mg (0.39 mmol), 1-ethyl-3-(3-dimethylaminopropyl) carbodiimide hydrochloride 75 mg (0.39 mmol), 1-hydroxybenzotriazole 45 mg (0.33 mmol), triethylamine 0.05 mL (0.39 mmol), and 2-(S)-{[(benzofuran-2-ylmethyl)-amino]-methyl}-pyrrolidine-1-carboxylic acid tert-butyl ester, 100 mg (0.3 mmol) in 3 mL tetrahydrofuran. The compound was purified through silica gel chromatography elution with ethyl acetate: methanol 9:1, gave 93 mg of white oily compound.

Step 3: N-Benzofuran-2-ylmethyl-N—(S)-(1-cyclohexylmethyl-pyrrolidin-2-ylmethyl)-3,4-dimethoxy-benzamide Experimental condition analogous to Example 1, from 2-(S)-{[benzofuran-2-ylmethyl-(3,4-dimethoxy-benzoyl)-amino]-methyl}-pyrrolidin-1-carboxylic acid tert-butyl ester 110 mg (0.22 mmol), and 1 mL of mixture of trifluoroacetic acid and dichloromethane 17%, after deprotection 64 mg (0.16 mmol) of the N-benzofuran-2-ylmethyl-3,4-dimethoxy-N—(S)-pyrrolidin-2-ylmethyl-benzamide, cyclohexanecarbaldehyde 19 mg (0.17 mmol), sodium triacethoxyborohydride 68 mg (0.32 mmol) and molecular sieve, in 1 mL dichloromethane. Yield to 50 mg of white powder. LC-MSD, m/z for: $C_{30}H_{38}N_2O_4$ [M+H]: 491.2. LC retention time on HPLC, C18 column gradient 20-95% acetonitrile with 0.1% TFA in 7 minutes: 3.91 min.

Example 4

This example illustrates the preparation of N-Benzofuran-2-ylmethyl-N—(S)-(1-cyclohexylmethyl-pyrrolidin-2-ylmethyl)-3,4,5-trimethoxy-benzamide.

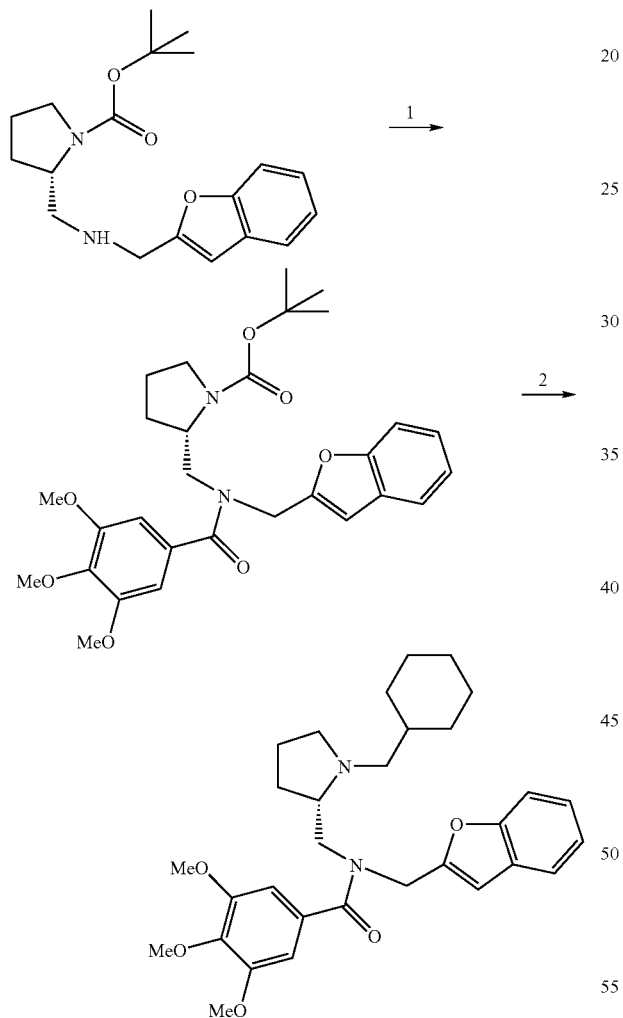

Step 1: 2-(S)-{[Benzofuran-2-ylmethyl-(3,4,5-trimethoxy-benzoyl)-amino]-methyl}-pyrrolidin-1-carboxylic acid tert-butyl ester.

2-(S)-{[Benzofuran-2-ylmethyl]-amino]-methyl}-pyrrolidin-1-carboxylic acid tert-butyl ester 0.33 g (0.28 mmol), 3,4,5-trimethoxy-benzoyl chloride 65 mg (0.28 mmol) and triethylamine 0.04 mL (0.28 mmol). After 1 hour, saturated sodium bicarbonate added and the mixture extracted with dichloromethane, combined organic layer, dried over magnesium sulfate, filtered, and concentrated under vacuum. Purification over silica gel chromatography, elution ethyl acetate-hexane 5.5-4.5, gave 100 mg of light yellow oil.

Step 2: N-Benzofuran-2-ylmethyl-N—(S)-(1-cyclohexylmethyl-pyrrolidin-2-ylmethyl)-3,4,5-trimethoxy-benzamide.

Experimental condition analogous to example 3, from of —(S)-{[benzofuran-2-ylmethyl-(3,4,5-trimethoxy-benzoyl)-amino]-methyl}-pyrrolidin-1-carboxylic acid tert-butyl ester 0.1 g (0.19 mmol), 0.15 mL (1.9 mmol) trifluoroacetic acid, in 1 mL dichloromethane. The deprotected amine 0.06 g (0.188 mmol) was added to cyclohexanecarbaldehyde 0.023 g (0.19 mmol), and sodium acethoxy borohydride 0.06 g (0.38 mmol) in 1 mL of dichloromethane, yield 70 mg of white powder. LC-MSD, m/z for: $C_{31}H_{40}N_2O_5$ [M+H]: 521.2. LC retention time on HPLC, C18 column gradient 20-95% acetonitrile with 0.1% TFA in 7 minutes: 3.88 min.

Example 5

This example illustrates the preparation of 3,4,5-Trimethoxy-N-[2-(1-methyl-pyrrolidin-2-yl)-ethyl]-N-naphthalen-2ylmethyl-benzamide.

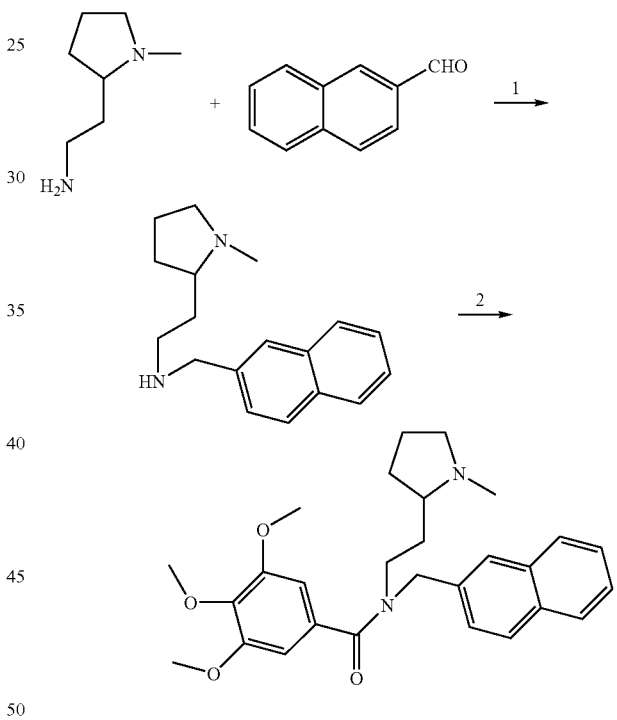

Step 1: [2-(1-Methyl-pyrrolidin-2-yl)-ethyl]-naphthalen-2-ylmethyl-amine.

Experimental condition analogous to Example 1, from 2-naphthalencarboxaldehyde 0.15 g (1 mmol), 2-(1-methyl-pyrrolidin-2-yl)-ethylamine 0.14 g (1.1 mmol), and sodium triacethoxyborohydride 0.31 g (1.5 mmol), in 10 mL dichloromethane. The crude material is 110 mg pale yellow oil.

Step 2: 3,4,5-Trimethoxy-N-[2-(1-methyl-pyrrolidin-2-yl)-ethyl]-N-naphthalen-2ylmethyl-benzamide.

Experimental condition analogous to Example 4, from [2-(1-methyl-pyrrolidin-2-yl)-ethyl]-naphthalen-2-ylmethyl-amine 0.11 g (0.42 mmol), 3,4,5-trimethoxy-benzoylchloride 0.11 g (0.51 mmol), and triethylamine 0.06 g (0.72 mmol), in 10 mL of anhydrous dichloromethane. The compound was purified using reverse phase HPLC, C18 column gradient of 20-80% acetonitrile-0.1% TFA, yield to 180 mg of pure material. LC-MSD, m/z for: $C_{28}H_{34}N_2O_4$ [M+H]: 463.5. LC retention time on HPLC, C18 column gradient 20-95% acetonitrile with 0.1% TFA in 7 minutes: 3.01 min.

Example 6

This example illustrates the preparation of 3,4,5-Trimethoxy-N[2-(1-methyl-pyrrolidin-2-yl)-ethyl]-N-naphthalen-1-ylmethyl-benzamide.

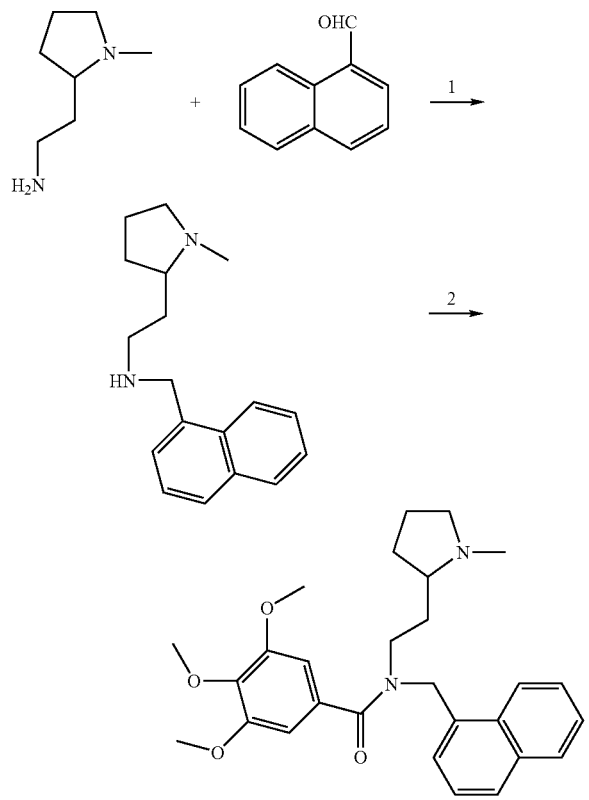

Step 1: [2-(1-Methyl-pyrrolidin-2-yl)-ethyl]-naphthalen-1-ylmethyl-amine.

Experimental condition analogous to Example 5, from 1-naphthalencarboxaldehyde 0.15 g (1 mmol), 2-(1-methyl-pyrrolidin-2-yl)-ethylamine 0.14 g (1.1 mmol), and sodium triacethoxyborohydride 0.31 g (1.5 mmol), in 10 mL dichloromethane. The crude material is 210 mg clear oil.

Step 2: 3,4,5-Trimethoxy-N[2-(1-methyl-pyrrolidin-2-yl)-ethyl]-N-naphthalen-1-ylmethyl-benzamide.

Experimental condition analogous to Example 5, from [2-(1-Methyl-pyrrolidin-2-yl)-ethyl]-naphthalen-1-ylmethyl-amine 0.21 g (0.79 mmol), 3,4,5-trimethoxy-benzoylchloride 0.0.21 g (0.95 mmol), and triethylamine 0.11 g (1.18 mmol), in 15 mL of anhydrous dichloromethane. The compound was purified using reverse phase HPLC, C18 column with a gradient of 20-80% acetonitrile-0.1% TFA, yield to 280 mg of pure material. LC-MSD, m/z for: $C_{28}H_{34}N_2O_4$ [M+H]: 463.5. LC retention time on HPLC, C18 column gradient of 20-95% acetonitrile with 0.1% TFA in 7 minutes: 3.13 min.

Example 7

This example illustrates the preparation of N-Benzofuran-2-ylmethyl-3,4,5-trimethoxy-N-[2-(1-methyl-pyrrolidin-2-yl)-ethyl]-benzamide.

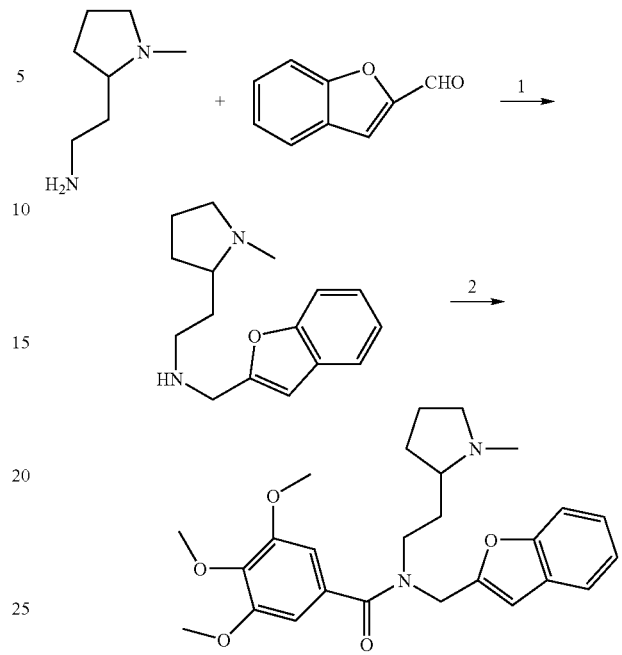

Step 1: Benzofuran-2ylmethyl-[2-(1-methyl-pyrrolidin-2-yl)-ethyl]-amine.

Experimental condition analogous to Example 5, from 2-benzofurancarboxaldehyde 0.14 g (1.1 mmol), 2-(1-methyl-pyrrolidin-2-yl)-ethylamine 0.14 g (1 mmol), and sodium triacethoxyborohydride 0.31 g (1.5 mmol), in 10 mL Dichloromethane. Purification using silica chromatography, elution with dichloromethane-methanol-ammonium hydroxide, 9-1-0.25, gave 83 mg of compound.

Step 2: N-Benzofuran-2-ylmethyl-3,4,5-trimethoxy-N-[2-(1-methyl-pyrrolidin-2-yl)-ethyl]-benzamide.

Experimental condition analogous to Example 1, from 3,4,5-trimethoxy benzoic acid 0.08 g (0.32 mmol), 1-ethyl-3-(3-dimethylaminopropyl) carbodiimide hydrochloride 0.060 g (0.38 mmol), 1-hydroxybenzotriazole 0.05 g (0.38 mmol), triethylamine 0.05 mL (0.38 mmol), and benzofuran-2ylmethyl-[2-(1-methyl-pyrrolidin-2-yl)-ethyl]-amine 0.08 g (0.3 mmol) in 3 mL tetrahydrofuran. Purification using reverse phase HPLC, C18 column with a gradient of 20-80% acetonitrile –0.1% TFA, gave 100 mg of white powder as a TFA salt. LC-MSD, m/z for: $C_{26}H_{32}N_2O_5$ [M+H]: 453.5. LC retention time on HPLC, C18 column gradient 20-95% acetonitrile with 0.1% TFA in 7 minutes: 2.73.

Example 8

This example illustrates the preparation of N-Benzo[b]thiophen-2-ylmethyl-3,4,5-trimethoxy-N-[2-(1-methyl-pyrrolidin-2-yl)-ethyl]-benzamide.

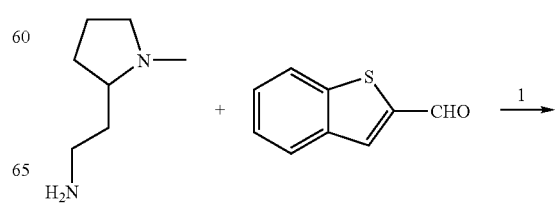

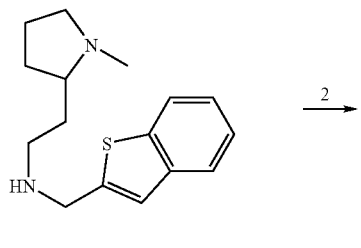

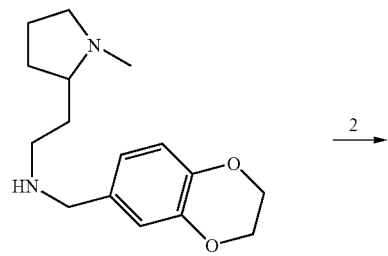

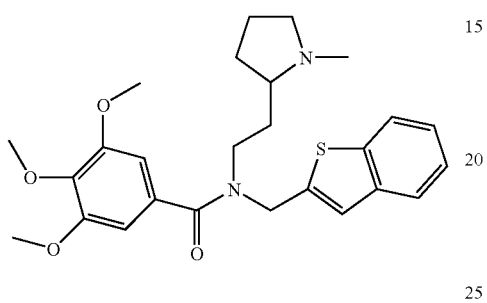

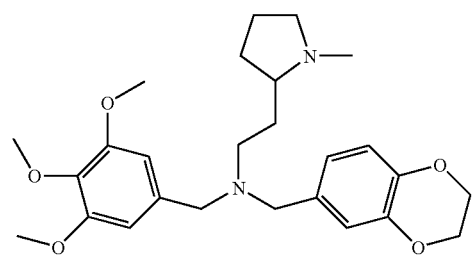

Step 1: Benzo[b]thiophen-2-ylmethyl-[2-(1-methyl-pyrrolidin-2-yl)-ethyl]-amine.

Experimental condition analogous to Example 5, from benzo[b]thiophen-2-carbaldehyde 0.18 g (1.1 mmol), 2-(1-methyl-pyrrolidin-2-yl)-ethylamine 0.14 g (1 mmol), and sodium triacethoxyborohydride 0.31 g (1.5 mmol), in 10 mL dichloromethane. Purification using silica gel chromatography, elution with dichloromethane-methanol-ammonium hydroxide, 9-1-0.25, gave 73 mg of compound.

Step 2: N-Benzo[b]thiophen-2-ylmethyl-3,4,5-trimethoxy-N-[2-(1-methyl-pyrrolidin-2-yl)-ethyl]-benzamide.

Experimental condition analogous to Example 1, from 3,4,5-dimethoxy benzoic acid 0.07 g (0.26 mmol), 1-ethyl-3-(3-dimethylaminopropyl) carbodiimide hydrochloride 0.05 g (0.31 mmol), 1-hydroxybenzotriazole 0.04 g (0.3 mmol), triethylamine 0.03 mL (0.31 mmol), and benzo[b]thiophen-2-ylmethyl-[2-(1-methyl-pyrrolidin-2-yl)-ethyl]-amine 0.07 g (0.26 mmol) in 3 mL tetrahydrofuran. Purification using reverse phase HPLC, C18 column with a gradient 20-80% acetonitrile −0.1% TFA, gave 50 mg of hydroscopic powder, as a TFA salt. LC-MSD, m/z for: $C_{26}H_{32}N_2O_4S$ [M+H]: 469.5. LC retention time on HPLC, C18 column gradient 20-95% acetonitrile with 0.1% TFA in 7 minutes: 2.858.

Example 9

This example illustrates the preparation of N-(2,3-Dihydro-benzo[1,4]dioxin-6-ylmethyl)-3,4,5-trimethoxy-N-[2-(1-methyl-pyrrolidin-2-yl)-ethyl]-benzamide.

Step 1: (2,3-Dihydro-benzo[1,4]dioxin-6-ylmethyl)-[2-(1-methyl-pyrrolidin-2-yl)-ethyl]-amine.

Experimental condition analogous to Example 5, from benzo[b]thiophen-2-carbaldehyde 0.18 g (1.1 mmol), 2-(1-methyl-pyrrolidin-2-yl)-ethylamine 0.14 g (1 mmol), and sodium triacethoxyborohydride 0.31 g (1.5 mmol), in 10 mL dichloromethane. Purification using silica gel chromatography, elution with dichloromethane-methanol-ammonium hydroxide, 9-1-0.25, gave 0.21 g of compound.

Step 2: (2,3-Dihydro-benzo[1,4]dioxin-6-ylmethyl)-[2-(1-methyl-pyrrolidin-2-yl)-ethyl]-amine.

Experimental condition analogous to Example 1, from 3,4,5-dimethoxy benzoic acid 0.19 g (0.91 mmol), 1-ethyl-3-(3-dimethylaminopropyl) carbodiimide hydrochloride 0.14 g (0.91 mmol), 1-hydroxybenzotriazole 0.12 g (0.91 mmol), triethylamine 0.12 mL (0.91 mmol), and (2,3-dihydro-benzo[1,4]dioxin-6-ylmethyl)-[2-(1-methyl-pyrrolidin-2-yl)-ethyl]-amine 0.21 g (0.76 mmol) in 5 mL tetrahydrofuran. Purification using reverse phase HPLC, C18 column with a gradient of 20-80% acetonitrile −0.1% TFA, gave 150 mg compound as a TFA salt. LC-MSD, m/z for: $C_{26}H_{34}N_2O_6$ [M+H]: 471.5. LC retention time on HPLC, C18 column gradient 20-95% acetonitrile with 0.1% TFA in 7 minutes: 1.805.

Example 10

This example illustrates the preparation of 3,4,5-Trimethoxy-N-[2-(1-methyl-pyrrolidin-2yl)-N-quinolin-3-yl-methyl-benzamide.

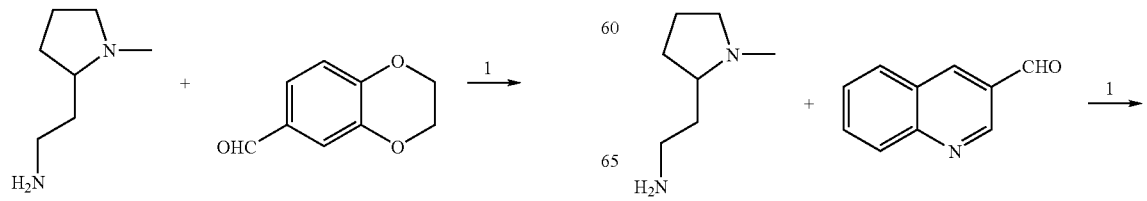

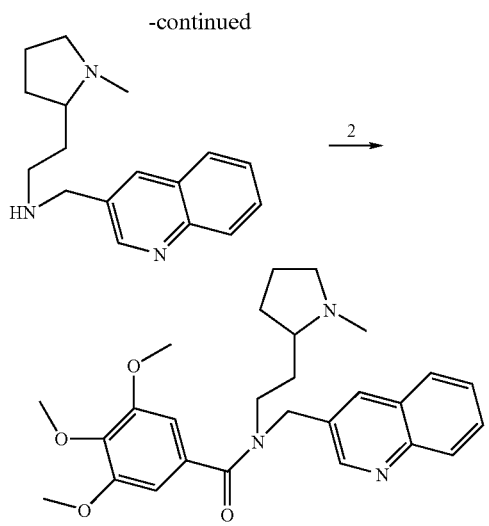

Step 1: [2-(1-Methyl-pyrrolidin-2-yl)-ethyl-quinolin-3-yl-methyl-amine.

Experimental condition analogous to Example 5, from quinoline-3-carbaldehyde 0.25 g (1.5 mmol), 2-(1-methyl-pyrrolidin-2-yl)-ethylamine 0.22 g (1.8 mmol), and sodium triacethoxyborohydride 0.31 g (1.5 mmol), in 10 mL dichloromethane. Purification using silica gel chromatography, elution with dichloromethane-methanol-ammonium hydroxide, 9-1-0.25, gave 160 mg of light yellow oily compound.

Step 2: 3,4,5-Trimethoxy-N-[2-(1-methyl-pyrrolidin-2yl)-N-quinolin-3-ylmethyl-benzamide.

Experimental condition analogous to Example 1, from 3,4,5-dimethoxy benzoic acid 0.11 g (0.55 mmol), 1-ethyl-3-(3-dimethylaminopropyl) carbodiimide hydrochloride 0.10 g (0.55 mmol), 1-hydroxybenzotriazole 0.05 g (0.40 mmol), triethylamine 0.08 mL (0.55 mmol), and [2-(1-Methyl-pyrrolidin-2-yl)-ethyl-quinolin-3-ylmethyl-amine 0.1 g (0.37 mmol) in 5 mL tetrahydrofuran. Purification using silica gel chromatography elution using dichloromethane-methanol: 9-1 gave 80 mg light yellow oil. LC-MSD, m/z for: $C_{27}H_{33}N_3O_4$ [M+H]: 464.5. LC retention time on HPLC, C18 column gradient 20-95% acetonitrile with 0.1% TFA in 7 minutes: 1.93 min.

Example 11

This example illustrates the preparation of 3,4,5-Trimethoxy-N-[2-(1-methyl-pyrrolidin-2yl)-N-quinolin-2-yl-methyl-benzamide.

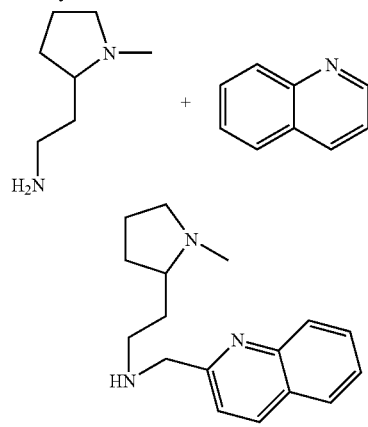

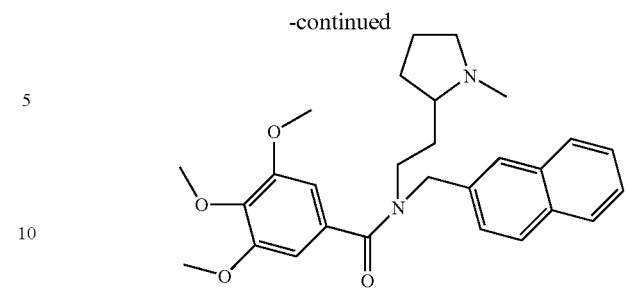

Step 1: [2-(1-Methyl-pyrrolidin-2-yl)-ethyl-quinolin-2-yl-methyl-amine.

Experimental condition analogous to Example 5, from quinoline-2-carbaldehyde 0.25 g (1.5 mmol), 2-(1-methyl-pyrrolidin-2-yl)-ethylamine 0.22 g (1.8 mmol), and sodium triacethoxyborohydride 0.31 g (1.5 mmol), in 10 mL dichloromethane. Purification using silica chromatography, elution with dichloromethane-methanol-ammonium hydroxide, 9-1-0.25, gave 0.24 g of dark orange oily compound.

Step 2: 3,4,5-Trimethoxy-N-[2-(1-methyl-pyrrolidin-2yl)-N-quinolin-2-ylmethyl-benzamide.

Experimental condition analogous to Example 1, from 3,4,5-dimethoxy benzoic acid 0.11 g (0.55 mmol), 1-ethyl-3-(3-dimethylaminopropyl) carbodiimide hydrochloride 0.10 g (0.55 mmol), 1-hydroxybenzotriazole 0.05 g (0.40 mmol), triethylamine 0.08 mL (0.55 mmol), and [2-(1-methyl-pyrrolidin-2-yl)-ethyl-quinolin-2-ylmethyl-amine 0.1 g (0.37 mmol) in 5 mL tetrahydrofuran. Purification using silica gel chromatography elution using dichloromethane-methanol: 9-1 gave 50 mg light yellow oil. LC-MSD, m/z for $C_{27}H_{33}N_3O_4$ [M+H]: 464.5. LC retention time on HPLC, C18 column gradient 20-95% acetonitrile with 0.1% TFA in 7 minutes: 0.81.

Example 12

This example illustrates the preparation of N-Benzo[b]thiophen-3-ylmethyl-3,4,5-trimethoxy-N-[2-(1-methyl-pyrrolidin-2-yl)-ethyl]-benzamide.

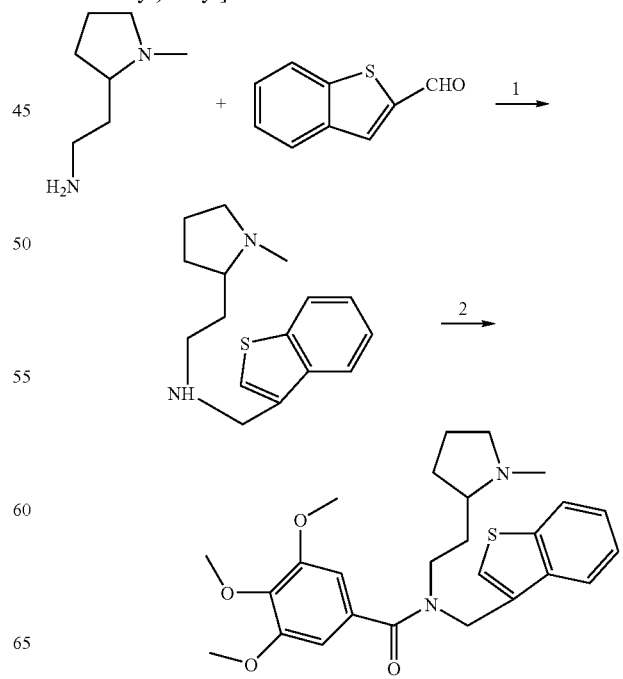

Step 1: Benzo[b]thiophen-3-ylmethyl-[2-(1-methyl-pyrrolidin-2-yl)-ethyl]-amine.

Experimental condition analogous to Example 5, from benzo[b]thiophen-3-carbaldehyde 0.16 g (1 mmol), 2-(1-methyl-pyrrolidin-2-yl)-ethylamine 0.14 g (1.1 mmol), and sodium triacethoxyborohydride 0.31 g (1.5 mmol), in 10 mL Dichloromethane. Purification using silica chromatography, elution with dichloromethane-methanol-ammonium hydroxide, 9-1-0.25, gave 140 mg of compound.

Step 2: N-Benzo[b]thiophen-3-ylmethyl-3,4,5-trimethoxy-N-[2-(1-methyl-pyrrolidin-2-yl)-ethyl]-benzamide.

Experimental condition analogous to Example 1, from 3,4,5-dimethoxy benzoic acid 0.13 g (0.62 mmol), 1-ethyl-3-(3-dimethylaminopropyl) carbodiimide hydrochloride 0.09 g (0.62 mmol), 1-hydroxybenzotriazole 0.08 g (0.62 mmol), triethylamine 0.08 mL (0.62 mmol), and benzo[b]thiophen-2-ylmethyl-[2-(1-methyl-pyrrolidin-2-yl)-ethyl]-amine 0.14 g (0.51 mmol) in 3 mL tetrahydrofuran. Purification using reverse phase HPLC C18 column with a gradient of 20-80% acetonitrile –0.1% TFA, gave 120 mg of hydroscopic powder, as a TFA salt. LC-MSD, m/z for: $C_{26}H_{32}N_2O_4S$ [M+H]: 469.5. LC retention time on HPLC, C18 column gradient 20-95% acetonitrile with 0.1% TFA in 7 minutes: 3.07 min.

Example 13

This example illustrates the preparation of N-Benzothiazol-2-ylmethyl-3,4,5-trimethoxy-N-[2-(1-methyl-pyrrolidin-2-yl)-ethyl]-benzamide.

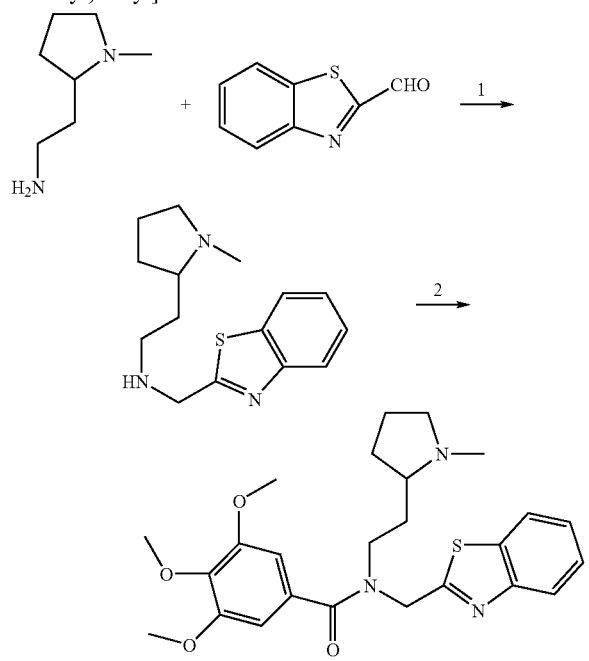

Step 1: Benzo[thiazol-2-ylmethyl-[2-(1-methyl-pyrrolidin-2-yl)-ethyl]-amine.

Experimental condition analogous to Example 5, from benzothiazol-2-carbaldehyde 0.16 g (1 mmol), 2-(1-methyl-pyrrolidin-2-yl)-ethylamine 0.14 g (1.1 mmol), and sodium triacethoxyborohydride 0.31 g (1.5 mmol), in 10 mL dichloromethane. Purification using silica gel chromatography, elution with dichloromethane-methanol-ammonium hydroxide, 9-1-0.25, gave 0.15 mg of compound.

Step 2: N-Benzotriazol-2-ylmethyl-3,4,5-trimethoxy-N-[2-(1-methyl-pyrrolidin-2-yl)-ethyl]-benzamide.

Experimental condition analogous to Example 1, from 3,4,5-dimethoxy benzoic acid 0.14 g (0.65 mmol), 1-ethyl-3-(3-dimethylaminopropyl) carbodiimide hydrochloride 0.1 g (0.65 mmol), 1-hydroxybenzotriazole 0.08 g (0.65 mmol), triethylamine 0.09 mL (0.65 mmol), and benzotriazole-2-ylmethyl-[2-(1-methyl-pyrrolidin-2-yl)-ethyl]-amine 0.15 g (0.54 mmol) in 3 mL tetrahydrofuran. Purification using reverse phase HPLC, C18 column gradient of 20-80% acetonitrile –0.1% TFA, gave 120 mg of hydroscopic powder, as a TFA salt. LC-MSD, m/z for: $C_{25}H_{31}N_3O_4S$ [M+H]: 470.5. LC retention time on HPLC, C18 column gradient 20-95% acetonitrile with 0.1% TFA in 7 minutes: 2.50.

Example 14

This example illustrates the preparation of 3,4,5-Trimethoxy-N-(1-methyl-1H-benzoimidazol-2-ylmethyl)-N-[2-(1-methyl-pyrrolidin-2-yl)-ethyl]-benzamide.

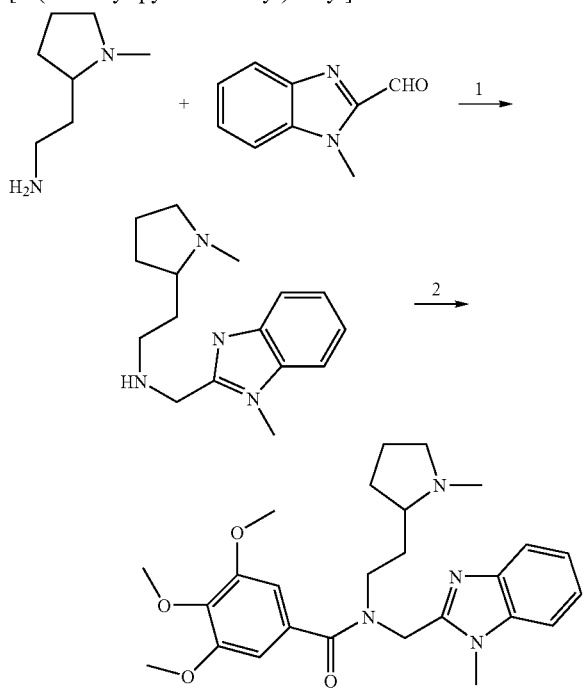

Step 1: (1-Methyl-1H-benzoimidazol-2-ylmethyl)-[2-(1-methyl-pyrrolidin-2-yl)-ethyl]-amine.

Experimental condition analogous to Example 5, from 1-methyl-1H-benzoimidazol-2-carbaldehyde 0.2 g (1.25 mmol), 2-(1-methyl-pyrrolidin-2-yl)-ethylamine 0.18 g (1.38 mmol), and sodium triacethoxyborohydride 0.39 g (1.87 mmol), in 10 mL dichloromethane. After work-up the material was used as a crude.

Step 2: 3,4,5-Trimethoxy-N-(1-methyl-1H-indol-2-ylmethyl)-N-[2-(1-methyl-pyrrolidin-2-yl)-ethyl]-benzamide.

Experimental condition analogous to Example 5, from (1-methyl-1H-benzoimidazol-2-ylmethyl)-[2-(1-methyl-pyrrolidin-2-yl)-ethyl]-amine the crude, 3,4,5-trimethoxy-benzoylchloride 0.37 g (1.62 mmol), and triethylamine 0.26 mL (1.87 mmol), in 5 mL of anhydrous dichloromethane. The compound was purified using reverse phase HPLC, C18 column with a gradient of 20-80% acetonitrile-0.1% TFA, yield to 110 mg of pure material. LC-MSD, m/z for: $C_{26}H_{34}N_4O_4$ [M+H]: 467.2. LC retention time on HPLC, C18 column gradient 20-95% acetonitrile with 0.1% TFA in 7 minutes: 0.43 min.

Example 15

This example illustrates the preparation of N-(1H-Indol-2ylmethyl)-3,4,5-trimethoxy-N-[2-(1-methyl-pyrrolidin-2-yl)-ethyl]-benzamide.

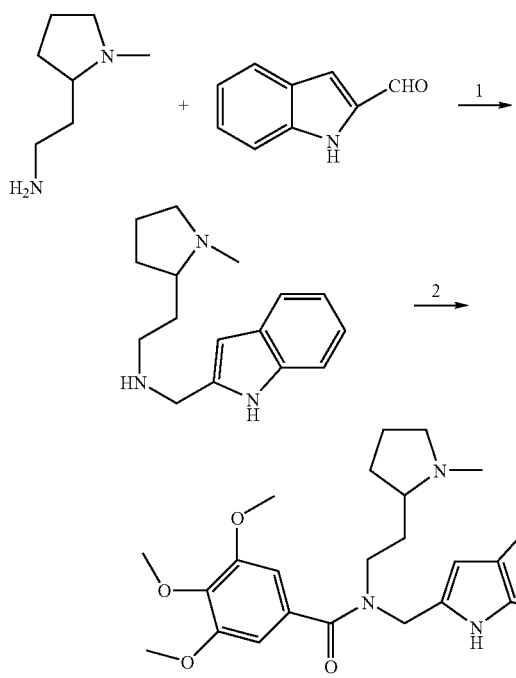

Step 1: (1H-Indol-2ylmethyl)-[2-(1-methyl-pyrrolidin-2-yl)-ethyl]-amine.

Experimental condition analogous to Example 5, from 1H-indole-2-carbaldehyde 0.14 g (2 mmol), 2-(1-methyl-pyrrolidin-2-yl)-ethylamine 0.3 g (2.4 mmol), and sodium triacethoxyborohydride 0.87 g (1.87 mmol), in 20 mL Dichloromethane. The compound was purified using silica gel chromatography elution, ethyl-acetate-methanol-amonium hydroxide: 9-1-0.1 to 8-2-0.2, yield to 0.3 g light brown oil.

Step 2: N-(1H-Indol-2ylmethyl)-3,4,5-trimethoxy-N-[2-(1-methyl-pyrrolidin-2-yl)-ethyl]-benzamide Experimental condition analogous to Example 5, from (1H-indol-2ylmethyl)-[2-(1-methyl-pyrrolidin-2-yl)-ethyl]-amine 0.8 g (0.31 mmol), 3,4,5-trimethoxy-benzoylchloride 0.08 g (0.34 mmol), and triethylamine 0.06 mL (0.46 mmol), in 5 mL of anhydrous dichloromethane. The compound was purified using reverse phase HPLC, C 18 column with a gradient of 20-70% acetonitrile-0.1% TFA, yield to 50 mg of pure material. LC-MSD, m/z for: $C_{26}H_{33}N_3O_4$ [M+H]: 452.2. LC retention time on HPLC, C18 column gradient 20-95% acetonitrile with 0.1% TFA in 7 minutes: 1.99 min.

Example 16

This example illustrates the preparation of N-(1H-Indol-2ylmethyl)-3,5-dimethoxy-N-[2-(1-methyl-pyrrolidin-2-yl)-ethyl]-benzamide.

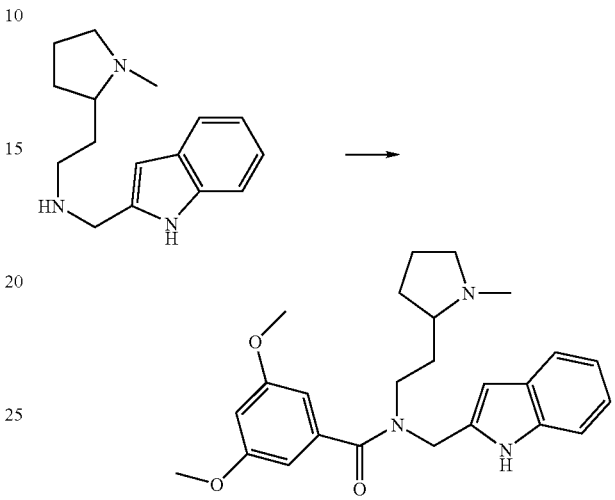

Experimental condition analogous to Example 5, from (1H-indol-2ylmethyl)-[2-(1-methyl-pyrrolidin-2-yl)-ethyl]-amine 0.1 g (0.38 mmol), 3,5-dimethoxy-benzoylchloride 0.08 g (0.42 mmol), and triethylamine 0.08 mL (0.57 mmol), in 1.5 mL of anhydrous dichloromethane. The compound was purified using reverse phase HPLC, C18 column with a gradient of 20-70% acetonitrile-0.1% TFA, yield to 50 mg of pure material. LC-MSD, m/z for: $C_{25}H_{31}N_3O_3$ [M+H]: 422.2. LC retention time on HPLC, C18 column gradient 20-95% acetonitrile with 0.1% TFA in 7 minutes: 2.7 min.

Example 17

This example illustrates the preparation of N-Biphenyl-3-yl-3,4,5-trimethoxy-N-[3-(2-methyl-piperidin-1-yl)-propyl]-benzamide.

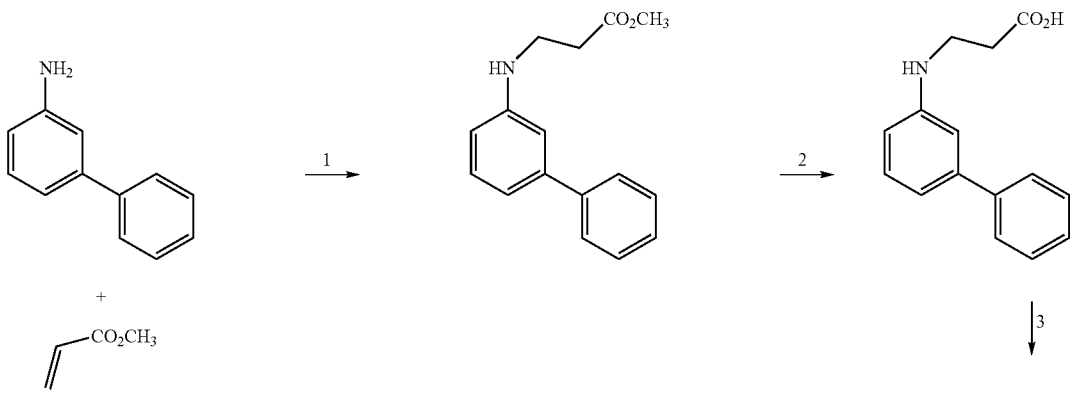

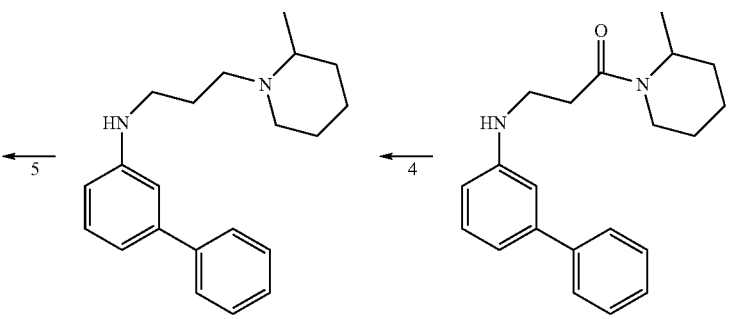

Step 1: 3-(Biphenyl-3-ylamino)-propionic acid methyl ester.

In a round bottom flask was added 3-aminobiphenyl 2.6 g (15.3 mmol), methyl acrylate 1.5 g (16.9 mmol) and cupric acetate 0.1 g, the reaction mixture was stirred 5 hour at 90° C., another 5 equivalent of methyl acrylate 7 g (75 mmol), and 0.25 g of cupric acetate was added, and the reaction mixture was heated for another 5 hours. The crude was purified using silica gel chromatography using 15% of ethyl acetate and petroleum ether. Yield to 1.6 g of oil.

Step 2: 3-(Biphenyl-3-ylamino)-propionic acid.

3-(Biphenyl-3-ylamino)-propionic acid methyl ester 1.6 g (6.3 mmol) was taken in 8 mL of water and 8 mL of tetrahydrofuran, to this solution was added 0.4 g (9.5 mmol) of lithium hydroxide, reaction stirred at room temperature for 5 hour. The solvent was removed from the mixture completely and 10 mL water was added and washed with ethyl acetate. The aqueous solution was acidified with 1 M HCl, and was extracted with ethyl acetate 3 times. Combined organic layer was washed with brine, dried over magnesium sulfate and concentrated under vaccum, yield to 1.6 g of acid used as crude for the next step.

Step 3: 3-(Biphenyl-3-ylamino)-1-(2-methyl-piperidin-1-yl)-propan-1-one.

To a mixture of the 3-(biphenyl-3-ylamino)-propionic acid 1.6 g (6.6 mmol), 2-methylpiperidine 0.78 g (7.9 mmol), was added the solid O-(benzotriazole-1-yl)-N,N,N',N'-tetramethyluronium tetrafluoroborate 4.7 g (1.3 mmol), and triethylamine 3.86 mL (27 mmol) in 25 mL of dichloromethane and left overnight at room temperature. The reaction mixture was washed with water, the organic layer, dried over magnesium sulfate, filtered, and concentrated under vacuum. The compound was purified using silica gel chromatography and was eluted with ethyl acetate, yield to 2 g material.

Step 4: Biphenyl-3-yl-[3-(2-methyl-piperdin-1-yl)-propyl]-amine.

3-(Biphenyl-3-ylamino)-1-(2-methyl-piperidin-1-yl)-propan-1-one 1 g (3.1 mmol) in 10 mL of tetrahydrofuran was added dropwise to a cold solution of lithium aluminium hydride 0.1 g (3.1 mmol) in 10 mL dry tetrahydrofuran. The mixture was stirred for 5 hour then was quenched with saturated solution of sodium sulfate. The compound was purified by silica gel chromatography using chloroform-methanol 9:1, yield to 0.2 g of compound.

Step 5: N-Biphenyl-3-yl-3,4,5-trimethoxy-N-[3-(2-methyl-piperidin-1-yl)-propyl]-benzamide.

3,4,5-trimethoxy benzoic acid 0.19 g (0.89 mmol) was dissolved in thionyl chloride 0.26 mL (3.5 mmol) and refluxed for 3 hours under a guard tube. The excess of thionyl chloride was removed under vacuum. Biphenyl-3-yl-[3-(2-methyl-piperdin-1-yl)-propyl]-amine 0.23 g (0.746 mmol) was taken in 5 mL dichloromethane, triethylamine 4.1 mL (3 mmol) was then added, the mixture was then cooled and acid chloride in 5 mL dichloromethane was added dropwise and was stirred overnight. The solvent was removed under vacuum and the compound was purified by silica gel chromatography using chloroform-methanol 9-1, gave 40 mg of compound. LC-MSD, m/z for: $C_{31}H_{38}N_2O_4$ [M+H]: 503.6. LC retention time on HPLC, C18 column gradient 20-95% acetonitrile with 0.1% TFA in 7 minutes: 3.96.

Example 18

This example illustrates the preparation of 3,4,5-Trimethoxy-N-[3-(2-methyl-piperidin-1-yl)-N-naphthalen-2-ylmethyl-benzamide.

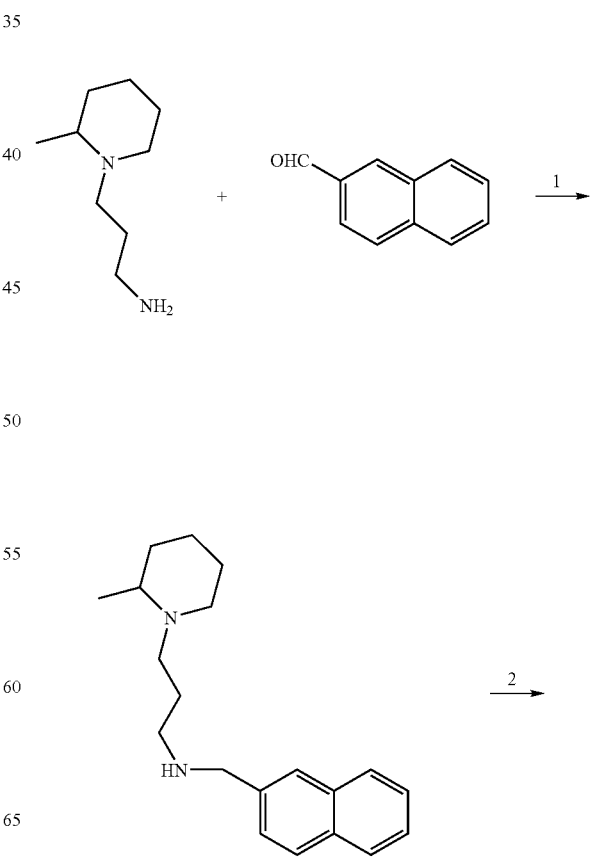

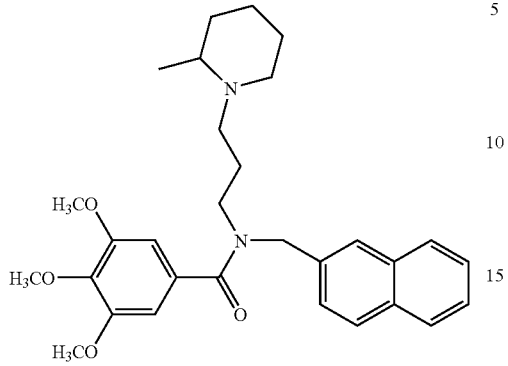

Step 1: [3-(2-Methyl-piperidin-1-yl)-propyl]-naphthalen-2-ylmethyl-amine.

2-Naphtaldehyde 1 g (6.4 mmol), 3-(2-methyl-piperidin-1-yl)-propylamine 0.99 g (6.4 mmol), in 25 mL of dry dichloromethane was added 5 g of molecular sieve. The reaction was stirred overnight at room temperature. The molecular sieve was filtered and dichloromethane was concentrated under vacuum. To the mixture was added 15 mL of dry methanol and sodium borohydride 0.3 g (8 mmol) after 30 minutes reaction goes to completion, methanol was concentrated under vacuum, and was diluted with chloroform, organic layer was washed with 2 times 20 mL water, followed with brine. The organic layer was dried over magnesium sulfate and concentrated under vacuum. The compound was purified using silica gel chromatography elution, with 3.5% methanol in chloroform, yield 0.6 g oil.

Step 2: 3,4,5-Trimethoxy-N-[3-(2-methyl-piperidin-1-yl)-N-naphthalen-2-ylmethyl-benzamide.

[3-(2-Methyl-piperidin-1-yl)-propyl]-naphthalen-2-ylmethyl-amine 0.55 g (1.8 mmol), 3,4,5-trimethoxy-benzoic acid 0.04 g (2.2 mmol), triethylamine 0.02 mL and O-(benzotriazol-1-yl)-N,N,N',N'-tetramethyluronium tetrafluoroborate 0.18 g (3.6 mmol), 5 mL of anhydrous dichloromethane. The compound was purified using 2% methanol in chloroform. LC-MSD, m/z for: $C_{30}H_{38}N_2O_4$ [M+H]: 491.6. LC retention time on HPLC, C18 column gradient 20-95% acetonitrile with 0.1% TFA in 7 minutes: 3.86 min.

Example 19

This example illustrates the preparation of 3,4,5-Trimethoxy-N-[3-(2-methyl-piperidin-1-yl)-propyl]-N-(5-phenyl-thiazol-2-ylmethyl)-benzamide.

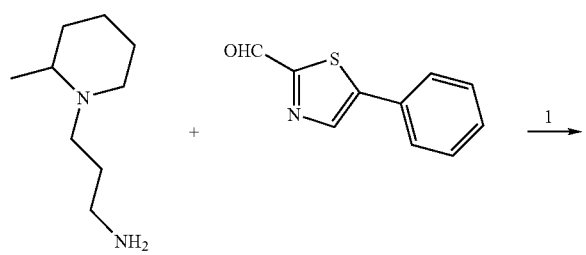

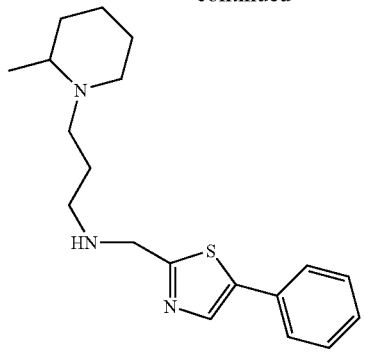

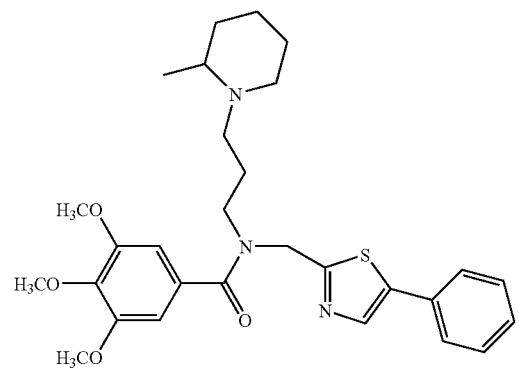

Step 1: [3-(2-Methyl-piperidin-1-yl)-propyl]-(5-phenyl-thiazol-2ylmethyl)-amine.

Experimental condition analogous to Example 18, from 5-phenyl-thiazole-2-carbaldehyde 0.16 g (1.05 mmol), 3-(2-methyl-piperidin-1-yl)-propylamine 0.2 g (1.05 mmol), in 5 mL of dry dichloromethane was added 2 g of molecular sieve. The reaction was stirred overnight at room temperature. The molecular sieve was filtered and dichloromethane was concentrated under vaccum. To the mixture was added 15 mL of dry methanol and sodium borohydride 0.04 g (1.155 mmol) was added at 0° C. after 30 minutes reaction goes to completion. The reaction was quenched with 2 mL acetone, methanol was concentrated under vacuum, and was diluted with chloroform, organic layer was washed with 2 times 20 mL water, followed with brine. The organic layer was dried over magnesium sulfate and concentrated under vaccum. Yield 0.3 g of compound.

Step 2: 3,4,5-Trimethoxy-N-[3-(2-methyl-piperidin-1-yl)-propyl]-N-(5-phenyl-thiazol-2-ylmethyl)-benzamide.

Experimental condition analogous to Example 18, from [3-(2-methyl-piperidin-1-yl)-propyl]-(5-phenyl-thiazol-2ylmethyl)-amine 0.15 g (0.45 mmol), 3,4,5-trimethoxy-benzoic acid 0.10 g (0.499 mmol), triethylamine 0.15 mL and 1-propanephosphonic acid cyclic anhydride (50% in ethyl acetate) 0.34 g (0.54 mmol) 20 mL of ethyl acetate. The compound was purified using neutral alumina gel chromatography elution with chloroform, gave 120 mg of material. LC-MSD, m/z for: $C_{29}H_{37}N_3O_4S$ [M+H]: 524.6. LC retention time on HPLC, C18 column gradient 20-95% acetonitrile with 0.1% TFA in 7 minutes: 3.54.

Example 20

This example illustrates the preparation of 3,4,5-Trimethoxy-N-[3-(2-methyl-piperidin-1-yl)-propyl]-N-naphthalen-2-yl-benzamide.

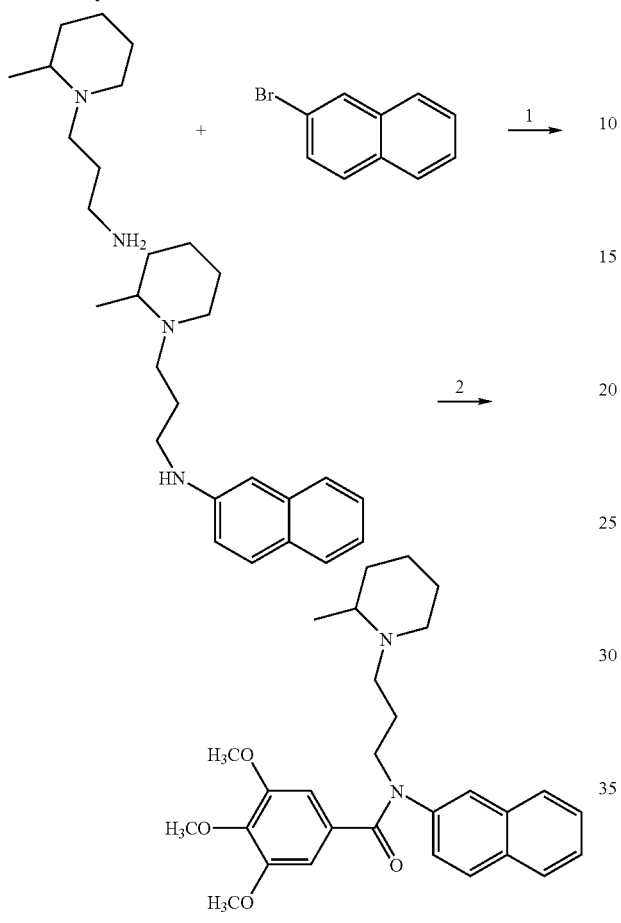

Step 1: [3-(2-Methyl-piperidin-1-yl)-propyl]-naphthalen-2-yl amine.

In round bottom flask under nitrogen, was added palladium (II) acetate 0.09 g (0.4 mmol), rac-2,2'-bis(diphenylphosphino)-1,1'-binaphtyl 0.53 g (0.8 mmol), tripotassium phospate mono basic 0.06 g (29 mmol), in 25 mL DME, to this mixture was added 2-bromonaphthalene 1.7 g (8.2 mmol), and 2-methyl-piperidine-N-propylamine 4 g (25.6 mmol). The mixture was refluxed 17 hours. The reaction mixture was filtered through celite and concentrated. The compound was purified using silica gel chromatography, elution with 5% methanol in chloroform. Yield to 0.47 g of compound.

Step 2: 3,4,5-Trimethoxy-N-[3-(2-methyl-piperidin-1-yl)-propyl]-N-naphthalen-2-yl-benzamide.

Experimental condition analogous to Example 18 from, 3,4,5 trimethoxybenzoic acid 0.53 g (2.5 mmol), thionyl chloride 0.24 mL (3.34 mmol), triethylamine 0.7 mL (5 mmol) and [3-(2-methyl-piperidin-1-yl)-propyl]-naphthalen-2-yl amine 0.47 g (1.67 mmol) in 15 mL chloroform. The compound was purified using silica gel chromatography gave 150 mg of material. LC-MSD, m/z for: $C_{29}H_{36}N_2O_4$ [M+H]: 477.5. LC retention time on HPLC, C18 column gradient 20-95% acetonitrile with 0.1% TFA in 7 minutes: 3.49.

Example 21

This example illustrates the preparation of 3,4-Dimethoxy-(S)—N-pyrrolidin-2ylmethyl-N-(1-styryl-propenyl)-benzamide

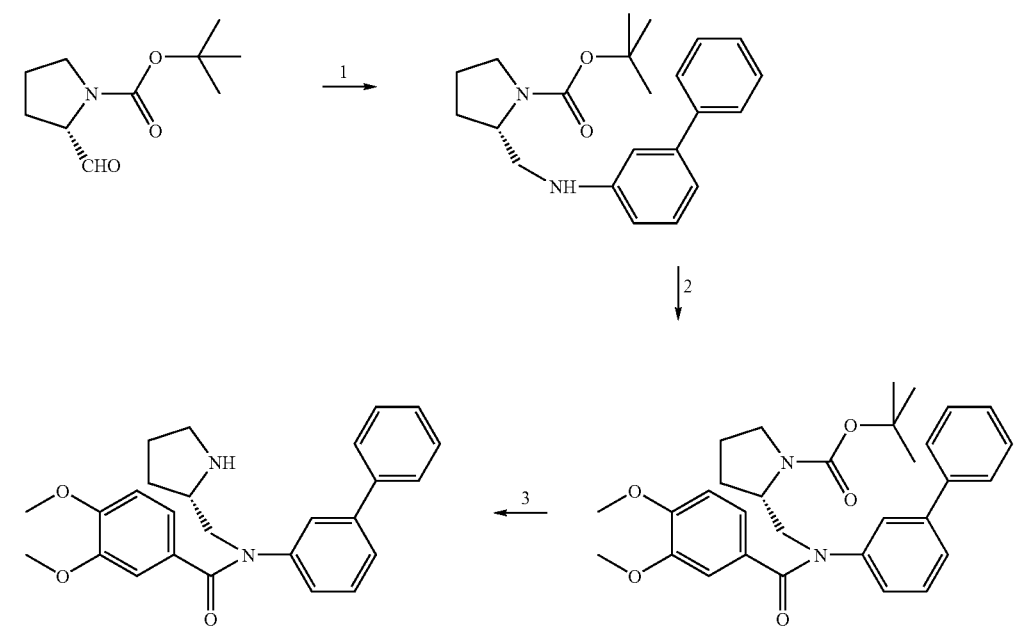

Step 1: 2-(S)-(Biphenyl-3-ylaminomethyl)-pyrrolidine-1-carboxylic acid tert-butyl ester. In 40 ml of methanol was dissolved 1.18 g (5.91 mmol) of (S)-2-formyl-pyrrolidine-1-carboxylic acid tert-butyl ester, and 1 g (5.91 mmol) of biphenyl-3-ylamine, to this mixture was added 3.7 g (17.73 mmol) of sodium triacethoxy borohydride, stirred at room temperature overnight. LC-MS showed 40% reaction, to this mixture was added 1.117 g (17.73 mmo) of sodiumcyanoborohydride, reaction was completed in 1 hour. Methanol was removed under vacuum, ethyl acetate was added to the mixture and washed 2 times with saturated sodium bicarbonate. Organic layer was dried over magnesium sulfate, filtrated and concentrated under vacuum, gave 1.93 g yellow viscous oil. LC-MSD, m/z for: $C_{22}H_{28}N_2O_2$ [M+H]: 353.5. LC retention time on HPLC, C18 column gradient 20-95% acetonitrile with 0.1% TFA in 7 minutes: 5.482.

Step 2: 2-(S)-{[Biphenyl-3-yl-(3,4-dimethoxy-benzoyl)-amino]-methyl}-pyrrolidine-1-carboxylic acid tert-butyl ester: Experimental condition analogous to Example 4, from 2-(S)-(biphenyl-3-ylaminomethyl)-pyrrolidine-1-carboxylic acid tert-butyl ester 1 g (2.84 mmol), 3,4-dimethoxy-benzoyl chloride 0.6 g (2.98 mmol), and triethylamine 0.43 g (4.26 mmol), and 25 mL of dichloromethane. After purification on silica using gradient of chloroform-ethylacetate (20-1 to 10-1) gave 1 g of white semi solid compound: LC-MSD, m/z for: $C_{31}H_{36}N_2O_5$ [M+H]: 517.6. LC retention time on HPLC, C18 column gradient 20-95% acetonitrile with 0.1% TFA in 7 minutes: 5.093

Step 3: 3,4-Dimethoxy-(S)—N-pyrrolidin-2ylmethyl-N-(1-styryl-propenyl)-benzamide: Experimental condition analogous to Example 1, from 1 g (1.94 mmol) of 2-(S)-{[Biphenyl-3-yl-(3,4-dimethoxy-benzoyl)-amino]-methyl}-pyrrolidine-1-carboxylic acid tert-butyl ester, 25 mL of trifluoroacetic acid and 100 mL of dichloromethane, gave 0.75 gram of white semi solid: LC-MSD, m/z for: $C_{26}H_{28}N_2O_3$ [M+H]: 417.6. LC retention time on HPLC, C18 column gradient 20-95% acetonitrile with 0.1% TFA in 7 minutes: 3.142; $^1$H NMR (400 MHz, $CDCl_3$/HCl): δ 1.5-2 (m, 6 H), 2.8-2.9 (m, 1 H), 3-3.1 (m, 1 H), 3.4-3.1 (m, 1 H), 3.6 (s, 3 H), 3.8 (s, 3 H), 3.9-4.1 (m, 1 H), 6.6 (d, 1 H), 6.8-7 (m, 2 H), 7.1 (m, 1 H), 7.2-7.4 (m, 8 H)

Example 22

This example illustrates the preparation of N-Biphenyl-3-yl-(S)—N[1-(2-hydroxy-ethyl)-pyrrolidin-2ylmethyl]-3,4-dimethoxy-benzamide

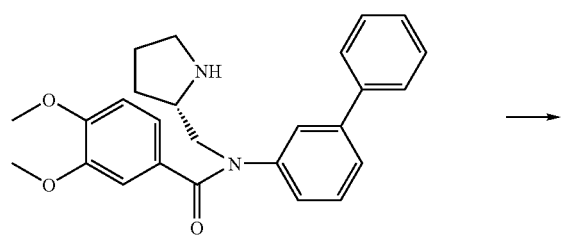

-continued

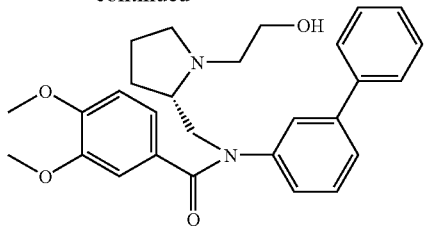

3,4-Dimethoxy-(S)—N-pyrrolidin-2ylmethyl-N-(1-styryl-propenyl)-benzamide 0.23 g (0.553 mmol) was dissolved in 5 mL of acetonitrile, 0.076 g (0.6 mmol) 2-bromo-ethanol was added, followed by 0.214 g (1.65 mmol) diisopropylethylamine. The reaction was heated at 45° C. overnight, reaction not complete stirred at 60° C. for overnight. Residue was taken in ethyl acetate and washed 2 times with saturated sodium bicarbonate. Organic layer dried over magnesium sulfate, and concentrated under vacuum, purification on silica gel, elution with chloroform methanol 30:1 gave 153 mg of a compound.: LC-MSD, m/z for: $C_{28}H_{32}N_2O_3$ [M+H]: 461.5. LC retention time on HPLC, C18 column gradient 20-95% acetonitrile with 0.1% TFA in 7 minutes: 3.067; $^1$H NMR (400 MHz, $CDCl_3$/HCl): δ 1.5-1.9 (m, 5 H), 2.2-2.3 (m, 1 H), 2.4-2.6 (m, 1 H), 3-3.2 (m, 3 H), 3.5-3.6 (m, 2 H), 3.6 (s, 3H), 3.8 (s, 3 H), 3.9-3.95 (m, 1 H), 4.2 (m, 1 H), 6.6 (d, 1 H), 6.8-7 (m, 2 H), 7.1 (m, 1 H), 7.2-7.4 (m, 8 H).

Example 23

This example illustrates the preparation of N-Biphenyl-3-yl-(S)—N-(1-isopropyl-pyrrolidin-2-ylmethyl)-3,4-dimethoxy-benzamide.

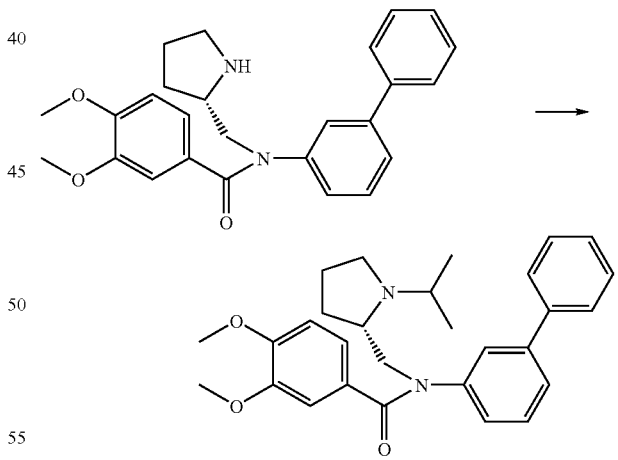

In a mixture of 1:1 acetone and methanol 5 mL, was dissolved 0.23 g (0.55 mmol) 3,4-dimethoxy-(S)—N-pyrrolidin-2ylmethyl-N-(1-styryl-propenyl)-benzamide, after 20 minutes, sodium cyanoborohydride 0.1 g (1.66 mmol) was added. The mixture was stirred at room temperature 1 hour, solvent was removed under vacuum, taken up in ethyl acetate and washed with saturated sodium bicarbonate, dried over magnesium sulfate, filtered and concentrated under vacuum. The residue was purified on silica with chloroform-methanol, 30:1 gave 0.21 g of compound. LC-MSD, m/z for:

$C_{29}H_{34}N_2O_3$ [M+H]: 459.5. LC retention time on HPLC, C18 column gradient 20-95% acetonitrile with 0.1% TFA in 7 minutes: 3.62;

$^1$H NMR (400 MHz, CDCl$_3$/HCl): δ 1.0 (d, 3 H), 1.1 (d, 3 H), 1.5-1.7 (m, 5 H), 2.5 (m, 1 H), 2.9-3.0 (m, 2 H), 3.2-3.3 (m, 1 H), 3.61 (s, 3 H), 3.8 (s, 3H), 3.9-3.95 (m, 1 H), 4.0 (m, 1H), 6.6 (d, 1 H), 6.8-7 (m, 2 H), 7.1 (m, 1 H), 7.2-7.4 (m, 8 H).

Example 24

This example illustrates the preparation of N-biphenyl-3-yl-(S)—N-(1-cyclohexylmethyl-pyrrolidin-2-ylmethyl)-3,4-dimethoxy-benzamide.

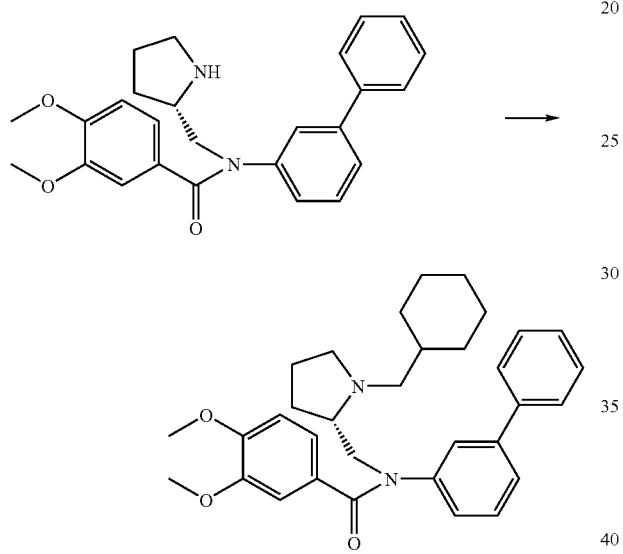

Experimental condition analogous to Example 23 from 0.2 g (0.48 mmol) 3,4-dimethoxy-(S)—N-pyrrolidin-2ylmethyl-N-(1-styryl-propenyl)-benzamide, 54 mg (0.48 mmol) of cyclohexanecarbaldehyde, and 90 mg (1.44 mmol) of sodium cyanoborohydride, in 5 mL methanol. Purification on silica gel and elution with chloroform-methanol 30:1 gave 175 mg of compound: LC-MSD, m/z for: $C_{33}H_{40}N_2O_3$ [M+H]: 513.6. LC retention time on HPLC, C18 column gradient 20-95% acetonitrile with 0.1% TFA in 7 minutes: 4.533.

Example 25

This example illustrates the preparation of N-Benzothiazol-2-yl methyl-3,4 dimethoxy-N—(S)-pyrrolidin-2-ylmethyl-benzamide.

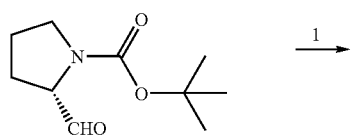

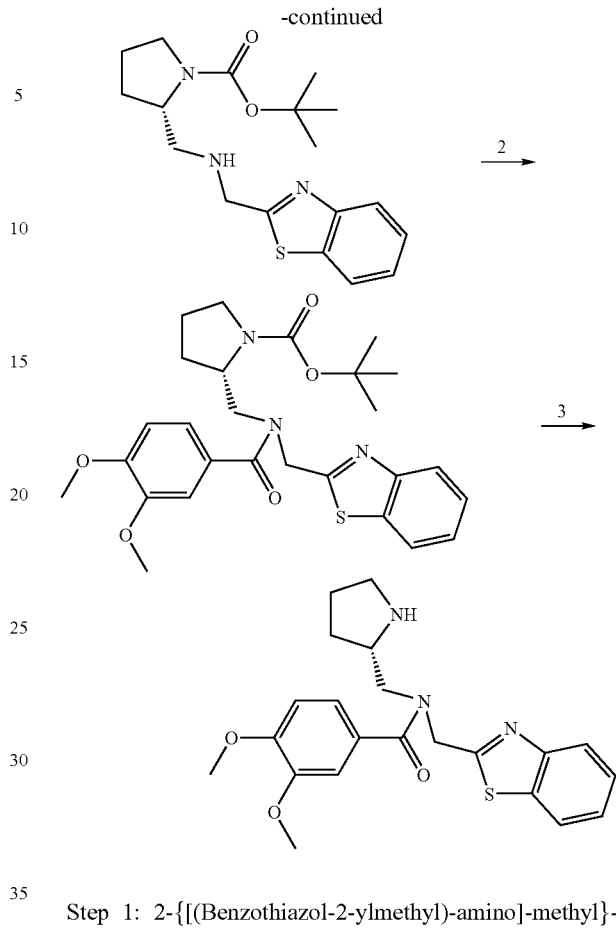

Step 1: 2-{[(Benzothiazol-2-ylmethyl)-amino]-methyl}-(S)-pyrrolidine-1-carboxylic acid tert-butyl ester. Experimental condition analogous to Example 24, from (S)-2-formyl-pyrrolidine-1-carboxylic acid tert-butyl ester 0.5 g (2.49 mmol), 0.5 g (0.26 mmol) C-benzothiazol-2-yl-methylamine and 0.46 g (7.47 mmol) of sodiumcyanoborohydride in 10 mL of methanol, gave 861 mg of oil: LC-MSD, m/z for: $C_{18}H_{25}N_3O_2S$ [M+H]: 348.4. LC retention time on HPLC, C18 column gradient 20-95% acetonitrile with 0.1% TFA in 7 minutes: 2.81.

Step 2: 2-{[Benzothiazol-2-ylmethyl-(3,4-dimethoxy-benzoyl)-amino]-methyl}-(S)-pyrrolidine-1-carboxylic acid tert-butyl ester. Experimental condition analogous to Example 21, from 0.86 g (2.48 mmol) of 2-{[(benzothiazol-2-ylmethyl)-amino]-methyl}-(S)-pyrrolidine-1-carboxylic acid tert-butyl ester, 0.52 g (2.60 mmol) of 3,4-benzoyl-chloride, and 0.50 g (4.96 mmol) triethylamine, in 20 mL dichloromethane, gave 1.21 g pale orange foam: LC-MSD, m/z for: $C_{27}H_{33}N_3O_5S$ [M+H]: 512.5. LC retention time on HPLC, C18 column gradient 20-95% acetonitrile with 0.1% TFA in 7 minutes: 4.534.

Step 3: N-Benzothiazol-2-yl methyl-3,4 dimethoxy-N—(S)-pyrrolidin-2-ylmethyl-benzamide. Experimental condition analogous to Example 21, from 1.21 g (2.37 mmol) of 2-{[benzothiazol-2-ylmethyl-(3,4-dimethoxy-benzoyl)-amino]-methyl}-(S)-pyrrolidine-1-carboxylic acid tert-butyl ester, 15 mL of trifluoroacetic acid and 60 mL of dichloromethane, gave 740 mg of white semi solid compound: LC-MSD, m/z for: $C_{22}H_{25}N_3O_3S$ [M+H]: 412.2. LC retention time on HPLC, C18 column gradient 20-95% acetonitrile with 0.1% TFA in 7 minutes: 0.471.

Example 26

This example illustrates the preparation of N-Benzothiazol-2-yl methyl-(S)—N-[1-(2-hydroxy-ethyl)-pyrrolidin-2-ylmethyl]-3,4-dimethoxy-benzamide.

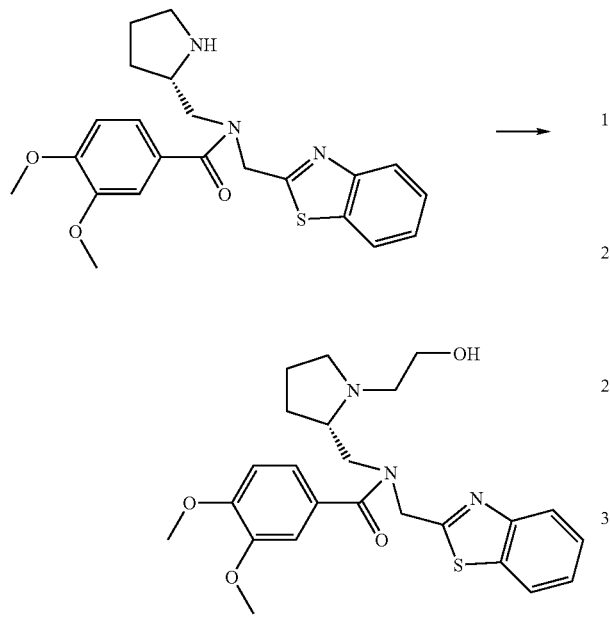

Experimental condition analogous to Example 22, from 0.2 g (0.48 mmol) N-benzothiazol-2-ylmethyl-3,4-dimethoxy-(S)—N-pyrrolidin-2-ylmethyl-benzamide, 2-bromo-ethanol, 73 mg (0.584 mmol), and 0.18 g (1.46 mmol) of diethylisopropylamine, and 5 mL acetonitrile. The reaction gave 129 mg of light yellow semi solid: $C_{24}H_{29}N_3O_4S$ [M+H]: 456.1. LC retention time on HPLC, C18 column gradient 20-95% acetonitrile with 0.1% TFA in 7 minutes: 0.754.

Example 27

This example illustrates the preparation of N-Benzothiazol-2-yl methyl-(S)—N-(1-cyclohexylmethyl-pyrrolidin-2-ylmethyl)-3,4-dimethoxy-benzamide.

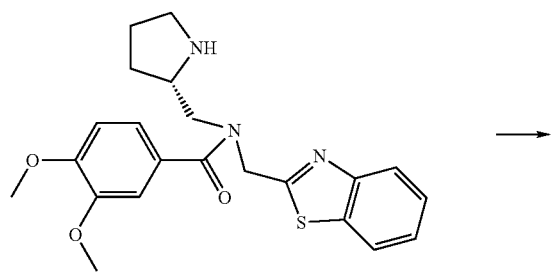

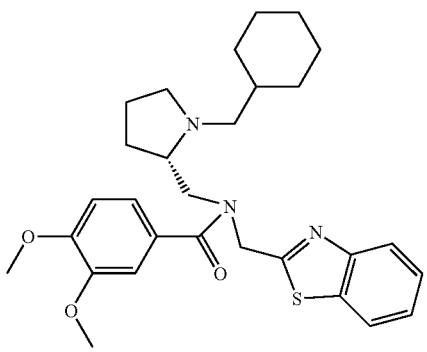

Experimental condition analogous to Example 23, from 0.21 g (0.52 mmol) of N-benzothiazol-2-yl methyl-(S)—N-[1-(2-hydroxy-ethyl)-pyrrolidin-2-ylmethyl]-3,4-dimethoxy-benzamide, 65 mg (0.58 mmol) of cyclohexane carboxaldehyde, and 99 mg (1.58 mmol) of sodium cyanoborohydride, in 5 mL of methanol, gave 91.6 of white viscous oil: $C_{29}H_{37}N_3O_3S$ [M+H]: 508.5. LC retention time on HPLC, C18 column gradient 20-95% acetonitrile with 0.1% TFA in 7 minutes: 4.007

Example 28

This example illustrates the preparation of N-Benzothiazol-2-yl methyl-(S)—N-(1-isopropyl-pyrrolidin-2-ylmethyl)-3,4-dimethoxy-benzamide.

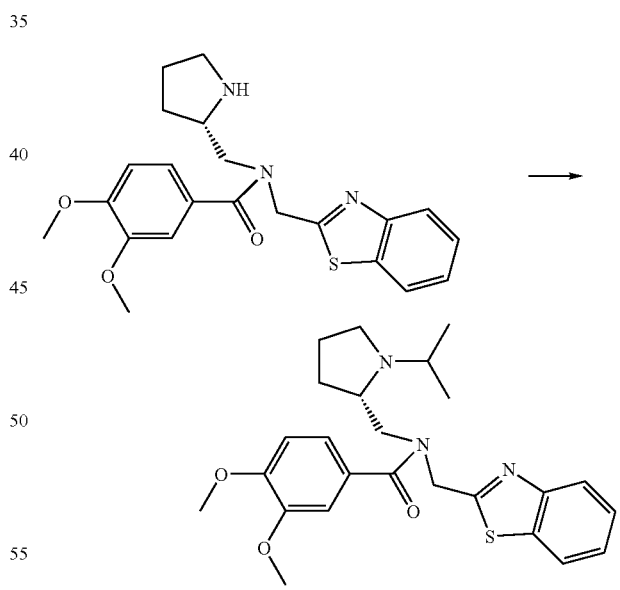

Experiment condition analogous to Example 23, from 0.20 g (0.48 mmol) of N-benzothiazol-2-yl methyl-(S)—N-[1-(2-hydroxy-ethyl)-pyrrolidin-2-ylmethyl]-3,4-dimethoxy-benzamide, 3 mL of acetone, and 92 mg (1.46 mmol) of sodium cyanoborohydride, in 3 mL of methanol, gave 90 mg of yellow oil: $C_{25}H_{31}N_3O_3S$ [M+H]: 454.2. LC retention time on HPLC, C18 column gradient 20-95% acetonitrile with 0.1% TFA in 7 minutes: 1.16

Example 29

This example illustrates the preparation of N-Benzo[b]thiophene-2-ylmethyl-3,4-dimethoxy-N—(S)-pyrrolidin-2-ylmethyl-benzamide.

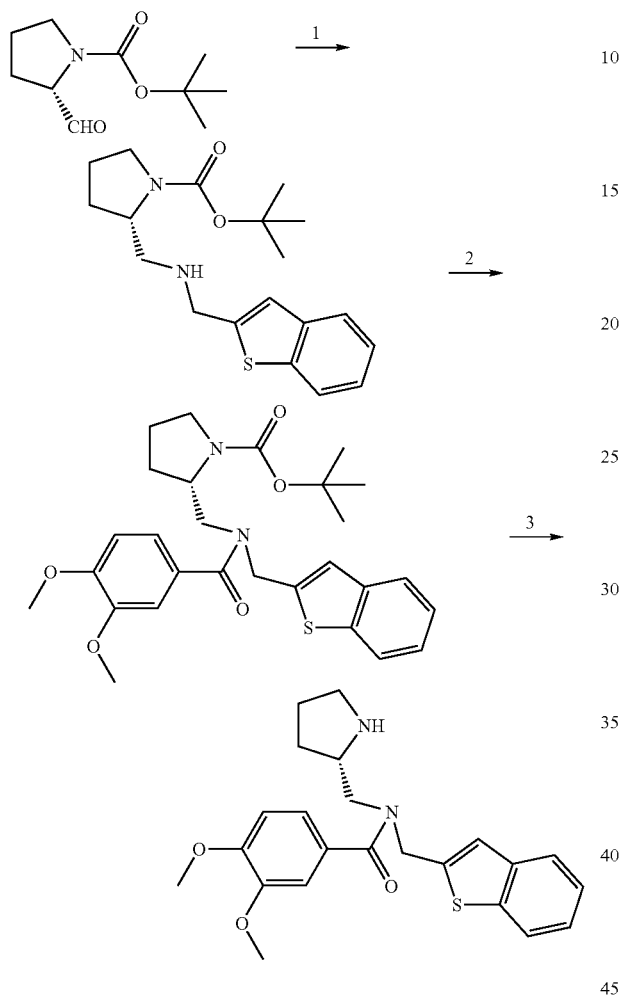

Step 1: 2-{[(Benzo[b]thiophen-2-ylmethyl)-amino]-methyl}-(S)-pyrrolidin-1-carboxylic acid tert-butyl ester. Experimental condition analogous to Example 24, from (S)-2-formyl-pyrrolidine-1-carboxylic acid tert-butyl ester 0.725 g (3.64 mmol), 0.59 g (3.64 mmol) C-benzo[b]thiophen-2-yl-methylamine and 0.686 g (10.92 mmol) of sodium cyanoborohydride in 10 mL of methanol, gave 1.22 g compound: LC-MSD, m/z for: $C_{19}H_{26}N_2O_2S$ [M+H]: 347.4. LC retention time on HPLC, C18 column gradient 20-95% acetonitrile with 0.1% TFA in 7 minutes: 3.71

Step 2: 2-{[Benzo[b]thiophen-2-ylmethyl-(3,4-dimethoxy-benzoyl)-amino]-methyl}-(S)-pyrrolidine-1-carboxylic acid tert-butyl ester. Experimental condition analogous to Example 21, from 1.22 g (3.52 mmol) of 2-{[(benzo[b]thiophen-2-ylmethyl)-amino]-methyl}-(S)-pyrrolidin-1-carboxylic acid tert-butyl ester, 0.74 g (3.70 mmol) of 3,4-benzoyl-chloride, and 0.71 g (7.04 mmol) triethylamine, in 30 mL dichloromethane, gave 1.856 g off white semi solid: LC-MSD, m/z for: $C_{28}H_{34}N_2O_5S$ [M+H]: 513.5. LC retention time on HPLC, C18 column gradient 20-95% acetonitrile with 0.1% TFA in 7 minutes: 5.183.

Step 3: N-Benzo[b]thiophene-2-ylmethyl-3,4-dimethoxy-N—(S)-pyrrolidin-2-ylmethyl-benzamide. Experimental condition analogous to Example 21, from 1.21 g (2.37 mmol) of 2-{[benzo[b]thiophen-2-ylmethyl-(3,4-dimethoxy-benzoyl)-amino]-methyl}-(S)-pyrrolidine-1-carboxylic acid tert-butyl ester, 15 mL of trifluoroacetic acid and 60 mL of dichloromethane, gave 740 mg of white semi solid compound: LC-MSD, m/z for: LC-MSD, m/z for: $C_{23}H_{26}N_2O_3S$ [M+H]: 411.2. LC retention time on HPLC, C18 column gradient 20-95% acetonitrile with 0.1% TFA in 7 minutes: 2.789.

Example 30

This example illustrates the preparation of N-Benzo[b]thiophen-2-yl methyl-(S)—N-(1-cyclohexylmethyl-pyrrolidin-2-ylmethyl)-3,4-dimethoxy-benzamide.

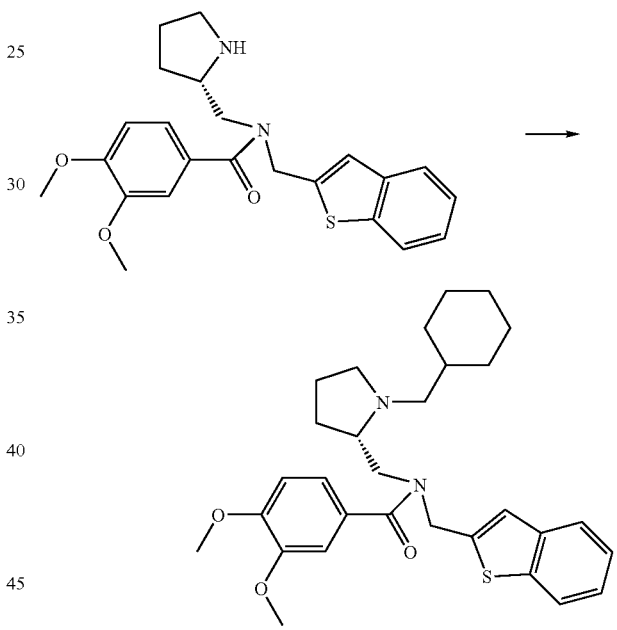

Experimental condition analogous to Example 23, from 75 mg (0.183 mmol) of N-benzo[b]thiophene-2-ylmethyl-3,4-dimethoxy-N—(S)-pyrrolidin-2-ylmethyl-benzamide, 25 mg (0.221 mmol) of cyclohexane carboxaldehyde, and 38 mg (0.552 mmol) of sodium cyanoborohydride, in 2 mL of methanol. Purification using reverse phase HPLC, C18 column gradient gave 20-80% with 0.1% TFA in 40 min, gave 25 mg pale yellow solid. $C_{30}H_{38}N_2O_3S$ [M+H]: 507.3. LC retention time on HPLC, C18 column gradient 20-95% acetonitrile with 0.1% TFA in 7 minutes: 3.983; $^1$H NMR (400 MHz, CDCl$_3$/HCl): δ 0.8-2.2 (m, 20 H), 3 (s, 1 H), 3.4-3.6 (m, 2 H), 3.8-4 (m, 7 H), 6.8 (m, 1 H), 7.0-7.4 (m, 6 H), 7.6-7.8 (m, 1 H).

Example 31

This example illustrates the preparation of N-Biphenyl-3-yl-4-difluoromethoxy-3-methoxy-(S)—N-pyrrolidin-2-ylmethyl-benzamide.

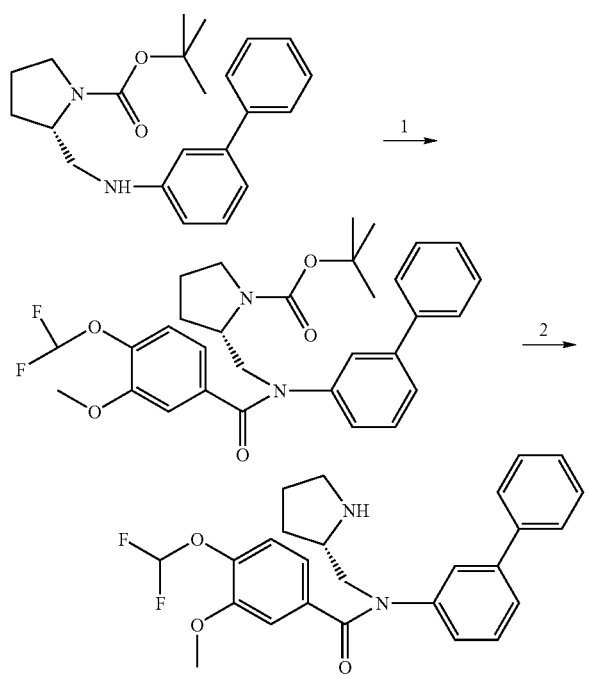

Step 1: 2-{[Biphenyl-3-yl-(4-difluoromethoxy-3-methoxy-benzoyl)-amino]-methyl}-(S)-pyrrolidine-1-carboxylic acid tert-butyl ester: Experimental condition analogous to Example 4, from 2-(biphenyl-3-ylaminomethyl)-(S)-pyrrolidine-1-carboxylic acid tert-butyl ester 0.63 g (1.79 mmol), 4-difluoromethoxy-3-methoxy-benzoyl chloride 0.44 g (1.87 mmol), and triethylamine 0.5 mL (3.58 mmol), and 10 mL of dichloromethane, gave 0.8 g product: LC-MSD, m/z for: $C_{31}H_{34}F_2N_2O_5$ [M+H]: 553.3. LC retention time on HPLC, C18 column gradient 20-95% acetonitrile with 0.1% TFA in 7 minutes: 5.6

Step 2: N-Biphenyl-3-yl-4-difluoromethoxy-3-methoxy-(S)—N-pyrrolidin-2-ylmethyl-benzamide. Experimental condition analogous to Example 1, from 1 g (1.94 mmol) of 2-(S)-{[biphenyl-3-yl-(3,4-dimethoxy-benzoyl)-amino]-methyl}-pyrrolidine-1-carboxylic acid tert-butyl ester, 25 mL of trifluoroacetic acid and 100 mL of dichloromethane. Gave 0.75 gram of white semi solid: LC-MSD, m/z for: $C_{26}H_{26}F_2N_2O_3$ [M+H]: 452.2. LC retention time on HPLC, C18 column gradient 20-95% acetonitrile with 0.1% TFA in 7 minutes: 3.54.

Example 32

This example illustrates the preparation of N-Biphenyl-3-yl-(S)—N-(1-cyclopropylmethyl-pyrrolidin-2-ylmethyl)-4-difluoromethoxy-3-methoxy-benzamide.

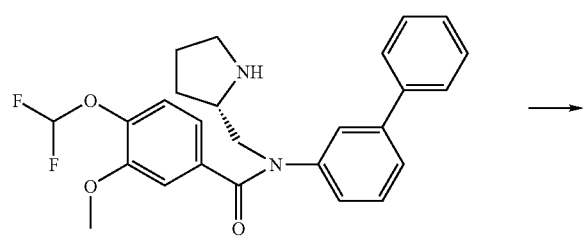

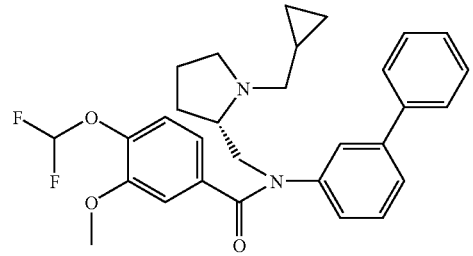

Experimental condition analogous to Example 22, from N-biphenyl-3-yl-4-difluoromethoxy-3-methoxy-(S)—N-pyrrolidin-2-ylmethyl-benzamide 0.18 g (0.4 mmol), 0.06 g (0.42 mmol) of bromoethyl cyclopropane and 0.14 mL (0.8 mmol) diisopropylethylamine. Reaction gave 100 mg of yellow oil: LC-MSD, m/z for: $C_{30}H_{32}F_2N_2O_3$ [M+H]: 507.3. LC retention time on HPLC, C18 column gradient 20-95% acetonitrile with 0.1% TFA in 7 minutes: 4.12; $^1$H NMR (400 MHz, CDCl$_3$/HCl): δ 0.2-0.5 (m, 2 H), 2.4-2.6 (m, 2 H), 1.5-1.9 (m, 6 H), 2.1-2.3 (m, 2 H), 3.3 (s, 1 H), 3.6 (s, 3H), 3.9-4 (m, 1 H), 4.1-4.2 (m, 1 H), 6.6 (d, 1 H), 6.3-6.6 (m, 1 H), 6.8-7 (m, 2 H), 7.2-7.5 (m, 8 H).

Example 33

This example illustrates the preparation of N-biphenyl-3-yl-(S)—N-(1-cyclohexylmethyl-pyrrolidin-2-ylmethyl)-4-difluoromethoxy-3-methoxy-benzamide.

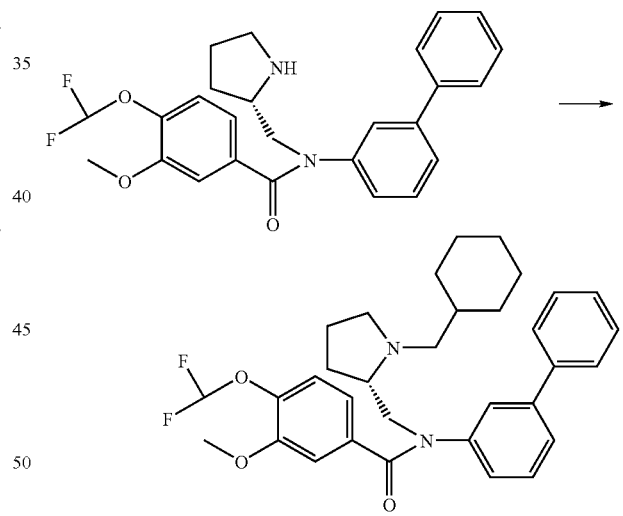

Experimental condition analogous to Example 23, from 0.18 g (0.4 mmol) from N-biphenyl-3-yl-4-difluoromethoxy-3-methoxy-(S)—N-pyrrolidin-2-ylmethyl-benzamide, 48 mg (0.4 mmol) of cyclohexanecarbaldehyde, and 90 mg (1.44 mmol) of sodium cyanoborohydride, in 6 ml tetrahydrofurane, and 0.02 mL acetic acid. Purification on silica gel and elution with chloroform-methanol 20% gave 60 mg of light yellow oil: LC-MSD, m/z for: $C_{33}H_{38}N_2O_3F_2$ [M+H]: 549.4. LC retention time on HPLC, C18 column gradient 20-95% acetonitrile with 0.1% TFA in 7 minutes: 4.693; $^1$H NMR (400 MHz, CDCl$_3$/HCl): δ 0.8-1 (m, 2 H), 1.1-1.4 (m, 4 H), 1.5-2 (m, 10 H), 2.3-2.6 (m, 2 H), 2.8-3 (s, 1 H), 3.1-3.4 (m, 2H), 3.8 (s, 3 H), 4.0-4.3 (m, 2 H), 6.2-6.6 (m, 1 H), 6.8-7.1 (m, 3 H), 7.2-7.5 (m, 8 H).

Example 34

This example illustrates the preparation of N-(3'-Cyano-biphenyl-3-yl)-(S)—N-(1-cyclopropylmethyl-pyrrolidin-2-ylmethyl)-3,4-dimethoxy-benzamide.

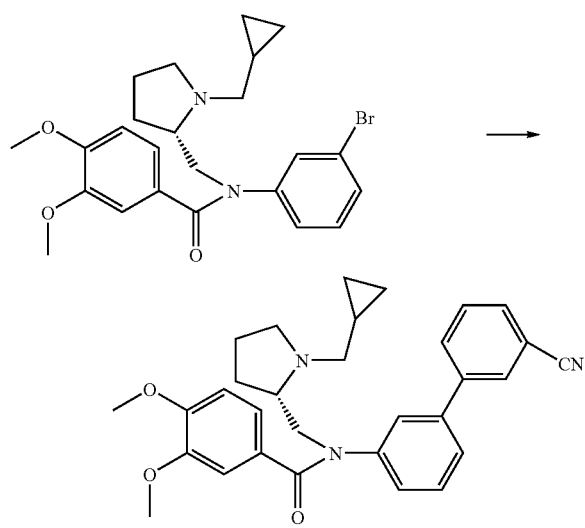

In 10 mL of dimethylformamide was dissolved 0.26 g (0.55 mmol) of N-(3-bromo-phenyl)-(S)—N-(1-cyclopropylmethyl-pyrrolidin-2-ylmethyl)-3,4-dimethoxy-benzamide, 3-cyanophenylboronic acid 0.16 g (1.1 mmol), 0.7 mL of 2 molar solution of (1.37 mmol) sodium carbonate and 60 mg (0.05 mmol) of tetrakis(triphenylphosphine)palladium(0). The mixture was heated at 90° C. under nitrogen overnight. The reaction was cooled to room temperature, saturated bicarbonate solution was added and was extracted with diethyl ether. Gave 38 mg of light brown oil. LC-MSD, m/z for: $C_{31}H_{33}N_3O_3$ [M+H]: 596.3. LC retention time on HPLC, C18 column gradient 20-95% acetonitrile with 0.1% TFA in 7 minutes: 3.639; $^1$H NMR (400 MHz, CDCl$_3$/HCl): δ 0.4-0.6 (m, 2 H), 0.9-1 (m, 1 H), 1.5-1.9 (m, 7 H), 2.1-2.4 (m, 2 H), 2.85-3 (m, 2 H), 3.3-3.4 (m, 1H), 3.6 (s, 3 H), 3.8 (s, 3 H), 3.85-4 (m, 1 H), 4.05-4.1 (m, 1 H), 6.6-7.0 (m, 3 H), 7.2-7.6 (m, 8 H).

Example 35

This example illustrates the preparation of(S)—N-(1-Cyclopropylmethyl-pyrrolidin-2-ylmethyl)-3,4-dimethoxy-N-(3-pyridin-3-yl-phenyl)-benzamide.

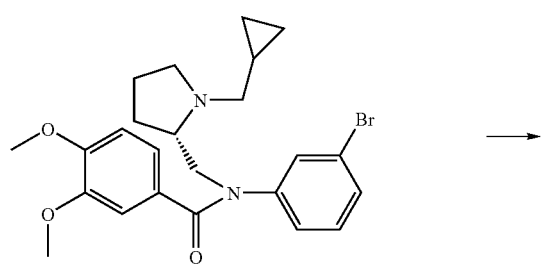

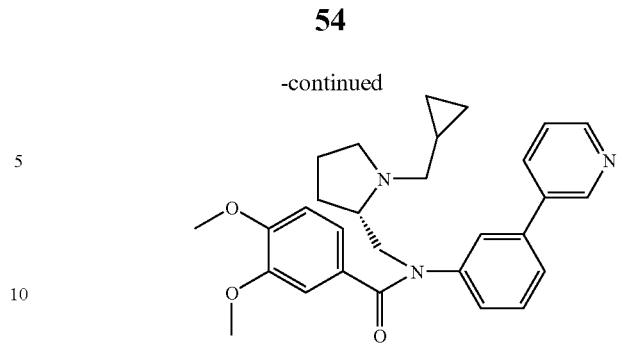

Experimental condition analogous to Example 34, 0.28 g (0.59 mmol) of N-(3-bromo-phenyl)-(S)—N-(1-cyclopropylmethyl-pyrrolidin-2-ylmethyl)-3,4-dimethoxy-benzamide, pyridine-3-boronic acid 0.15 g (1.18 mmol), 0.18 g (1.47 mmol) sodium carbonate, and 60 mg (0.05 mmol) of tetrakis(triphenylphosphine)palladium(0) in 10 mL of dimethylformamide and 0.1 mL water, gave 70 mg of yellow oil. LC-MSD, m/z for: $C_{29}H_{33}N_3O_3$ [M+H]: 471.3. LC retention time on HPLC, C18 column gradient 20-95% acetonitrile with 0.1% TFA in 7 minutes: 0.813; $^1$H NMR (400 MHz, CDCl$_3$/HCl): δ 0.4-0.6 (m, 2 H), 0.9-1 (m, 1 H), 1.5-1.9 (m, 7 H), 2.1-2.4 (m, 2 H), 2.85-3 (m, 2 H), 3.3-3.4 (m, 1H), 3.6 (s, 3 H), 3.8 (s, 3 H), 3.85-4 (m, 1 H), 4.05-4.1 (m, 1 H), 6.6-7.6(m, 9 H), 8.5-8.7 (m, 2 H).

Example 36

This example illustrates the preparation of (S)-3'-[(1-Cyclopropylmethyl-pyrrolidin-2-ylmethyl)-(3,4-dimethoxy-benzoyl)-amino]-biphenyl-4-carboxylic acid ethyl ester.

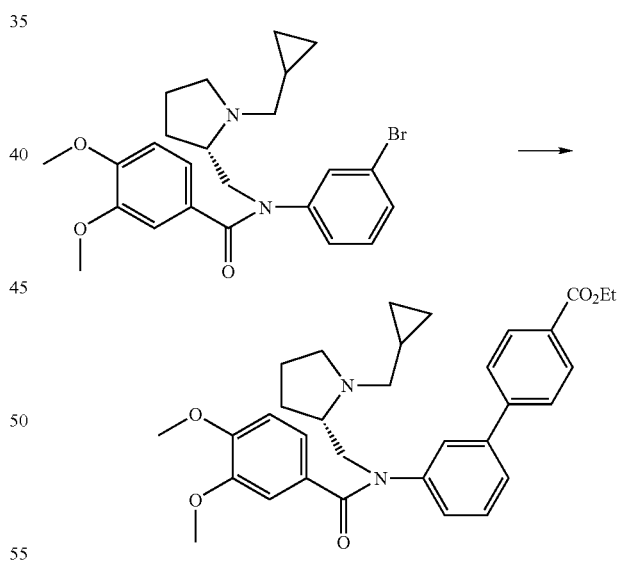

Experimental condition analogous to Example 34, 0.2 g (0.42 mmol) of N-(3-bromo-phenyl)-(S)—N-(1-cyclopropylmethyl-pyrrolidin-2-ylmethyl)-3,4-dimethoxy-benzamide, 0.16 g (0.82 mmol) 4-ethoxycarbonylphenylboronic acid, 0.13 g (1.05 mmol) sodium carbonate, and 50 mg (0.04 mmol) of tetrakis(triphenylphosphine)palladium(0) 10 mL of dimethylformamide and 0.2 mL water, gave 170 mg of yellow oil. LC-MSD, m/z for: $C_{33}H_{38}N_2O_5$ [M+H]: 543.3. LC retention time on HPLC, C18 column gradient 20-95% acetonitrile with 0.1% TFA in 7 minutes: 4.207; $^1$H NMR (400 MHz, CDCl$_3$/HCl): δ 0.4-0.6 (m, 2 H), 0.9-1 (m, 1 H), 1.4 (t, 3 H), 1.5-1.9 (m, 7 H), 2.1-2.4 (m, 2 H), 2.85-3 (m, 2 H), 3.3-3.4 (m, 1H), 3.6 (s, 3 H), 3.8 (s, 3 H), 3.85-4 (m, 1 H), 4.05-4.1 (m, 1 H), 4.4 (q, 2 H), 6.6-7.4(m, 9 H), 8.02 (m, 2 H).

Example 37

This example illustrates the preparation of (S)—N-(1-Cyclopropylmethyl-pyrrolidin-2-ylmethyl)-N-(4'-dimethylamino-biphenyl-3-yl)-3,4-dimethoxy-benzamide.

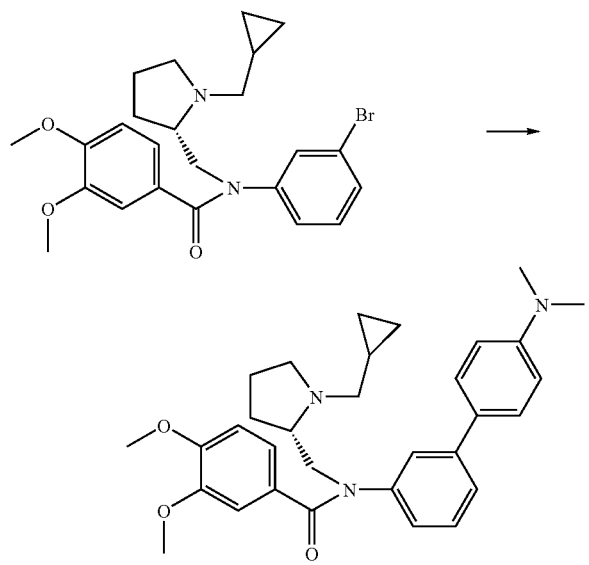

Experimental condition analogous to Example 34, 0.25 g (0.53 mmol) of N-(3-bromo-phenyl)-(S)—N-(1-cyclopropylmethyl-pyrrolidin-2-ylmethyl)-3,4-dimethoxy-benzamide, 0.17 g (1.6 mmol) 4-dimethyllphenylboronic acid, 0.16 g (1.32 mmol) sodium carbonate, and 60 mg (0.05 mmol) of tetrakis(triphenylphosphine)palladium(0) 10 mL of dimethylformamide and 0.2 mL water, gave 130 mg of orange oil. LC-MSD, m/z for: $C_{32}H_{39}N_3O_3$ [M+H]: 514.3. LC retention time on HPLC, C18 column gradient 20-95% acetonitrile with 0.1% TFA in 7 minutes: 5.13; $^1$H NMR (400 MHz, CDCl$_3$/HCl): δ 0.4-0.6 (m, 2 H), 0.9-1 (m, 1 H), 1.4, 1.5-1.9 (m, 7 H), 2.1-2.4 (m, 2 H), 2.85-3 (m, 2 H), 3.01 (s, 6 H), 3.3-3.4 (m, 1H), 3.6 (s, 3 H), 3.8 (s, 3 H), 3.85-4 (m, 1 H), 4.05-4.1 (m, 1 H), 4.4 (q, 2 H), 6.6-7.4 (m, 11 H).

Example 38

This example illustrates the preparation of N-(3'-Chloro-4'-fluoro-biphenyl-3-yl)-(S)—N-(1-cyclopropylmethyl-pyrrolidin-2-ylmethyl)-3,4-dimethoxy-benzamide.

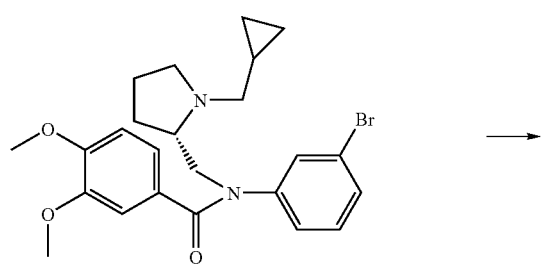

-continued

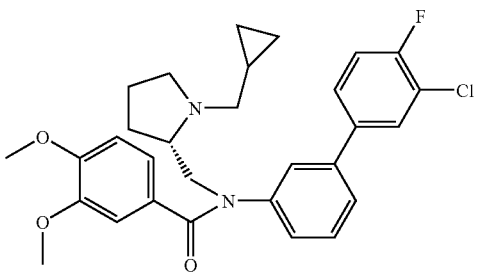

Experimental condition analogous to Example 34, 0.27 g (0.57 mmol) of N-(3-bromo-phenyl)-(S)—N-(1-cyclopropylmethyl-pyrrolidin-2-ylmethyl)-3,4-dimethoxy-benzamide, 0.2 g (1.4 mmol) 3-chloro-4-fluorophenylboronic acid, 0.18 g (1.42 mmol) sodium carbonate, and 70 mg (0.05 mmol) of tetrakis(triphenylphosphine)palladium(0) 10 mL of dimethylformamide and 0.2 mL water, gave 100 mg of yellow oil. LC-MSD, m/z for: $C_{30}H_{32}N_2O_3FCl$ [M+H]: 523.2. LC retention time on HPLC, C18 column gradient 20-95% acetonitrile with 0.1% TFA in 7 minutes: 4.865.

Example 39

This example illustrates the preparation of 7-Methoxy-2,2-dimethyl-benzo[1,3]dioxole-5-carboxylic acid ((S)-1-azetidin-3-ylmethyl-pyrrolidin-2-ylmethyl)-isoquinolin-3-ylmethyl-amide.

Step 1: Isoquinoline-3-carboxylic acid methoxy-methyl-amide

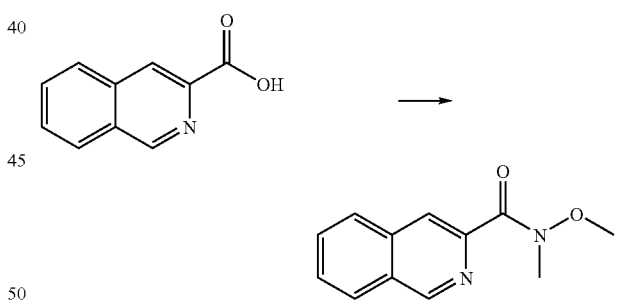

2.46 g (12.9 mmol) of isoquinoline-3-carboxylic acid hydrate was dissolved in 100 mL dichloromethane under room temperature. 1.38 g (14.1 mmol) of methoxymethyl amine was added followed by addition of 4.55 g (15.5 mmol) of 4-(4,6-Dimethoxy-1,3,5-triazin-2-yl)-4-methylmorpholinium chloride and 1.44 g (14.1 mmol) of triethylamine. The reaction was stirred for 18 hour and 250 ml of water was added. The organic layer was dried over anhydrous magnesium sulfate and evaporated in vacuum. Purification using flash chromatography, elution with 100% ethyl acetate yielded to 2.70 g of product as colorless solid. LC-MSD, m/z for $C_{14}H_{25}NO_3$ [M+H]+: 217.3, [M+2H]+: 218.3. LC retention time on HPLC, C18 column gradient 20-95% acetonitrile with 0.1% TFA in 4 min: 0.492 min.

Step 2: Isoquinoline-3-carbaldehyde

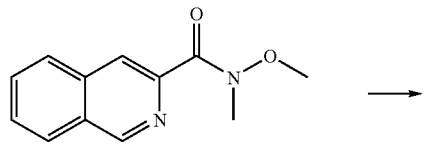

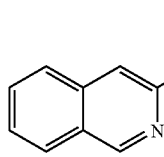

To a solution of 1.35 g (6.24 mmol) of isoquinoline-3-carboxylic acid methoxy-methyl-amide was dissolved in 50 ml tetrahydrofuran, 7.49 mL of 1.0 M DIBAL solution in heptane was added at −78° C. The reaction was warmed to room temperature and stirred for 1 hour at r.t., and then quenched by addition of 10 mL saturated sodium bicarbonate. 100 mL of water was added followed by extraction with 100 ml of dichloromethane. The organic layer was dried over anhydrous magnesium sulfate and evaporated in vacuum to give colorless oil. The crude was used to next step without further purification. LC-MSD, m/z for $C_{10}H_7NO$ [M+H]+: 158.2. LC retention time on HPLC, C18 column gradient 20-95% acetonitrile with 0.1% TFA in 4 min: 0.221 min.

Step 3: (S)-2-{[(Isoquinolin-3-ylmethyl)-amino]-methyl}-pyrrolidine-1-carboxylic acid tert-butyl ester.

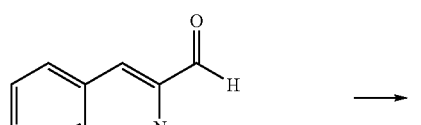

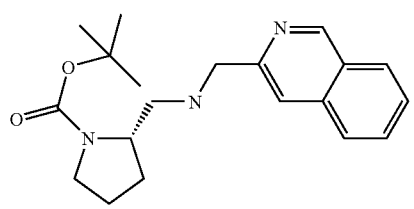

To a solution of 314 mg (2.0 mmol) of isoquinoline-3-carbaldehyde in 20 mL dichloromethane, 0.4 g (2.0 mmol) of (S)-2-Aminomethyl-pyrrolidine-1-carboxylic acid tert-butyl ester and 0.84 mg (4.0 mmol) of sodium triacethoxy borohydride were added. The reaction was stirred at room temperature for 2 hours, then quenched by addition of 10 mL saturated sodium bicarbonate. 100 mL of water was added into the mixture and extracted with 100 mL of chloroform. The organic layer was dried over anhydrous magnesium sulfate and evaporated in vacuum to yield colorless oil. The crude product was purified by prep-HPLC to yield 620 mg of product as colorless viscous oil. LC-MSD, m/z for $C_{20}H_{27}N_3O_2$ [M+H]+: 342.5. LC retention time on HPLC, C18 column gradient 20-95% acetonitrile with 0.1% TFA in 4 min: 1.572 min.

Step 4: 7-Methoxy-2,2-dimethyl-benzo[1,3]dioxole-5-carboxylic acid isoquinolin-3-ylmethyl-(S)-1-pyrrolidin-2-ylmethyl-amide.

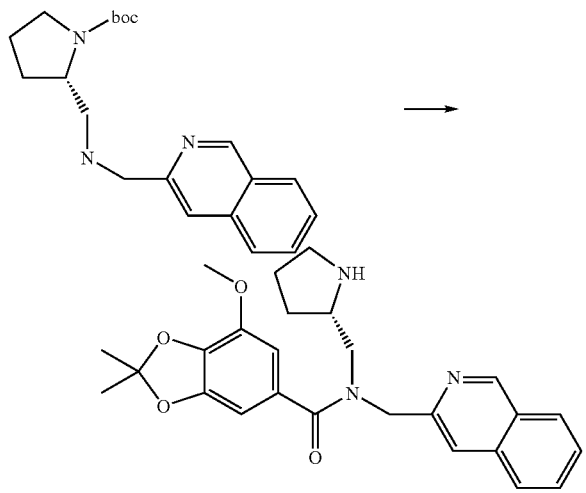

To a solution of 0.62 g (1.82 mmol) of (S)-2-{[(isoquinolin-3-ylmethyl)-amino]-methyl}-pyrrolidine-1-carboxylic acid tert-butyl ester was dissolved in 20 mL of dichloromethane, 0.485 g (1.99 mmol) of 7-methoxy-2,2-dimethyl-benzo[1,3]dioxole-5-carbonyl chloride, 0.214 mg (1.99 mmol) of triethylamine were added at r.t. The reaction was stirred for 1 hour, quenched by addition of 5 mL saturated sodium bicarbonate solution. 100 mL of water was added followed by extraction with 100 mL of chloroform. The organic layer was dried over anhydrous magnesium sulfate and evaporated in vacuum. The residue was dissolved in 20 mL of dichloromethane followed by addition of 2 mL of trifluoroacetic acid. The mixture was stirred for 1 hour then quenched by addition of 20 mL saturated sodium biacarbonate. 100 mL of water was added followed by extraction with 100 mL of dichloromethane. The organic layer was dried over anhydrous magnesium sulfate and evaporated in vacuum. The crude was purified by flash chromatography to yield 580 mg of product as colorless viscous oil. LC-MSD, m/z for $C_{30}H_{35}N_3O_5$ [M+H]+: 448.5. LC retention time on HPLC, C18 column gradient 20-95% acetonitrile with 0.1% TFA in 4 min: 1.675 min.

Step 5: 7-Methoxy-2,2-dimethyl-benzo[1,3]dioxole-5-carboxylic acid ((S)-1-azetidin-3-ylmethyl-pyrrolidin-2-ylmethyl)-isoquinolin-3-ylmethyl-amide:

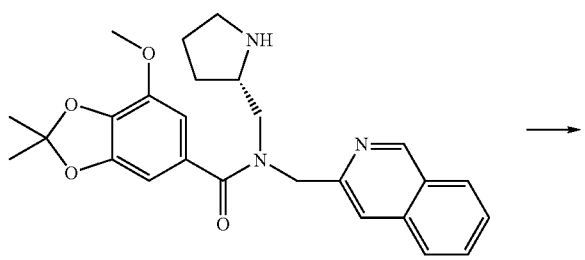

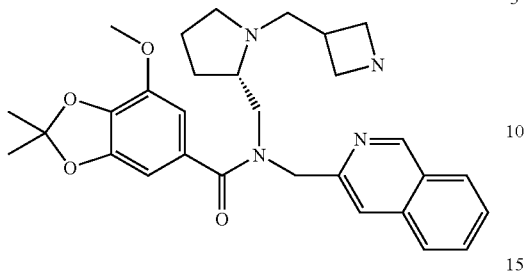
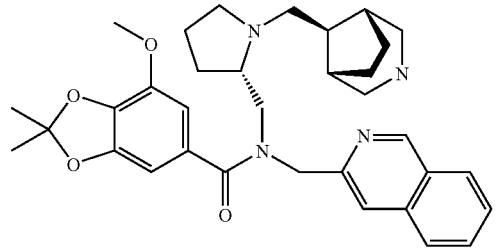

In 3 mL of dichloromethane was dissolved 0.09 g (0.20 mmol) of 2,2-dimethyl-benzo[1,3]dioxole-5-carboxylic acid isoquinolin-3-ylmethyl-(S)-1-pyrrolidin-2-ylmethyl-amide, followed by addition of 0.14 g (0.76 mmol) of Boc-azetidine carboxaldehyde and 0.42 g (2 mmol) of sodium triacethoxyborohydride. The mixture was stirred for 1 hour at r.t. and the reaction was quenched by addition of 5 ml saturated sodium bicarbonate. 50 mL of water was added and the mixture was extracted with 50 ml of dichloromethane. The organic layer was dried over magnesium sulfate and evaporated to yield colorless oil. The crude was dissolved in 3 mL of dichloromethane followed by addition of 0.5 mL of trifluoroacetic acid. The mixture was stirred for 30 minutes and reaction was quenched by addition of 5 mL of saturated sodium bicarbonate. 20 mL of water was added followed by extraction with 20 mL of dichloromethane. The organic layer was dried over MgSO$_4$ and evaporated in vacuum. The crude product was purified by Prep. HPLC to yield 24 mg of product as colorless oil. LC-MSD, m/z for $C_{30}H_{36}N_4O_4$ [M+H]+: 517.7, [M+2H]+:518.7. LC retention time on HPLC, C18 column gradient 20-95% acetonitrile with 0.1% TFA in 4 min: 1.213 min. $^1$H NMR (400 MHz, CDCl$_3$): δ 1.5-2.2 (m, 9 H), 2.2-3.2 (m, 9 H), 3.2-3.5 (m, 2 H), 3.5-4.1 (m, 5 H), 5.0 (s, 2 H), 6.62 (s, 1 H), 6.78 (s, 1 H), 7.5 (s, 1 H), 7.6 (t, 1 H), 7.7 (t, 1H), 7.8 (t, 1 H), 7.95 (t, 1 H), 9.1 (d, 1 H).

Example 40

This example illustrates the preparation of 7-Methoxy-2,2-dimethyl-benzo[1,3]dioxole-5-carboxylic acid [1-(3-aza-bicyclo[3.2.1]oct-8-ylmethyl)-(S)-1-pyrrolidin-2-ylmethyl]-isoquinolin-3-ylmethyl-amide.

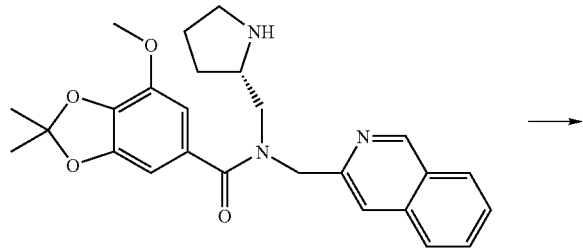

Experimental conditions analogous to Example 1, from 0.12 g (0.27 mmol) of 2,2-dimethyl-benzo[1,3]dioxole-5-carboxylic acid isoquinolin-3-ylmethyl-(S)-1-pyrrolidin-2-ylmethyl-amide, 0.097 g (0.41 mmol) of 8-formyl-3-aza-bicyclo[3.2.1]octane-3-carboxylic acid tert-butyl ester in 2 mL dichloromethane. The deprotection was conducted by the addition of 0.5 mL TFA into the crude dissolved in 3 mL of dichloromethane. The crude product was purified by Prep. HPLC to yield 44 mg of product as yellow viscous oil. LC-MSD, m/z for $C_{34}H_{42}N_4O_4$ [M+H]+: 571.7, [M+2H]+: 572.7. LC retention time on HPLC, C18 column gradient 20-95% acetonitrile with 0.1% TFA in 4 min: 1.338 min; $^1$H NMR (400 MHz, CDCl$_3$): δ 1.2-2.2 (m, 18 H), 2.4-3.1 (m, 4 H), 3.1-4.0 (m, 9 H), 5.0 (s, 2 H), 6.62 (s, 1 H), 6.74 (s, 1 H), 7.5 (s, 1 H), 7.6 (t, 1 H), 7.7 (t, 1 H), 7.8 (d, 1 H), 7.95 (d, 1 H), 9.1 (s, 1 H).

Example 41a

This example illustrates the 7-Methoxy-2,2-dimethyl-benzo[1,3]dioxole-5-carboxylic acid [1-(3-aza-bicyclo[3.2.1]oct-8-ylmethyl)-pyrrolidin-2-ylmethyl]-[1,8]naphthyridin-2-ylmethyl-amide.

Step 1: [1,8]Naphthyridine-2-carbaldehyde

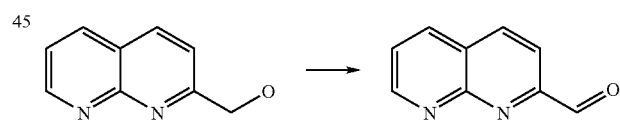

[1,8]-Naphthyridin-2-yl-methanol was synthesized according to the method described in the literature (Newkome, George R. et al, *J. Org. Chem.* 55(9), 1990, 2838-2842). 1.5 g (9.38 mmol) [1,8]Naphthyridin-2-yl-methanol was dissolved in 40 mL of dichloromethane and 8.8 g (20 mmol) of Dess-Martin Periodinate was added and the mixture was stirred for 2 hours. 5 g of solid Na$_2$S$_2$O$_3$ was added to quench the reaction followed by 20 mL of saturated NaHCO$_3$. 200 mL of water was added and then extracted with 150 mL of chloroform 3 times. The organic layer was separated and the dried over anhydrous magnesium sulfate. The solution was evaporated in vacuum to yield 1.38 g of product as yellow oil. The crude product was used directly for the next step. LC-MSD, m/z for $C_9H_6N_2O$ [M+H]+: 159.2, [M+2H]+: 160.2. LC retention time on HPLC, C18 column gradient 20-95% acetonitrile with 0.1% TFA in 4 min: 0.255 min.

Step 2: (S)-2-{[([1,8]Naphthyridin-3-ylmethyl)-amino]-methyl}-pyrrolidine-1-carboxylic acid tert-butyl ester:

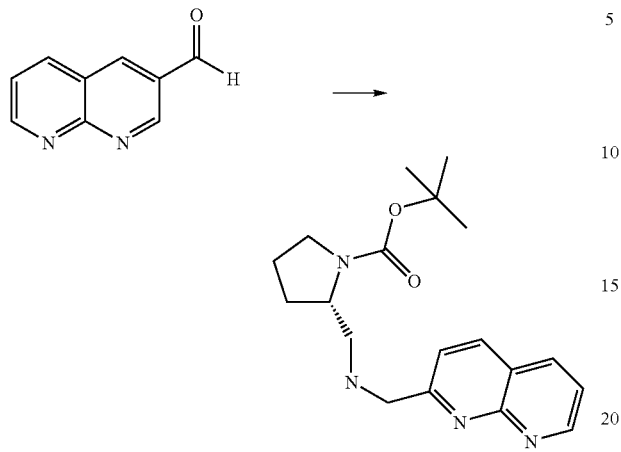

Experimental conditions analogous to Example 1, from 0.17 g (0.85 mmol) of 2-aminomethyl-pyrrolidine-1-carboxylic acid tert-butyl ester, 0.14 g (0.85 mmol) of [1,8]naphthyridine-2-carbaldehyde, 8 mL dichloromethane, 0.4 g (1.81 mmol) of sodium triacethoxyborohydride. The crude product was purified by Prep. HPLC to yield 90 mg of product as yellow viscous oil. LC-MSD, m/z for $C_{19}H_{26}N_4O_2$ [M+H]+: 343.2, [M+2H]+: 344.2. LC retention time on HPLC, C18 column gradient 20-95% acetonitrile with 0.1% TFA in 4 min: 0.377 min.

Step 3: 7-Methoxy-2,2-dimethyl-benzo[1,3]dioxole-5-carboxylic acid [1,8]naphthyridin-2-ylmethyl-(S)-1-pyrrolidin-2-ylmethyl-amide:

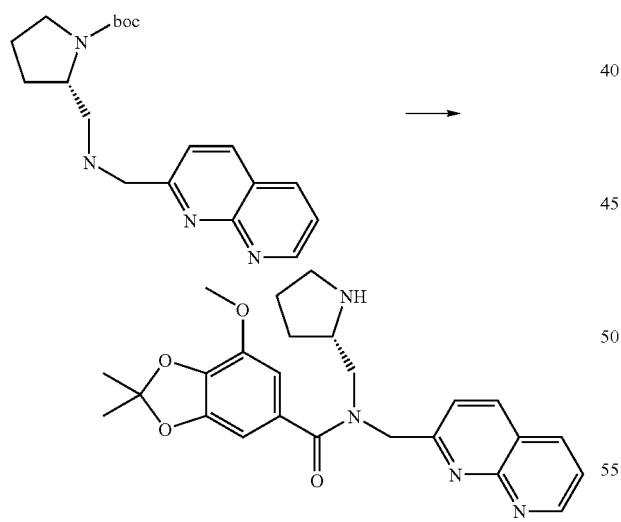

Experimental conditions analogous to Example 15, from 0.09 g (0.263 mmol) of 2-{[([1,8]naphthyridin-3-ylmethyl)-amino]-methyl}-(S)-1-pyrrolidine-1-carboxylic acid tert-butyl ester, 0.07 g (0.289 mmol) of 7-methoxy-2,2-dimethyl-benzo[1,3]dioxole-5-carbonyl chloride, 0.035 g (0.29 mmol) of triethylamine in 5 mL dichloromethane. The crude product was purified by Prep. HPLC to yield 120 mg of yellow viscous oil. The deprotection was conducted by the addition of 0.5 mL TFA into the crude dissolved in 3 mL of dichloromethane. The crude was used for the next step without further purification. LC-MSD, m/z for $C_{30}H_{38}N_2O_4$ [M+H]+: 449.6, [M+2H]+: 450.6; LC retention time on HPLC, C18 column gradient 20-95% acetonitrile with 0.1% TFA in 4 min: 0.695 min.

Step 4: 7-Methoxy-2,2-dimethyl-benzo[1,3]dioxole-5-carboxylic acid [1-(3-aza-bicyclo[3.2.1]oct-8-ylmethyl)-(S)-1-pyrrolidin-2-ylmethyl]-[1,8]naphthyridin-2-ylmethyl-amide:

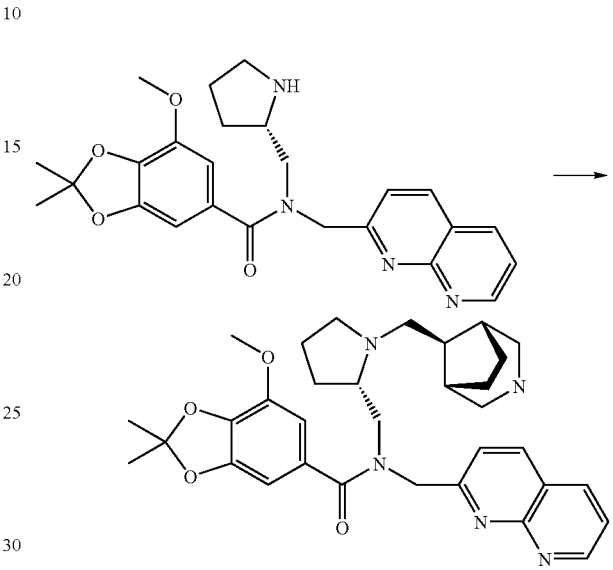

Experimental conditions analogous to Example 1, from 0.12 g (0.27 mmol) of 7-methoxy-2,2-dimethyl-benzo[1,3]dioxole-5-carboxylic acid [1,8]naphthyridin-2-ylmethyl-(S)-1-pyrrolidin-2-ylmethyl-amide, 0.097 g (0.41 mmol) of 8-formyl-3-aza-bicyclo[3.2.1]octane-3-carboxylic acid tert-butyl ester in 2 mL dichloromethane. The deprotection was conducted by the addition of 0.5 mL TFA into the crude dissolved in 3 mL of dichloromethane. The crude product was purified to yield 44 mg of yellow viscous oil. LC-MSD, m/z for $C_{34}H_{42}N_4O_4$ [M+H]+: 572.7, [M+2H]+: 573.7. LC retention time on HPLC, C18 column gradient 20-95% acetonitrile with 0.1% TFA in 4 min: 0.268 min; $^1$H NMR (400 MHz, CD$_3$OD): δ 1.1-1.4 (m, 4 H), 1.4-2.0 (m, 13 H), 2.0-2.6 (m, 4 H), 2.7-3.4 (m, 4 H), 3.4-4.0 (m, 6 H), 5.1 (m, 2 H), 6.5-6.9 (m, 2 H), 7.5-7.7 (m, 2 H), 8.42 (m, 2 H), 9.02 (d, 1 H).

Example 41b

This example illustrates the preparation of 7-Methoxy-2,2-dimethyl-benzo[1,3]dioxole-5-carboxylic acid [1-(3-aza-bicyclo[3.2.1]oct-8-ylmethyl)-(S)-1-pyrrolidin-2-ylmethyl]-[1,8]naphthyridin-2-ylmethyl-amide:

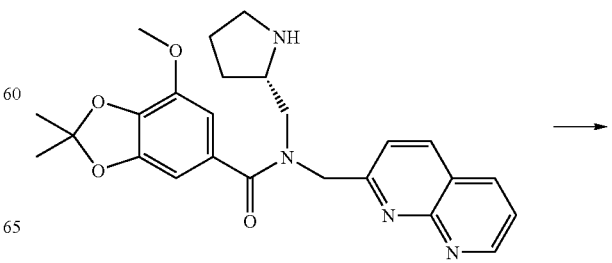

-continued

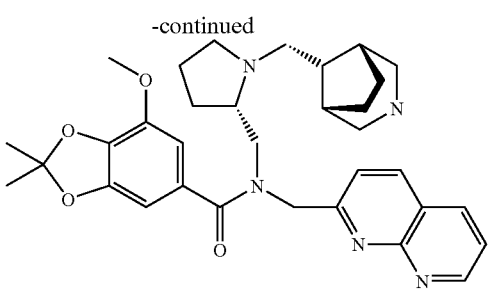

Experimental conditions analogous to Example 1, from 0.12 g (0.27 mmol) of 7-methoxy-2,2-dimethyl-benzo[1,3] dioxole-5-carboxylic acid [1,8]naphthyridin-2-ylmethyl-(S)-1-pyrrolidin-2-ylmethyl-amide, 2 mL dichloromethane, 0.09 mg (0.41 mmol) of 8-formyl-3-aza-bicyclo[3.2.1]octane-3-carboxylic acid tert-butyl ester. The deprotection was conducted by the addition of 0.5 mL TFA into the crude dissolved in 3 mL of dichloromethane. The crude product was purified to yield 44 mg of yellow viscous oil (29%). LC-MSD, m/z for $C_{33}H_{41}N_5O_4$ [M+H]+: 572.7, [M+2H]+: 573.7; LC retention time on HPLC, C18 column gradient 20-95% acetonitrile with 0.1% TFA in 4 min: 0.298 min;

$^1$HNMR (400 MHz, CD$_3$OD): δ 1.1-1.4 (m, 4 H), 1.4-2.0 (m, 13 H), 2.0-2.6 (m, 4 H), 2.7-3.4 (m, 4 H), 3.4-4.0 (m, 6 H), 5.1 (m, 2 H), 6.5-6.9 (m, 2 H), 7.5-7.7 (m, 2 H), 8.42 (m, 2 H), 9.02 (d, 1 H).

Example 42

This example illustrates the preparation of 7-Methoxy-2,2-dimethyl-benzo[1,3]dioxole-5-carboxylic acid [1,8]naphthyridin-2-ylmethyl-[(2S,3aS,7aS)-1-(octahydro-indol-2-yl)methyl]-amide.

Step 1: (2S,3aS,7aS)-2-{[([1,8]Naphthyridin-2-ylmethyl)-amino]-methyl}-octahydro-indole-1-carboxylic acid tert-butyl ester

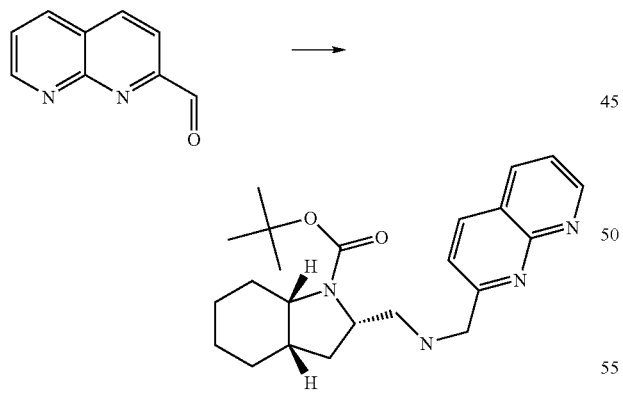

Experimental conditions analogous to Example 1, from 0.12 g (0.48 mmol) of (2S,3aS,7aS)-2-aminomethyl-octahydro-indole-1-carboxylic acid tert-butyl ester, 69 mg (0.44 mmol) of [1,8]naphthyridine-2-carbaldehyde, 0.18 g (0.88 mmol) of sodium triacetoxyborohydride in 5 mL dichloromethane. The crude product was purified by prep-HPLC to yield 110 mg of product as yellow viscous oil. LC-MSD, m/z for $C_{23}H_{32}N_4O_2$ [M+H]+: 397.5, [M+2H]+: 398.5. LC retention time on HPLC, C18 column gradient 20-95% acetonitrile with 0.1% TFA in 4 min: 1.926 min.

Step 2: 7-Methoxy-2,2-dimethyl-benzo[1,3]dioxole-5-carboxylic acid [1,8]naphthyridin-2-ylmethyl-[(2S,3aS,7aS)-1-(octahydro-indol-2-yl)methyl]-amide.

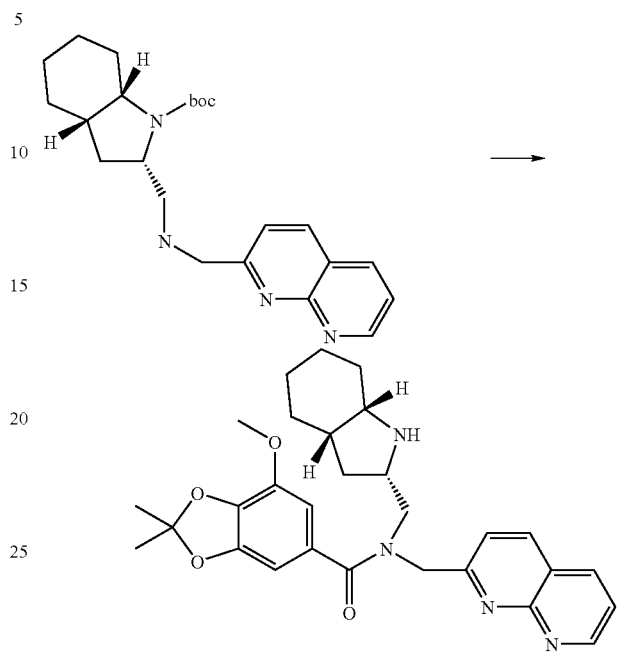

Experimental conditions analogous to Example 1, 0.11 g (0.278 mmol) of (2S,3aS,7aS)-2-{[([1,8]naphthyridin-2-ylmethyl)-amino]-methyl}-octahydro-indole-1-carboxylic acid tert-butyl ester, 97 mg (0.396 mmol) of 7-methoxy-2,2-dimethyl-benzo[1,3]dioxole-5-carbonyl chloride, 73 mg (0.61 mmol) of triethylamine in 5 mL dichloromethane. The crude product was purified by prep-HPLC to yield 50 mg of yellow viscous oil. The deprotection was conducted by the addition of 0.5 mL TFA into the crude dissolved in 3 ml of dichloromethane. The crude was purified by prep-HPLC to yield 22 mg product. LC-MSD, m/z for $C_{29}H_{34}N_4O_4$ [M+H]+: 502.6, [M+2H]+: 503.6; LC retention time on HPLC, C18 column gradient 20-95% acetonitrile with 0.1% TFA in 4 min: 1.910 min; $^1$H NMR (400 MHz, CD$_3$OD): δ 1.0-1.2 (m, 2 H), 1.12-2.12 (m, 1 H), 1.14-1.80 (m, 10 H), 1.8-2.02 (m, 2 H), 2.1-2.3 (m, 1 H), 2.4-2.6 (m, 1 H), 3.2-3.4 (s, 3 H), 3.7-4.1 (m, 3 H), 4.5-4-4.5 (s, 1 H), 5.0-5.1 (m, 2 H), 6.42 (s, 1 H), 6.50 (s, 1 H), 7.42 (s, 1H), 7.64 (m, 1 H), 8.4-8.6 (m, 2 H), 9.1 (m, 1 H)

Example 43

This example illustrates the preparation of 7-Methoxy-2,2-dimethyl-benzo[1,3]dioxole-5-carboxylic acid ((S)-1-cyclobutyl-pyrrolidin-2-ylmethyl)-quinolin-2-ylmethyl-amide.

Step 1: (S)-2-{[(Quinolin-2-ylmethyl)-amino]-methyl}-pyrrolidine-1-carboxylic acid tert-butyl ester

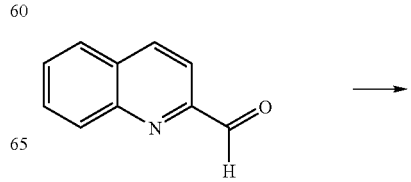

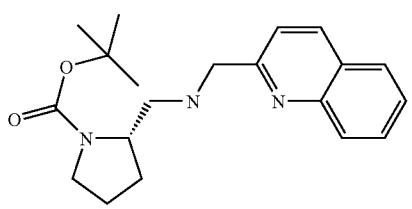

Experimental conditions analogous to Example 1, from 0.66 g (3.3 mmol) of 2-aminomethyl-pyrrolidine-1-carboxylic acid tert-butyl ester, 0.47 g (3.0 mmol) of quinoline-2-carbaldehyde, 1.46 g (6.6 mmol) of sodium triacethoxyborohydride in 10 mL dichloromethane. The crude product was purified by flash chromatograph to yield 955 mg of product as yellow viscous oil. LC-MSD, m/z for $C_{20}H_{27}N_3O_2$ [M+H]+: 342.5, [M+2H]+: 343.5. LC retention time on HPLC, C18 column gradient 20-95% acetonitrile with 0.1% TFA in 4 min: 1.719 min.

Step 2: 7-Methoxy-2,2-dimethyl-benzo[1,3]dioxole-5-carboxylic acid (S)-1-pyrrolidin-2-ylmethyl-quinolin-2-ylmethyl-amide

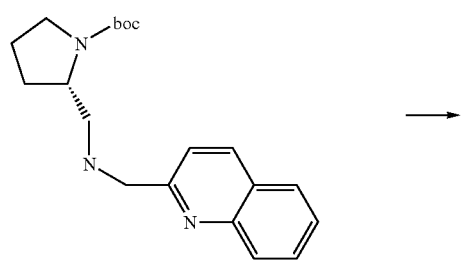

Experimental conditions analogous to Example 15, from 0.95 mg (2.80 mmol) of (S)-2-aminomethyl-pyrrolidine-1-carboxylic acid tert-butyl ester, 0.72 g (3.0 mmol) of 7-methoxy-2,2-dimethyl-benzo[1,3]dioxole-5-carbonyl chloride, 0.38 mg (3.0 mmol) of triethylamine and 30 mL dichloromethane. The crude product was purified by flash chromatography to yield 990 mg of yellow solid. The deprotection was conducted by the addition of 1.5 mL TFA into the crude dissolved in 10 mL of dichloromethane. The crude was purified by flash chromatography to yield 701 mg of product as yellow viscous oil. LC-MSD, m/z for $C_{26}H_{29}N_3O_6$ [M+H]+: 448.6. LC retention time on HPLC, C18 column gradient 20-95% acetonitrile with 0.1% TFA in 4 min: 1.710 min.

Step 3: 7-Methoxy-2,2-dimethyl-benzo[1,3]dioxole-5-carboxylic acid ((S)-1-cyclobutyl-pyrrolidin-2-ylmethyl)-quinolin-2-ylmethyl-amide.

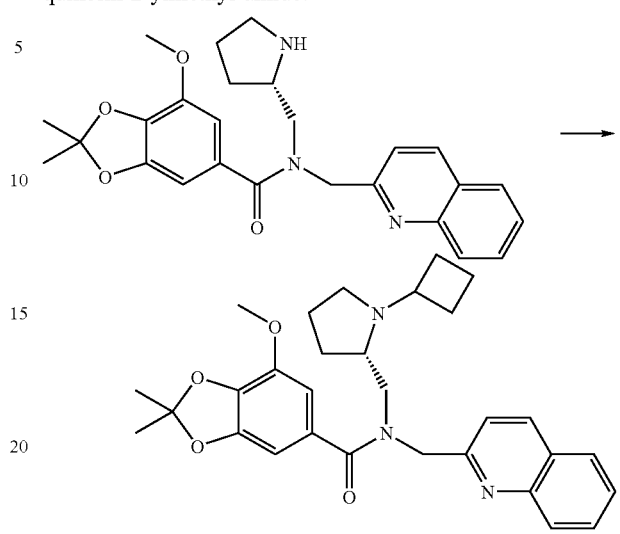

Experimental conditions analogous to Example 1, from 0.16 g (0.29 mmol) of 7-methoxy-2,2-dimethyl-benzo[1,3]dioxole-5-carboxylic acid pyrrolidin-2-ylmethyl-quinolin-2-ylmethyl-amide, 41 mg (0.58 mmol) of butanone, 0.12 mg (0.58 mmol) of sodium triacethoxyborohydride in 3 mL dichloromethane. The crude product was purified by prep-HPLC to yield 51 mg of product as light yellow viscous oil. LC-MSD, m/z for $C_{30}H_{35}N_3O_4$ [M+H]+: 502.7, [M+H]+: 503.7; LC retention time on HPLC, C18 column gradient 20-95% acetonitrile with 0.1% TFA in 4 min: 2.005 min; $^1$H NMR (400 MHz, CD$_3$OD): δ 1.3-1.4 (m, 2 H), 1.5-1.7 (s, 6 H), 1.70-1.86 (m, 2 H), 1.86-2.08 (m, 3 H), 2.1-2.4 (m, 3 H), 3.0-3.2 (m, 1 H), 3.4-3.6 (s, 3 H), 3.6-4.0 (m, 4 H), 5.0 (s, 2 H), 6.62 (s, 1 H), 6.77 (d, 1H), 7.37 (s, 1 H), 7.60 (t, 1 H), 7.78 (t, 1 H), 7.92(d, 1H), 8.04(d, 1 H), 8.30 (d, 1 H).

Example 44

This example illustrates the preparation of 7-Methoxy-2,2-dimethyl-benzo[1,3]dioxole-5-carboxylic acid ((S)-1-azetidin-3-ylmethyl-pyrrolidin-2-ylmethyl)-quinolin-2-ylmethyl-amide.

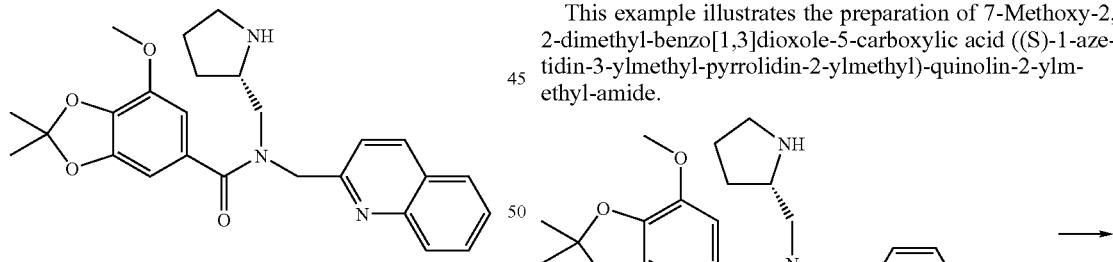

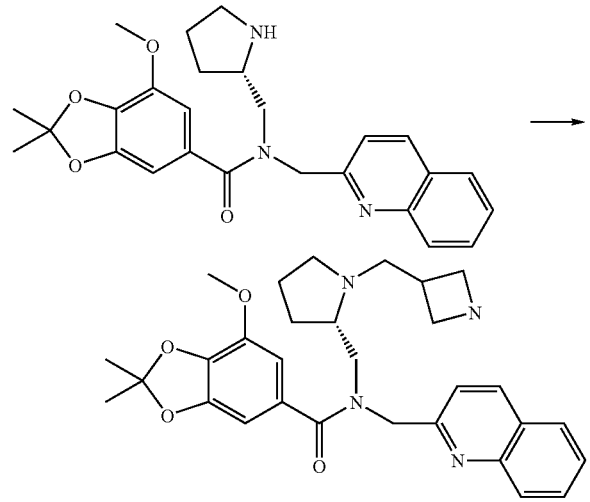

Experimental conditions analogous to Example 1, from 0.171 g (0.38 mmol) of 7-methoxy-2,2-dimethyl-benzo[1,3]dioxole-5-carboxylic acid (S)-1-pyrrolidin-2-ylmethyl-quinolin-2-ylmethyl-amide, 70 mg (0.38 mmol) of butanone, 0.168 g (0.58 mmol) of sodium triacethoxyborohydride in 3 mL dichloromethane. The crude product was purified to yield 24 mg of yellow viscous oil. LC-MSD, m/z for $C_{30}H_{36}N_4O_4$ [M+H]+: 517.7, [M+H]+: 518.7. LC retention time on HPLC, C18 column gradient 20-95% acetonitrile with 0.1% TFA in 4 min: 0.658 min; $^1$H NMR (400 MHz, CD$_3$OD): δ 1.4-2.0 (m, 8 H), 2.0-2.2 (m, 4 H), 2.3-2.5 (m, 1 H), 2.6-3.0 (m, 4 H), 3.1-3.5 (m, 3 H), 3.5-4.0 (m, 5 H), 5.0 (s, 2 H), 6.62 (s, 1 H), 6.77 (d, 1H), 7.37 (s, 1 H), 7.60 (t, 1 H), 7.78 (t, 1 H), 7.92(d, 1 H), 8.04(d, 1 H), 8.30 (d, 1 H)

Example 45

This example illustrates the preparation of 7-Methoxy-2,2-dimethyl-benzo[1,3]dioxole-5-carboxylic acid [1-(3-aza-bicyclo[3.2.1]oct-8-ylmethyl)-(S)-1-pyrrolidin-2-ylmethyl]-quinolin-2-ylmethyl-amide.

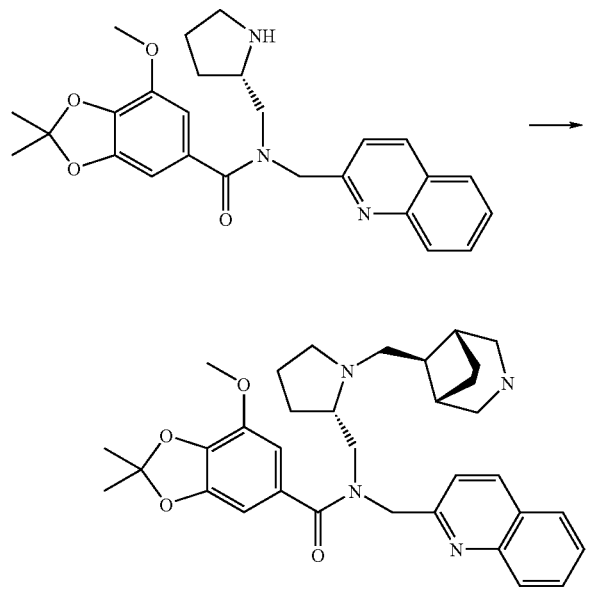

Experimental conditions analogous to Example 1, from 0.18 mg (0.33 mmol) of 7-methoxy-2,2-dimethyl-benzo[1,3]dioxole-5-carboxylic acid (S)-pyrrolidin-2-ylmethyl-quinolin-2-ylmethyl-amide, 3 mL dichloromethane, 91 mg (0.38 mmol) of 8-formyl-3-aza-bicyclo[3.2.1]octane-3-carboxylic acid tert-butyl ester, 0.168 mg (0.58 mmol) of sodium triacethoxyborohydride. The crude product was purified by prep-HPLC to yield 20 mg of product as yellow viscous oil. LC-MSD, m/z for $C_{34}H_{42}N_4O_4$ [M+H]+: 571.7, LC retention time on HPLC, C18 column gradient 20-95% acetonitrile with 0.1% TFA in 4 min: 1.262 min; $^1$H NMR (400 MHz, CD$_3$OD): δ 1.1-2.3 (m, 20 H), 2.3-4.0 (m, 12 H), 5.1 (m, 2 H), 6.60 (s, 1 H), 6.70 (s, 1H), 7.3-7.5 (m, 1 H), 7.56 (t, 1 H), 7.72 (t, 1 H), 7.8 (d, 1 H), 8.02 (d, 1H), 8.08 (d, 1 H).

Example 46

This example illustrates the preparation of 7-Methoxy-2,2-dimethyl-benzo[1,3]dioxole-5-carboxylic acid [1-(3-aza-bicyclo[3.2.1]oct-8-ylmethyl)-(S)-1pyrrolidin-2-ylmethyl]-quinolin-2-ylmethyl-amide.

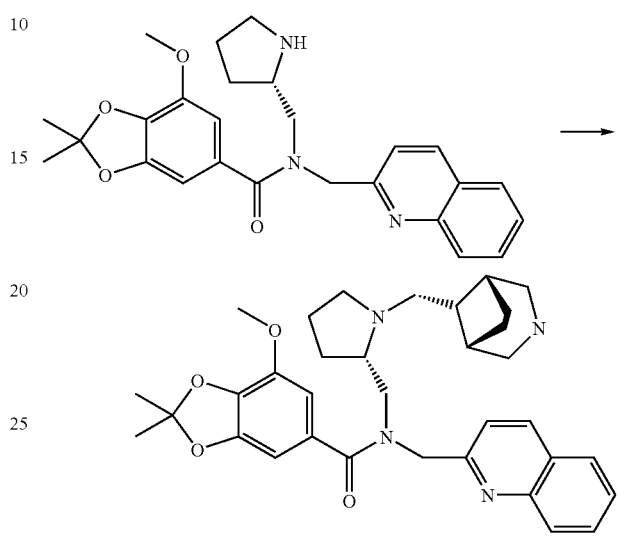

Experimental conditions analogous to Example 1, from 0.18 g (0.33 mmol) of 7-methoxy-2,2-dimethyl-benzo[1,3]dioxole-5-carboxylic acid (S)-pyrrolidin-2-ylmethyl-quinolin-2-ylmethyl-amide, 91 mg (0.38 mmol) of 8-Formyl-3-aza-bicyclo[3.2.1]octane-3-carboxylic acid tert-butyl ester, 0.16 g (0.58 mmol) of sodium triacethoxyborohydride in 3 mL DCM. The crude product was purified by prep-HPLC to yield 20 mg of product as yellow viscous oil. LC-MSD, m/z for $C_{34}H_{42}N_4O_4$ [M+H]+: 571.7, [M+2H]+: 572.7; LC retention time on HPLC, C18 column gradient 20-95% acetonitrile with 0.1% TFA in 4 min: 1.079 min; $^1$H NMR (400 MHz, CD$_3$OD): δ 1.0-1.4 (m, 4 H), 1.4-2.6 (m, 20 H), 2.6-3.1 (m, 2 H), 3.2-4.0 (m, 6 H), 5.1 (s, 2 H), 6.60 (s, 1 H), 6.70 (s, 1H), 7.3-7.5 (m, 1 H), 7.56 (t, 1 H), 7.7 (t, 1 H), 7.8 (d, 1 H), 8.02 (d, 1 H), 8.08 (d, 1 H).

Example 47

This example illustrates the preparation of 7-Methoxy-2,2-dimethyl-benzo[1,3]dioxole-5-carboxylic acid {(S)-1-[2-(2-methoxy-ethoxy)-ethyl]-pyrrolidin-2-ylmethyl}-quinolin-2-ylmethyl-amide.

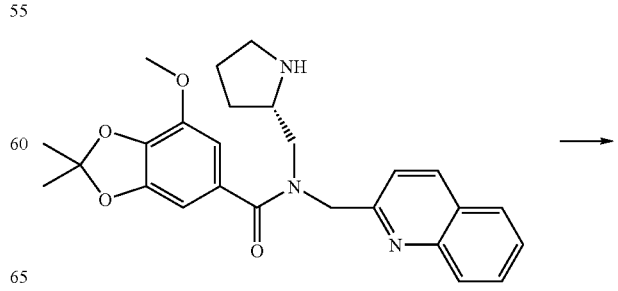

-continued

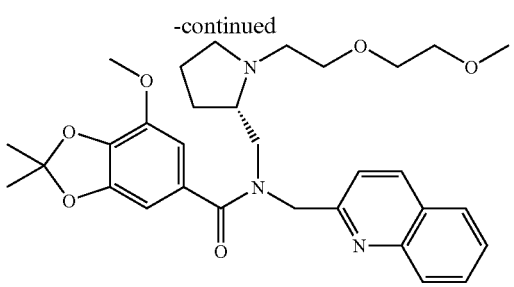

In 2 mL of dimethyl sulfoxide were dissolved, 80 mg (18 mmol) of 7-methoxy-2,2-dimethyl-benzo[1,3]dioxole-5-carboxylic acid (S)-1-pyrrolidin-2-ylmethyl-quinolin-2-ylmethyl-amide, 66 mg (36 mmol) of 1-bromo-2-(2-methoxy-ethoxy)-ethane, and 70 mg of cesium carbonate, the reaction was stirred at 85° C. for 6 hour. The reaction mixture was poured into 50 mL of water and then extracted with 50 mL of chloroform. The organic layer was dried over anhydrous magnesium sulfate and concentrated. The crude was purified by prep-HPLC to yield 26 mg of product as colorless viscous oil. LC-MSD, m/z for $C_{31}H_{39}N_3O_6$ [M+H]+: 550.7, [M+2H]+: 551.7. LC retention time on HPLC, C18 column gradient 20-95% acetonitrile with 0.1% TFA in 4 min: 2.046 min; $^1$H NMR (400 MHz, $CD_3OD$): δ 0.7-1.5 (m, 6 H), 1.5-2.2 (m, 7 H), 2.2-3.1 (m, 5 H), 3.2-4.1 (m, 11 H), 5.02 (s, 2 H), 6.58 (s, 1 H), 6.70 (s, 1H), 7.37 (s, 1 H), 7.58 (t, 1 H), 7.77 (t, 1 H), 7.94 (d, 1 H), 8.02 (d, 1 H) 8.32 (m, 1 H).

Example 48

This example illustrates the preparation of 3-{[(Quinolin-2-ylmethyl)-amino]-methyl}-azetidine-1-carboxylic acid tert-butyl ester.

Step 1:

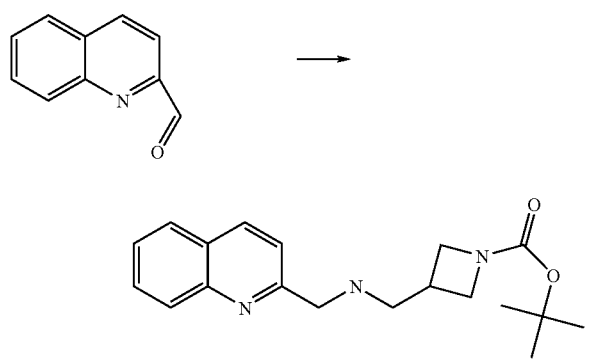

Experimental conditions analogous to Example 1, from 0.17 g (0.95 mmol) of amine, 0.14 g (0.89 mmol) of quinoline-2-carbaldehyde, 0.45 g (2.04 mmol) of sodium triacetoxyborohydride in 10 mL dichloromethane. The crude product was purified by prep-HPLC to yield 260 mg of product as yellow viscous oil. LC-MSD, m/z for $C_{20}H_{27}N_3O_2$ [M+H]+: 328.5, [M+2H]+: 329.5. LC retention time on HPLC, C18 column gradient 20-95% acetonitrile with 0.1% TFA in 4 min: 1.318 min.

Step 2: 7-Methoxy-2,2-dimethyl-benzo[1,3]dioxole-5-carboxylic acid azetidin-3-ylmethyl-quinolin-2-ylmethyl-amide.

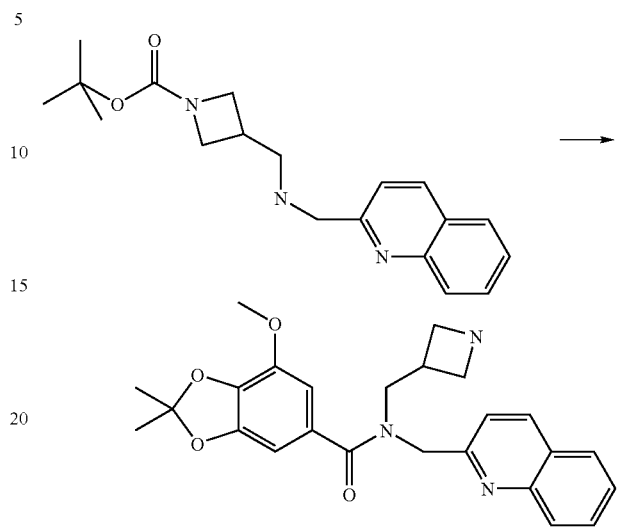

Experimental conditions analogous to Example 1, 0.26 g (0.80 mmol) of 3-{[(quinolin-2-ylmethyl)-amino]-methyl}-azetidine-1-carboxylic acid tert-butyl ester, 0.19 g (0.80 mmol) of 7-methoxy-2,2-dimethyl-benzo[1,3]dioxole-5-carbonyl chloride, 95 mg (0.80 mmol) of triethylamine and 28 mL dichloromethane. The crude product was purified by flash chromatography to yield 0.36 g of yellow solid. The deprotection was conducted by the addition of 2 mL TFA into the crude dissolved in 10 ml of dichloromethane. The crude was purified by flash Chromatography to yield 250 mg of product as colorless viscous oil. LC-MSD, m/z for $C_{25}H_{27}N_3O_4$ [M+H]+: 434.6, [M+2H]+: 435.6. LC retention time on HPLC, C18 column gradient 20-95% acetonitrile with 0.1% TFA in 4 min: 1.582 min; $^1$H NMR (400 MHz, $CD_3OD$): δ 1.67 (s, 6 H), 2.8-4.4 (m, 10 H), 4.90 (s, 2 H), 6.58 (s, 1 H), 6.70 (s, 1H), 7.38 (s, 1 H), 7.62 (t, 1 H), 7.82 (t, 1 H), 7.95 (d, 1 H), 8.06 (d, 1 H) 8.36 (m, 1 H).

Example 49

This example illustrates the preparation of 7-Methoxy-2,2-dimethyl-benzo[1,3]dioxole-5-carboxylic acid (1-methyl-azetidin-3-ylmethyl)-quinolin-2-ylmethyl-amide.

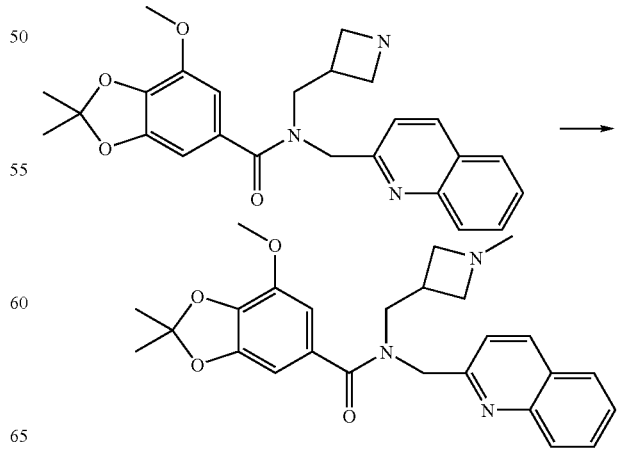

60 mg (0.14 mmol) of 7-methoxy-2,2-dimethyl-benzo[1,3]dioxole-5-carboxylic acid azetidin-3-ylmethyl-quinolin-2-ylmethyl-amide was dissolved in 5 mL of methanol. 50 mg (3.85 mmol) of paraformaldehyde and 50 mg (0.83 mmol) of sodium cyanoborohydride (0.83 mmol) were added and the mixture were stirred at r.t. for 3 hours. The reaction was quenched by adding 5 mL of saturated sodium borohydride solution and 50 mL of water then extracted with 50 mL of chloroform. The organic layer was dried over anhydrous magnesium sulfate and concentrated to yield colorless solid. The crude was purified by prep-HPLC to yield 20 mg of product as colorless solid. LC-MSD, m/z for $C_{26}H_{29}N_3O_6$ [M+H]+: 448.6, [M+2H]+: 449.6. LC retention time on HPLC, C18 column gradient 20-95% acetonitrile with 0.1% TFA in 4 min: 1.693 min; $^1$H NMR (400 MHz, CD$_3$OD): δ 1.67 (s, 6 H), 2.8-4.4 (m, 13 H), 4.90 (s, 2 H), 6.58 (s, 1 H), 6.70 (s, 1H), 7.38 (s, 1 H), 7.62 (t, 1 H), 7.82 (t, 1 H), 7.95 (d, 1 H), 8.06 (d, 1 H) 8.36 (m, 1 H).

Example 50

This example illustrates the preparation of 7-Methoxy-2,2-dimethyl-benzo[1,3]dioxole-5-carboxylic acid ((S)-1-cyclobutyl-pyrrolidin-2-ylmethyl)-(4-phenyl-thiazol-2-ylmethyl)-amide.

Step 1: (S)-2-{[(4-Phenyl-thiazol-2-ylmethyl)-amino]-methyl}-pyrrolidine-1-carboxylic acid tert-butyl ester.

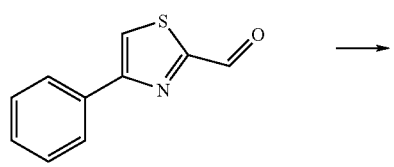

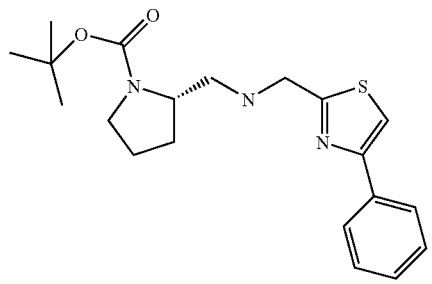

Experimental conditions analogous to Example 1, from 0.3 g (1.5 mmol) of (S)-2-aminomethyl-pyrrolidine-1-carboxylic acid tert-butyl ester, 0.28 mg (1.5 mmol) of 4-phenyl-thiazole-2-carbaldehyde, 30 mL dichloromethane, 0.66 g (3.0 mmol) of sodium triacethoxyborohydride. The crude product was purified by flash chromatography to yield 309 mg of product as colorless viscous oil. LC-MSD, m/z for $C_{20}H_{27}N_3O_2$ [M+H]+: 374.5, [M+2H]+: 375.5. LC retention time on HPLC, C18 column gradient 20-95% acetonitrile with 0.1% TFA in 4 min: 1.951 min.

Step 2: 7-Methoxy-2,2-dimethyl-benzo[1,3]dioxole-5-carboxylic acid (5-phenyl-thiazol-2-ylmethyl)-(S)-1-pyrrolidin-2-ylmethyl-amide.

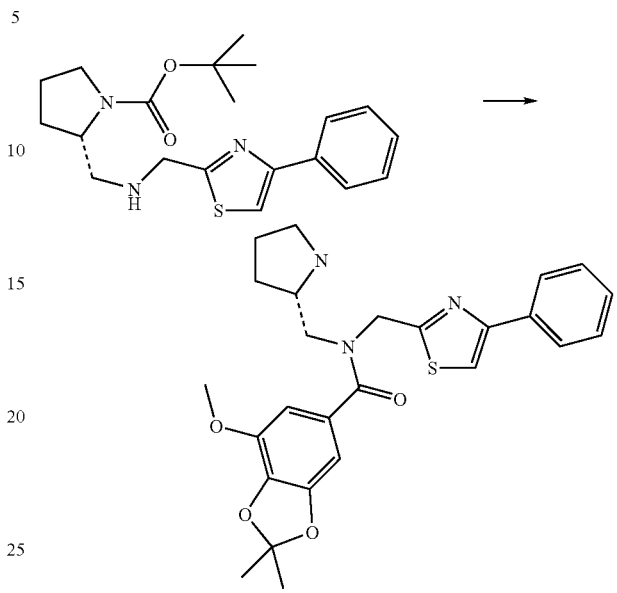

Experimental conditions analogous to Example 1, from 0.3 g (0.83 mmol) of (S)-2-{[(5-phenyl-thiazol-2-ylmethyl)-amino]-methyl}-pyrrolidine-1-carboxylic acid tert-butyl ester, 0.21 g (0.87 mmol) of 7-methoxy-2,2-dimethyl-benzo[1,3]dioxole-5-carbonyl chloride, 0.1 mg (0.87 mmol) of triethylamine and 10 mL dichloromethane. The crude product was purified by flash chromatography to yield 396 mg of yellow solid. The de-protection was conducted by the addition of 1.5 mL TFA into the crude dissolved in 10 mL of dichloromethane. The crude was purified by flash chromatograph to yield 250 mg of product as colorless viscous oil. LC-MSD, m/z for $C_{26}H_{29}N_3O_6$ [M+H]+: 480.6, [M+2H]+: 481.6. LC retention time on HPLC, C18 column gradient 20-95% acetonitrile with 0.1% TFA in 4 min: 1.974 min.

Step 3: 7-Methoxy-2,2-dimethyl-benzo[1,3]dioxole-5-carboxylic acid ((S)-1-cyclobutyl-pyrrolidin-2-ylmethyl)-(4-phenyl-thiazol-2-ylmethyl)-amide.

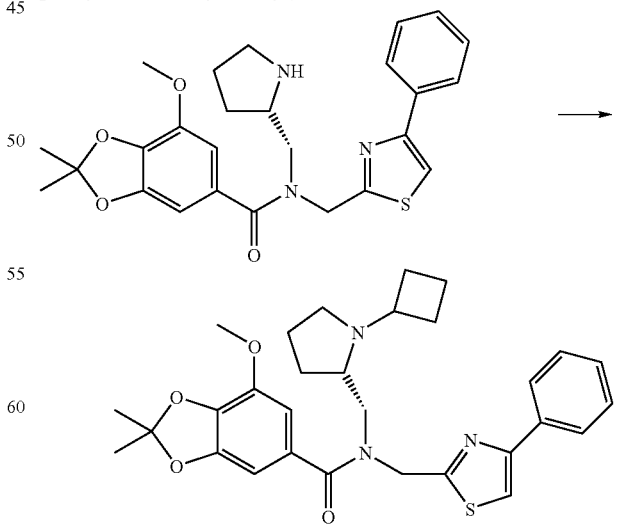

Experimental conditions analogous to Example 1, from 0.1 g (0.21 mmol) of 7-methoxy-2,2-dimethyl-benzo[1,3]dioxole-5-carboxylic acid (5-phenyl-thiazol-2-ylmethyl)-(S)-1-pyrrolidin-2-ylmethyl-amide, 41 mg (0.58 mmol) of butanone, 0.12 mg (0.58 mmol) of sodium cyanoborohydride in 3 mL dichloromethane. The crude product was purified to yield 51 mg of product as viscous oil. LC-MSD, m/z for $C_{30}H_{35}N_3O_4$ [M+H]+: 534.7, [M+2H]+: 535.7. LC retention time on HPLC, C18 column gradient 20-95% acetonitrile with 0.1% TFA in 4 min: 1.816 min. $^1$H NMR (400 MHz, CDCl$_3$): δ 1.4-2.3 (m, 16 H), 2.4 (m, 1 H), 2.7-4.0 (m, 8 H), 5.1 (s, 2 H), 6.62 (s, 1 H), 6.72 (s, 1H), 7.3-7.5 (m, 4 H), 7.8-7.9 (m, 2 H).

Example 51

This example illustrates the preparation of 7-Methoxy-2,2-dimethyl-benzo[1,3]dioxole-5-carboxylic acid (octahydro-indol-2-ylmethyl)-(4-phenyl-thiazol-2-ylmethyl)-amide.

Step 1: (2S,3aS,7aS)-3a,7a-Dimethyl-2-{[(4-phenyl-thiazol-2-ylmethyl)-amino]-methyl}-octahydro-indole-1-carboxylic acid tert-butyl ester.

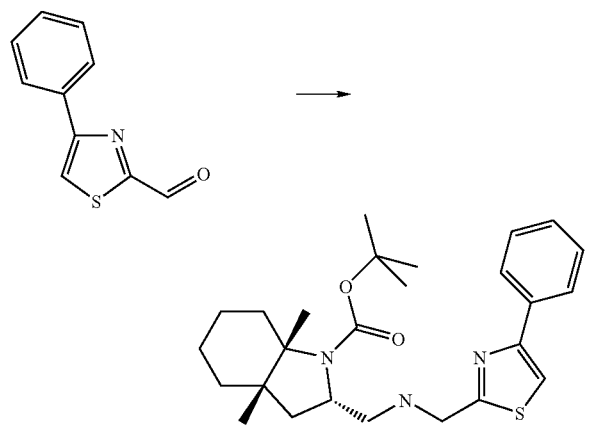

Experimental conditions analogous to Example 1, from 0.26 mg (1.05 mmol) of (S)-2-aminomethyl-octahydro-indole-1-carboxylic acid tert-butyl ester, 0.18 mg (1.0 mmol) of 4-phenyl-thiazole-2-carbaldehyde, 0.42 mg (2.0 mmol) of sodium triacethoxy borohydride in 10 mL dichloromethane. The crude product was purified by prep-HPLC to yield 110 mg of colorless viscous oil. LC-MSD, m/z for $C_{24}H_{33}N_3O_2S$ [M+H]+: 428.6, [M+2H]+: 429.6. LC retention time on HPLC, C18 column gradient 20-95% acetonitrile with 0.1% TFA in 4 min: 2.352 min.

Step 2: 7-Methoxy-2,2-dimethyl-benzo[1,3]dioxole-5-carboxylic acid [(2S,3aS,7aS)-1-(octahydro-indol-2-yl)methyl]-(4-phenyl-thiazol-2-ylmethyl)-amide.

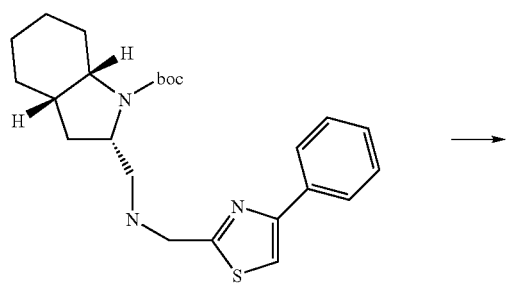

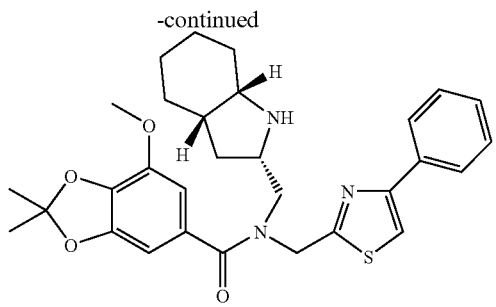

Experimental conditions analogous to described for Example 1, from 0.11 g (0.258 mmol) of (2S,3aS,7aS)-3a,7a-dimethyl-2-{[(4-phenyl-thiazol-2-ylmethyl)-amino]-methyl}-octahydro-indole-1-carboxylic acid tert-butyl ester, 97 mg (0.396 mmol) of 7-methoxy-2,2-dimethyl-benzo[1,3]dioxole-5-carbonyl chloride, 73 mg (0.61 mmol) of triethylamine in 5 mL dichloromethane. The crude product was purified by prep-HPLC to yield 50 mg of yellowish viscous oil. The deprotection was conducted by the addition of 0.5 mL TFA into the crude dissolved in 3 mL of dichloromethane. The crude was purified by prep-HPLC to yield 22 mg product. LC-MSD, m/z for $C_{30}H_{35}N_3O_4$ [M+H]+: 534.6, [M+2H]+: 535.6. LC retention time on HPLC, C18 column gradient 20-95% acetonitrile with 0.1% TFA in 4 min: 2.359 min. $^1$H NMR (400 MHz, CDCl$_3$): δ 1.4-2.0 (m, 15 H), 2.18 (m, 1 H), 2.46 (m, 1 H), 3.5-3.8 (m, 5 H), 4.3-4.6 (m, 3 H), 5.0 (m, 2 H), 6.74 (s, 1 H), 6.96 (s, 1H), 7.3-7.5 (m, 4 H), 7.8-7.9 (m, 2 H).

Example 52

This example illustrates the preparation of 7-Methoxy-2,2-dimethyl-benzo[1,3]dioxole-5-carboxylic acid ((S)-1-azetidin-3-ylmethyl-pyrrolidin-2-ylmethyl)-(4-phenyl-thiazol-2-ylmethyl)-amide.

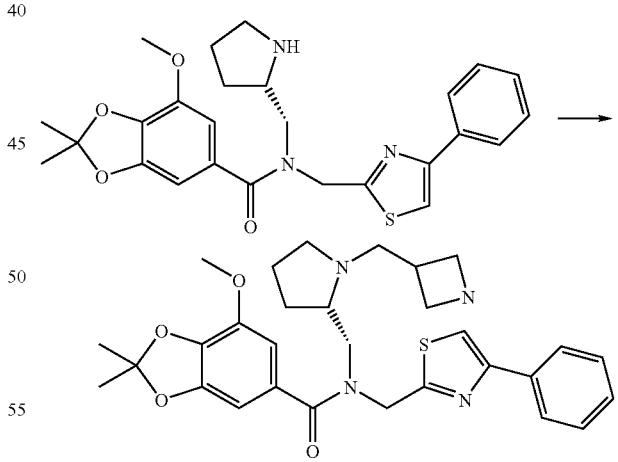

In 3 mL dichloromethane was dissolved 90 mg (0.20 mmol) of 7-methoxy-2,2-dimethyl-benzo[1,3]dioxole-5-carboxylic acid (4-phenyl-thiazol-2-ylmethyl)-(S)-1-pyrrolidin-2-ylmethyl-amide, followed by addition of 0.14 g (0.76 mmol) of Boc-azetidine carboxaldehyde and 0.42 g (2 mmol) of sodium triacethoxyborohydride. The mixture was stirred for 1 hour at r.t. and then quenched by addition of 5 mL saturated sodium bicarbonate. 50 mL of water was added and the mixture was extracted with 50 mL of dichloromethane.

The organic layer was dried over magnesium sulfate and evaporated in vacuum to yield colorless oil. The crude was dissolved in 3 mL of dichloromethane followed by addition of 0.5 mL of trifluoroacetic acid. The mixture was stirred for 30 minutes and reaction was quenched by addition of 5 mL of saturated sodium bicarbonate. 20 mL of water was added followed by extraction with 20 mL of dichloromethane. The organic layer was dried over magnesium sulfate and evaporated in vacuum. The crude product was purified by prep HPLC to yield 24 mg of product colorless oil. LC-MSD, m/z for $C_{30}H_{36}N_4O_4S$ [M+H]+: 549.7, [M+2H]+: 550.7. LC retention time on HPLC, C18 column gradient 20-95% acetonitrile with 0.1% TFA in 4 min: 1.609 min. $^1$H NMR (400 MHz, CDCl$_3$): δ 1.67 (s, 6 H), 1.7-2.5 (m, 7 H), 2.8-3.0 (m, 4 H), 3.40 (s, 3 H), 3.6-3.9 (m, 5 H), 5.1 (s, 2 H), 6.6 (s, 1 H), 6.7 (s, 1H), 7.35-7.6 (m, 4 H), 7.8-8.0 (m, 2 H).

Example 53

This example illustrates 7-Methoxy-2,2-dimethyl-benzo[1,3]dioxole-5-carboxylic acid [1-(3-aza-bicyclo[3.2.1]oct-8-ylmethyl)-pyrrolidin-2-ylmethyl]-benzo[b]thiophen-2-yl-methyl-amide.

Step 1: (S)-2-{[(Benzo[b]thiophen-2-ylmethyl)-amino]-methyl}-pyrrolidine-1-carboxylic acid tert-butyl ester.

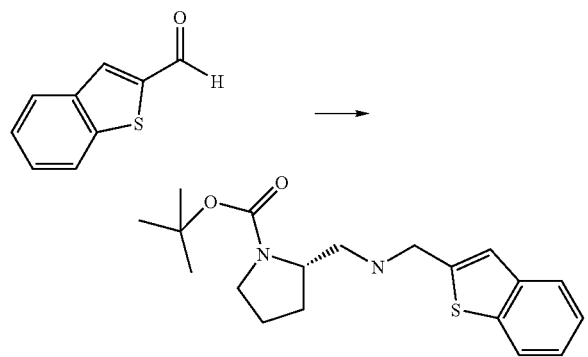

Experimental conditions analogous to Example 1, from 0.17 g (0.85 mmol) of (S)-2-aminomethyl-pyrrolidine-1-carboxylic acid tert-butyl ester, 0.13 g (0.85 mmol) of benzo[b]thiophene-2-carbaldehyde, 0.4 g (1.81 mmol) of sodium triacethoxyborohydride in 8 mL dichloromethane. The crude product was purified by prep-HPLC to yield 90 mg of product as yellow viscous oil. LC-MSD, m/z for $C_{19}H_{26}N_2O_2S$ [M+H]+: 347.5, [M+2H]+: 348.5. LC retention time on HPLC, C18 column gradient 20-95% acetonitrile with 0.1% TFA in 4 min: 1.784 min Step 2: 7-Methoxy-2,2-dimethyl-benzo[1,3]dioxole-5-carboxylic acid benzo[b]thiophen-2-ylmethyl-(S)-1-pyrrolidin-2-ylmethyl-amide.

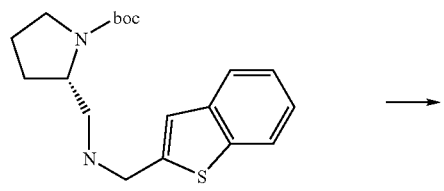

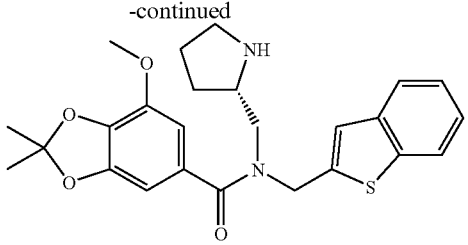

Experimental conditions analogous to Example 1, from 90 mg (0.260 mmol) of (S)-2-{[(benzo[b]thiophen-2-ylmethyl)-amino]-methyl}-pyrrolidine-1-carboxylic acid tert-butyl ester, 70 mg (0.289 mmol) of 7-methoxy-2,2-dimethyl-benzo[1,3]dioxole-5-carbonyl chloride, 35 mg (0.29 mmol) of triethylamine in 5 mL dichloromethane. The crude product was purified by prep-HPLC to yield 120 mg of colorless solid. The deprotection was conducted by the addition of 0.5 mL TFA into the product that was dissolved in 3 mL of dichloromethane. The crude was used for the next step without further purification. LC-MSD, m/z for $C_{30}H_{38}N_2O_4$ [M+H]+: 453.6, [M+2H]+: 454.6. LC retention time on HPLC, C18 column gradient 20-95% acetonitrile with 0.1% TFA in 4 min: 1.912 min Step 3: 7-Methoxy-2,2-dimethyl-benzo[1,3]dioxole-5-carboxylic acid [1-(3-aza-bicyclo[3.2.1]oct-8-ylmethyl)-(S)-1-pyrrolidin-2-ylmethyl]-benzo[b]thiophen-2-ylmethyl-amide.

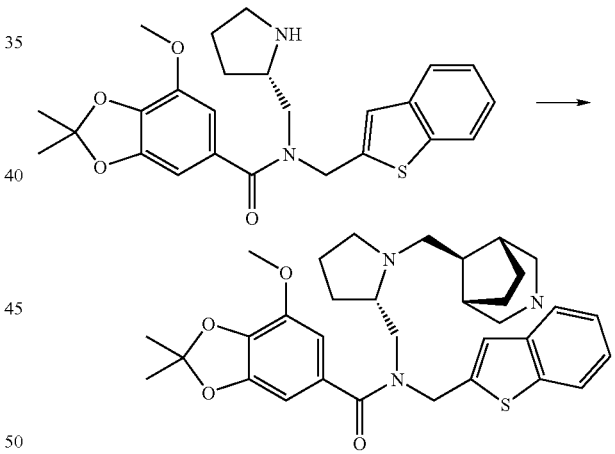

Experimental conditions analogous to Example 1, from 0.12 g (0.27 mmol) of 7-methoxy-2,2-dimethyl-benzo[1,3]dioxole-5-carboxylic acid benzo[b]thiophen-2-ylmethyl-(S)-1-pyrrolidin-2-ylmethyl-amide, 97 mg (0.41 mmol) of 8-formyl-3-aza-bicyclo[3.2.1]octane-3-carboxylic acid tert-butyl ester in 2 mL dichloromethane. The deprotection was conducted by the addition of 0.5 mL TFA into the crude dissolved in 3 mL of dichloromethane. The crude product was purified to yield 44 mg of colorless viscous oil. LC-MSD, m/z for $C_{34}H_{42}N_4O_4$ [M+H]+: 576.7, [M+2H]+: 577.7. LC retention time on HPLC, C18 column gradient 20-95% acetonitrile with 0.1% TFA in 4 min: 1.735 min. $^1$H NMR (400 MHz, CD$_3$OD): δ 1.1-1.4 (m, 4 H), 1.5-2.3 (m, 19 H), 2.7-3.5 (m, 5 H), 3.82 (s, 3 H) 5.1 (s, 2 H), 6.58 (s, 1 H), 6.63 (s, 1H), 7.2-7.4 (m, 3 H), 7.7-7.9 (m, 2 H).

Example 54

This example illustrates the preparation of 7-Methoxy-2,2-dimethyl-benzo[1,3]dioxole-5-carboxylic acid [1-(3-aza-bicyclo[3.2.1]oct-8-ylmethyl)-(S)-1-pyrrolidin-2-ylmethyl]-benzo[b]thiophen-2-ylmethyl-amide.

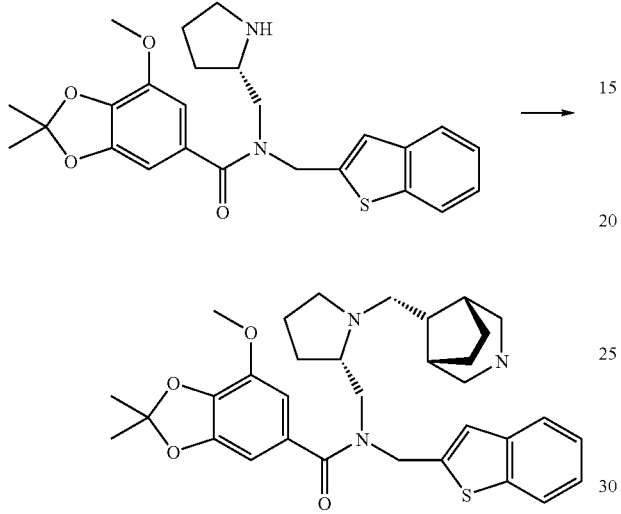

Experimental conditions analogous to Example 1, from 0.12 g (0.27 mmol) of 7-methoxy-2,2-dimethyl-benzo[1,3]dioxole-5-carboxylic acid benzo[b]thiophen-2-ylmethyl-(S)-1-pyrrolidin-2-ylmethyl-amide, 2 mL dichloromethane, 97 mg (0.41 mmol) of 8-formyl-3-aza-bicyclo[3.2.1]octane-3-carboxylic acid tert-butyl ester. The deprotection was conducted by the addition of 0.5 mL TFA into the crude which was dissolved in 3 mL of dichloromethane. The crude product was purified to yield 44 mg of colorless viscous oil. LC-MSD, m/z for $C_{33}H_{41}N_3O_4S$ [M+H]+: 576.7, [M+2H]+: 577.7. LC retention time on HPLC, C18 column gradient 20-95% acetonitrile with 0.1% TFA in 4 min: 1.769 min. $^1$H NMR (400 MHz, CD$_3$OD): δ 1.1-1.3 (m, 4 H), 1.4-2.3 (m, 19 H), 2.6-3.6 (m, 5 H), 3.80 (s, 3 H) 5.1 (s, 2 H), 6.56 (s, 1 H), 6.64 (s, 1H), 7.2-7.4 (m, 3 H), 7.7-7.9 (m, 2 H).

Example 55

This example illustrates 7-Methoxy-2,2-dimethyl-benzo[1,3]dioxole-5-carboxylic acid (2-phenyl-thiazol-4-ylmethyl)-pyrrolidin-2-ylmethyl-amide Step 1: (S)-2-{[(2-Phenyl-thiazol-4-ylmethyl)-amino]-methyl}-pyrrolidine-1-carboxylic acid tert-butyl ester

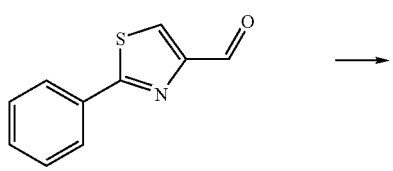

Experimental conditions analogous to Example 1, from 0.66 g (3.3 mmol) of 2-aminomethyl-pyrrolidine-1-carboxylic acid tert-butyl ester, 0.56 g (3.0 mmol) of 2-phenyl-thiazole-4-carbaldehyde, 1.46 g (6.6 mmol) of sodium triacethoxyborohydride in 10 mL dichloromethane. The crude product was purified by flash chromatograph to yield 0.99 mg of colorless viscous oil. LC-MSD, m/z for $C_{20}H_{27}N_3O_2S$ [M+H]+: 374.5 LC retention time on HPLC, C18 column gradient 20-95% acetonitrile with 0.1% TFA in 4 min: 2.011 min.

Step 2: 7-Methoxy-2,2-dimethyl-benzo[1,3]dioxole-5-carboxylic acid (2-phenyl-thiazol-4-ylmethyl)-(S)-1-pyrrolidin-2-ylmethyl-amide.

Experimental conditions analogous to Example 1, from 96 mg (0.28 mmol) of (S)-2-{[(2-phenyl-thiazol-4-ylmethyl)-amino]-methyl}-pyrrolidine-1-carboxylic acid tert-butyl ester, 72 mg (0.30 mmol) of 7-methoxy-2,2-dimethyl-benzo[1,3]dioxole-5-carbonyl chloride, 39 mg (0.30 mmol) of triethylamine and 5 mL dichloromethane. The crude product was purified by flash chromatograph to yield 110 mg of yellow solid. The deprotection was conducted by the addition of 1.5 mL TFA into the crude dissolved in 10 ml of dichloromethane. The crude was purified by prep-HPLC to yield 70 mg of product LC-MSD, m/Z for $C_{26}H_{29}N_3O_4S$ [M+H]+: 480.6, [M+2H]+: 481.6. LC retention time on HPLC, C18 column gradient 20-95% acetonitrile with 0.1% TFA in 4 min: 1.934 min. $^1$H NMR (400 MHz, CD$_3$OD): δ 1.67 (s, 6 H), 1.7-1.9 (m, 1 H), 1.9-2.3 (m, 3 H), 3.2-3.5 (m, 2 H), 3.6-3.7 (m, 1 H), 3.74 (s, 3 H), 3.8-3.9 (m, 1 H), 4.0-4.1 (m, 1H), 4.73 (s, 2 H), 6.82 (s, 1 H), 7.05 (s, 1H), 7.42 (s, 1 H), 7.44-7.50 (m, 3 H), 7.9-8.0 (m, 2 H).

Example 56

This example illustrates 7-Methoxy-2,2-dimethyl-benzo[1,3]dioxole-5-carboxylic acid ((S)-1-methyl-pyrrolidin-2-ylmethyl)-(2-phenyl-thiazol-4-ylmethyl)-amide.

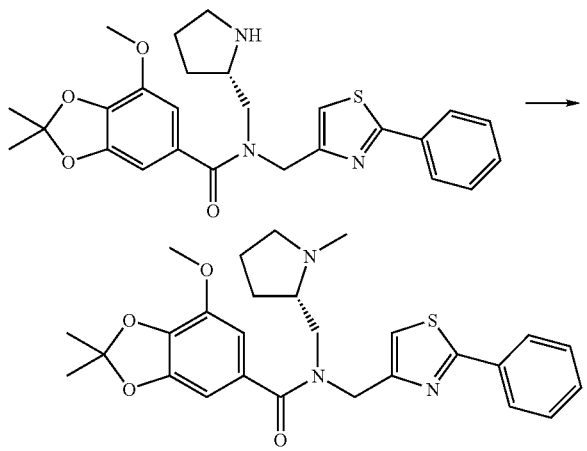

In 5 mL methanol was dissolved 60 mg (0.13 mmol) of 7-methoxy-2,2-dimethyl-benzo[1,3]dioxole-5-carboxylic acid (2-phenyl-thiazol-4-ylmethyl)-(S)-1-pyrrolidin-2-ylmethyl-amide. 50 mg of paraformaldehyde and 50 mg of sodium triacethoxyborohydride (0.83 mmol) were added, and the mixture was stirred at r.t. for 3 hours. The reaction was quenched by adding 10 mL of saturated sodium bicarbonate solution and 50 mL of water then extracted with 50 mL of chloroform. The organic layer was dried over anhydrous magnesium sulfate and concentrated to yield yellowish oil. The crude was purified by prep-HPLC to yield 20 mg of product. LC-MSD, m/z for $C_{27}H_{31}N_3O_4S$ [M+H]+: 494.6, [M+2H]+: 495.6. LC retention time on HPLC, C18 column gradient 20-95% acetonitrile with 0.1% TFA in 4 min: 2.203 min. $^1$H NMR (400 MHz, CD$_3$OD): δ 1.68 (s, 6 H), 1.8-2.3 (m, 4 H), 2.99 (s, 3 H), 3.1-3.2 (m, 1 H), 3.6-3.9 (m, 6 H), 4.0-4.1 (m, 1 H), 4.7-4.9 (m, 2 H), 6.85 (s, 1 H), 7.07 (s, 1H), 7.45 (s, 1 H), 7.46-7.52 (m, 3 H), 7.94-8.0 (m, 2 H).

Example 57

This example illustrates the preparation of 7-Methoxy-2,2-dimethyl-benzo[1,3]dioxole-5-carboxylic acid benzofuran-2-ylmethyl-[(2S,3aS,7aS)-1-(octahydro-indol-2-yl)methyl]-amide.

Step 1: (2S,3aS,7aS)-2-{[(Benzofuran-2-ylmethyl)-amino]-methyl}-octahydro-indole-1-carboxylic acid tert-butyl ester.

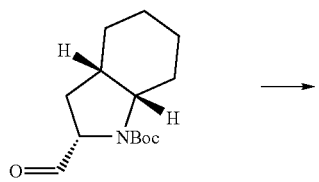

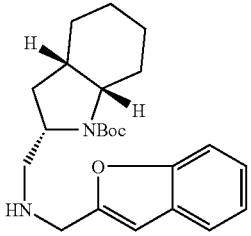

To a solution of 31 mg (0.12 mmol) of (2S,3aS,7aS)-2-formyl-octahydro-indole-1-carboxylic acid tert-butyl ester in 1 mL dichloromethane, 18 mg (0.12 mmol) of c-benzofuran-2-yl-methylamine 40 mg (0.18 mmol) of sodium triacetoxyborohydride were added and the mixture was stirred for 3 hours, then diluted with 5 mL dichloromethane and quenched with 3 mL of aqueous sodium bicarbonate. The aqueous layer was extracted once with dichloromethane and the combined organic layers were dried with anhydrous magnesium sulfate, evaporated in vacuum and purified using reverse phase HPLC, mobile phase with a gradient 15-80% acetonitrile in 50 min. Fractions containing pure product were evaporated in vacuum to yield, 53 mg of white solid as the trifluoroacetate. LC-MSD, m/z for $C_{23}H_{32}N_2O_3$ [M+H]+: 385.2.

Step 2: 7-Methoxy-2,2-dimethyl-benzo[1,3]dioxole-5-carboxylic acid benzofuran-2-ylmethyl-[(2S,3aS,7aS)-1-(octahydro-indol-2-yl)methyl]-amide.

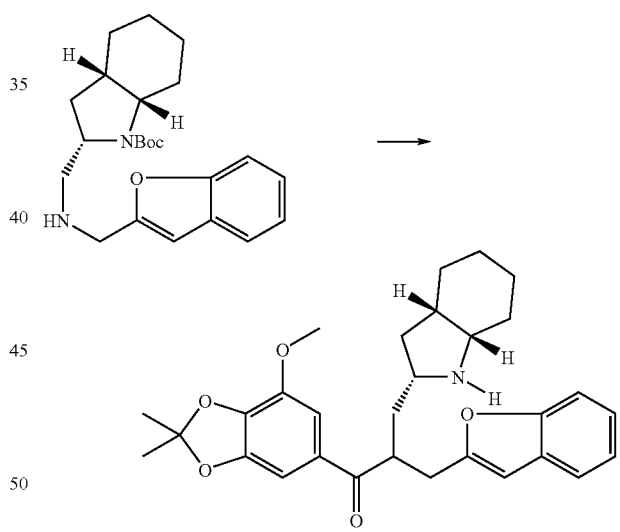

To a solution of 45 mg (0.09 mmol) of (2S,3aS,7aS)-2-{[(benzofuran-2-ylmethyl)-amino]-methyl}-octahydro-indole-1-carboxylic acid tert-butyl ester trifluoroacetic acid salt in 1 mL dichloromethane, 28 µL (0.20 mmol) of triethylamine and 23 mg (0.10 mmol) of 7-methoxy-2,2-dimethyl-benzo[1,3]dioxole-5-carbonyl chloride were added at r.t. Stirring at r.t. for 1 hour was followed by the addition of 0.1 mL trifluoroacetic acid; 2 hours thereafter the solution was evaporated in vacuum and purified using reverse phase HPLC, mobile phase with a gradient 15-80% acetonitrile in 50 min. Fractions containing pure product were evaporated, the residue was dissolved in dichloromethane, which was washed with aqueous sodium bicarbonate, dried with anhydrous magnesium sulfate and evaporated in vacuum to yield 13 mg of the product as the free base off-white Solid. LC-MSD, m/z for $C_{29}H_{34}N_2O_5$ [M+H]$^+$: 491.2. $^1$H NMR (400 MHz, CDCl$_3$): δ 1.2-2.3 (m, 11 H), 1.7 (s, 6 H), 3.2-3.9 (m, 4 H), 3.9 (s, 3 H), 4.7-4.9 (m, 1 H), 4.9-5.0 (m, 1 H), 6.7 (s, 1H), 6.7-6.9 (m, 2H), 7.2-7.3 (m, 2H), 7.4-7.5 (m, 1 H), 7.5-7.6 (m, 1 H).

Example 58

This example illustrates the preparation of 7-Methoxy-2,2-dimethyl-benzo[1,3]dioxole-5-carboxylic acid benzofuran-2-ylmethyl-((S)-1-cyclobutyl-pyrrolidin-2-ylmethyl)-amide.

Step 1: (S)-2-{[(Benzofuran-2-ylmethyl)-amino]-methyl}-pyrrolidine-1-carboxylic acid tert-butyl ester.

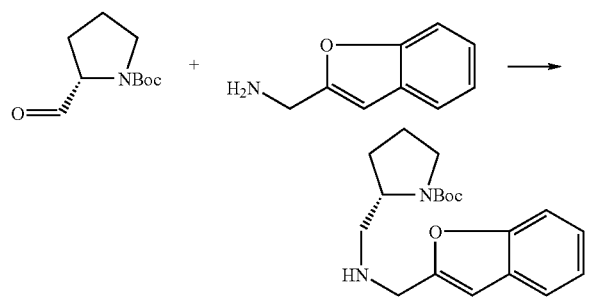

Experimental conditions were analogous to Example 1. 0.16 g (0.80 mmol) of (S)-2-formyl-pyrrolidine-1-carboxylic acid tert-butyl ester, 0.11 mg (0.80 mmol) of C-benzofuran-2-yl-methylamine, and 0.25 g (1.2 mmol) of sodium triacetoxyborohydride were dissolved in 5 mL dichloromethane. Product was purified using reverse phase HPLC, mobile phase with a gradient 15-80% acetonitrile in 50 min. Fractions containing pure product were evaporated to yield 278 mg of the trifluoroacetate as an off-white oil. LC-MSD, m/z for $C_{29}H_{26}N_2O_3$ [M+H]$^+$: 331.2

Step 2: 7-Methoxy-2,2-dimethyl-benzo[1,3]dioxole-5-carboxylic acid benzofuran-2-ylmethyl-((S)-1-cyclobutyl-pyrrolidin-2-ylmethyl)-amide.

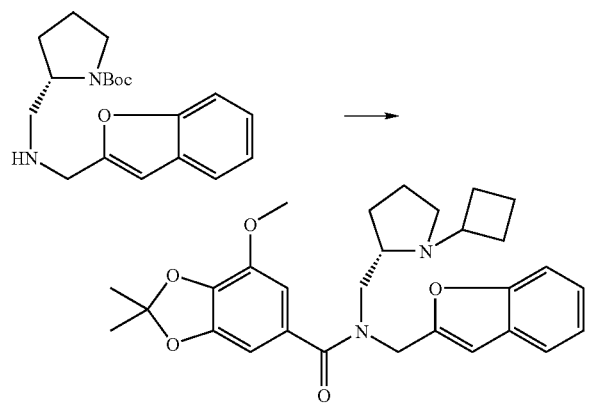

Experimental conditions analogous to Example 15, from 0.27 g (0.62 mmol) of (S)-2-{[(benzofuran-2-ylmethyl)-amino]-methyl}-pyrrolidine-1-carboxylic acid tert-butyl ester trifluoroacetic acid salt, was dissolved 1 mL dichloromethane, 216 μL (1.55 mmol) of triethylamine, and 0.16 g (0.68 mmol) of 7-methoxy-2,2-dimethyl-benzo[1,3]dioxole-5-carbonyl chloride were added to this mixture. The crude mixture was filtered through silica and the Boc-deprotection was conducted in 4 mL 10% trifluoroacetic acid/dichloromethane in 2 hours, followed by aqueous sodium bicarbonate quench and submitting the crude material to reductive amination reaction in dichloromethane using 0.24 g (3.1 mmol) of cyclobutanone and 0.657 g (3.1 mmol) of sodium triacetoxyborohydride. After 5 hours the reaction was quenched with aqueous sodium bicarbonate and di-tert-butyl dicarbonate. The residue from the organic layer was purified using flash chromatography (7N ammonia in methanol, 0-3% in dichloromethane), gave 49 mg off-white solid as a free base solid. LC-MSD, m/z for $C_{29}H_{34}N_2O_5$ [M+H]$^+$: 491.2. $^1$H NMR (400 MHz, CDCl$_3$/HCl): δ 1.7 (s, 6 H), 1.8-2.1 (m, 6 H), 2.1-2.2 (m, 1 H), 2.3-2.4 (m, 1 H), 2.5-2.7 (m, 2 H), 2.8-2.9 (m, 1 H), 3.5-3.7 (m, 1 H), 3.7-3.9 (m, 3 H), 3.9 (s, 3 H), 4.0-4.1 (m, 1 H), 4.8-5.0 (m, 2 H), 6.8 (s, 1H), 6.9 (s, 1 H), 7.0 (s, 1 H), 7.2-7.3 (m, 2H), 7.4-7.5 (m, 1 H), 7.5-7.6 (m, 1 H), 12.0-12.1 (bs, 1 H).

Example 59

This example illustrates the preparation of 7-Methoxy-2,2-dimethyl-benzo[1,3]dioxole-5-carboxylic acid ((S)-1-cyclobutyl-pyrrolidin-2-ylmethyl)-naphthalen-2-ylmethyl-amide.

Step 1: (S)-2-{[(Naphthalen-2-ylmethyl)-amino]-methyl}-pyrrolidine-1-carboxylic acid tert-butyl ester.

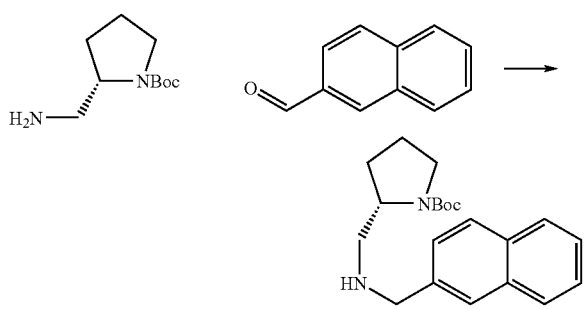

Experimental conditions were analogous to Example 1. 0.27 g (1.76 mmol) of naphthalene-2-carbaldehyde, 0.35 g (1.76 mmol) of (S)-2-aminomethyl-pyrrolidine-1-carboxylic acid tert-butyl ester, were dissolved in 10 mL dichloromethane, and 0.55 g (2.64 mmol) of sodium triacetoxyborohydride was added. The reaction was quenched with aqueous sodium bicarbonate. The residue from the organic layer was purified using flash chromatography (ethyl acetate in hexane), yielded to 350 mg of the free base as colorless oil. LC-MSD, m/z for $C_{21}H_{28}N_2O_2$ [M+H]$^+$: 341.2

Step 2: 7-Methoxy-2,2-dimethyl-benzo[1,3]dioxole-5-carboxylic acid ((S)-1-cyclobutyl-pyrrolidin-2-ylmethyl)-naphthalen-2-ylmethyl-amide.

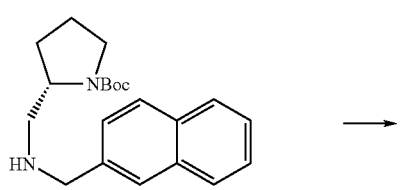

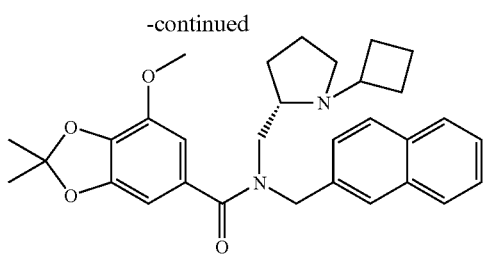

Experimental conditions analogous Example 58, from 0.35 g (1.01 mmol) of (S)-2-{[(naphthalen-2-ylmethyl)-amino]-methyl}-pyrrolidine-1-carboxylic acid tert-butyl ester, 10 mL dichloromethane, 169 µL (1.21 mmol) of triethylamine, and 0.27 g (1.12 mmol) of 7-methoxy-2,2-dimethyl-benzo[1,3]dioxole-5-carbonyl chloride. The crude mixture was filtered through silica and the compound was deprotected in 10 mL 10% trifluoroacetic acid/dichloromethane in 1.5 hours. The reaction mixture was treated with aqueous sodium bicarbonate, and extracted with dichloromethane. The crude material was dissolved in 10 mL of dichloromethane, to this mixture was added 0.21 g (3.0 mmol) of cyclobutanone and 0.636 g (3.0 mmol) of sodium triacetoxyborohydride. After overnight the reaction was quenched with aqueous sodium bicarbonate and di-tert-butyl dicarbonate. The organic layer was separated, the residue was purified using flash chromatography (7N ammonia in methanol, 0-3% in dichloromethane), gave 76 mg of off white solid as a free base. LC-MSD, m/z for $C_{31}H_{36}N_2O_4$ [M+H]$^+$: 501.7. $^1$H NMR (400 MHz, CDCl$_3$/HCl): δ 1.7 (s, 6 H), 1.9-2.7 (m, 10 H), 2.8-3.0 (m, 1 H), 3.5-3.7 (m, 1 H), 3.8 (s, 3 H), 3.8-4.0 (m, 4 H), 4.9-5.0 (m, 1 H), 5.2-53 (m, 1 H), 6.7 (s, 1H), 6.8 (s, 1 H), 7.2-7.3 (m, 1H), 7.4-7.5 (m, 2 H), 7.7 (s, 1 H), 7.8-7.9 (m, 3 H), 12.2-12.3 (m, 1 H).

Example 60

This example illustrates the preparation of 7-Methoxy-2,2-dimethyl-benzo[1,3]dioxole-5-carboxylic acid benzo[b]thiophen-2-ylmethyl-((S)-1-cyclobutyl-pyrrolidin-2-ylmethyl)-amide.

Step 1: (S)-2-{[(Benzo[b]thiophen-2-ylmethyl)-amino]-methyl}-pyrrolidine-1-carboxylic acid tert-butyl ester.

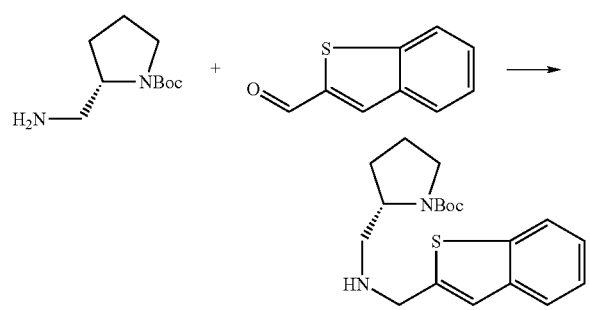

Experimental conditions were analogous to Example 1, from 0.28 g (1.78 mmol) of benzo[b]thiophene-2-carbaldehyde, 0.35 g (1.78 mmol) of (S)-2-aminomethyl-pyrrolidine-1-carboxylic acid tert-butyl ester, 10 mL dichloromethane, and 565 mg (2.64 mmol) of sodium triacetoxyborohydride. The reaction was quenched with aqueous sodium bicarbonate. The residue from the organic layer was purified using flash chromatography (ethyl acetate in hexane). The reaction gave 291 mg of the free base as a colorless oil. LC-MSD, m/z for $C_{19}H_{26}N_2O_2S$ [M+H]$^+$: 347.5

Step 2: 7-Methoxy-2,2-dimethyl-benzo[1,3]dioxole-5-carboxylic acid benzo[b]thiophen-2-ylmethyl-((S)-1-cyclobutyl-pyrrolidin-2-ylmethyl)-amide.

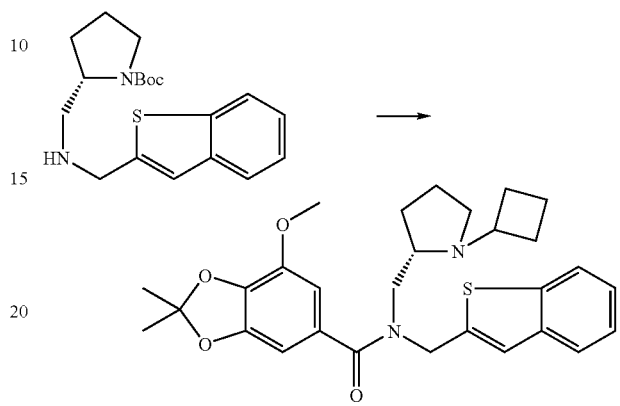

Experimental conditions were analogous to Example 58, from 0.29 g (0.84 mmol) of (S)-2-{[(benzo[b]thiophen-2-ylmethyl)-amino]-methyl}-pyrrolidine-1-carboxylic acid tert-butyl ester, 10 mL dichloromethane, 141 µL (1.01 mmol) of triethylamine, and 0.22 mg (0.92 mmol) of 7-methoxy-2,2-dimethyl-benzo[1,3]dioxole-5-carbonyl chloride. The crude mixture was filtered through silica and the Boc-deprotection was conducted in 10 mL 10% trifluoroacetic acid/dichloromethane in 2 hours, followed by aqueous sodium bicarbonate quench. The crude material from organic layer was alkylated in 5 mL dichloromethane, with 0.2 g (2.5 mmol) of cyclobutanone and 0.53 mg (2.5 mmol) of sodium triacetoxyborohydride. After 2 days the reaction was quenched with aqueous sodium bicarbonate and di-tert-butyl dicarbonate. The residue from the organic layer was purified using reverse phase HPLC, mobile phase with a gradient 15-80% acetonitrile in 50 min., gave 92 mg of off-white solid as the free base. LC-MSD, m/z for $C_{29}H_{34}N_2O_4S$ [M+H]$^+$: 507.6. $^1$H NMR (400 MHz, CDCl$_3$): δ 1.5-3.5 (m, 16 H), 1.7 (s, 6 H), 3.8 (bs, 3 H), 5.0 (bs, 2 H), 6.6 (s, 1 H), 6.7 (s, 1 H), 7.2 (bs, 1 H), 7.3-7.4 (m, 2 H), 7.7-7.8 (m, 1 H), 7.8-7.9 (m, 1 H).

Example 61

This example illustrates the preparation of 7-Methoxy-2,2-dimethyl-benzo[1,3]dioxole-5-carboxylic acid benzo[b]thiophen-2-ylmethyl-[(2S,3aS,7aS)-1-(octahydro-indol-2-yl)methyl]-amide.

Step 1: (2S,3aS,7aS)-2-{[(Benzo[b]thiophen-2-ylmethyl)-amino]-methyl}-octahydro-indole-1-carboxylic acid tert-butyl ester.

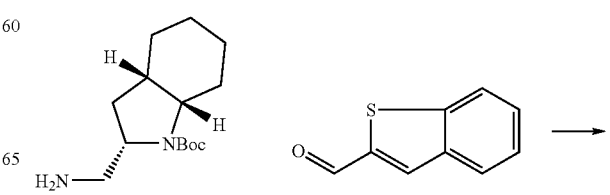

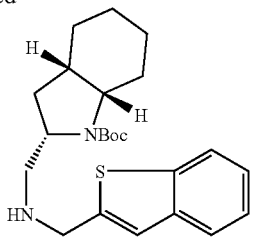

Experimental conditions analogous to Example 1, from 0.1 g (0.63 mmol) of benzo[b]thiophene-2-carbaldehyde, 0.16 g (0.63 mmol) of (2S,3aS,7aS)-2-aminomethyl-octahydro-indole-1-carboxylic acid tert-butyl ester, 10 mL dichloromethane, and 0.2 g (0.94 mmol) of sodium triacetoxyborohydride. The reaction was quenched with aqueous sodium bicarbonate. The residue from the organic layer was purified using flash chromatography (ethyl acetate in hexane), yield 130 mg of the free base as colorless oil. LC-MSD, m/z for $C_{23}H_{32}N_2O_2S$ [M+H]$^+$: 401.6, [M+H-isobutylene]$^+$: 345.5.

Step 2: 7-Methoxy-2,2-dimethyl-benzo[1,3]dioxole-5-carboxylic acid benzo[b]thiophen-2-ylmethyl-[(2S,3aS,7aS)-1-(octahydro-indol-2-yl)methyl]-amide.

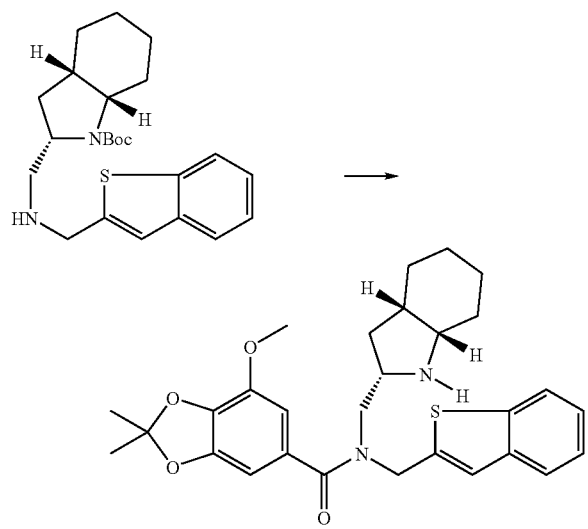

Experimental conditions analogous to Example 1, from 0.12 (0.31 mmol) of (2S,3aS,7aS)-2-{[(benzo[b]thiophen-2-ylmethyl)-amino]-methyl}-octahydro-indole-1-carboxylic acid tert-butyl ester, 3 mL dichloromethane, 52 μL (0.37 mmol) of triethylamine, and 83 mg (0.34 mmol) of 7-methoxy-2,2-dimethyl-benzo[1,3]dioxole-5-carbonyl chloride and 0.4 mL trifluoroacetic acid. The compound was purified using reverse phase HPLC, mobile phase with a gradient 15-80% acetonitrile in 50 min, gave 104 mg of the product as the free base as an off-white solid. LC-MSD, m/z for $C_{29}H_{34}N_2O_4S$ [M+H]$^+$: 507.6. $^1$H NMR (400 MHz, CDCl$_3$/HCl): δ 1.4-2.0 (m, 8 H), 1.7 (s, 6 H), 2.1-2.2 (m, 1 H), 2.4-2.5 (m, 1 H), 3.2 (bs, 1 H), 3.3-3.4 (m, 1 H), 3.7-3.8 (m, 1 H), 3.8 (s, 3 H), 4.2-4.4 (m, 2 H), 4.9-5.2 (m, 2 H), 6.8 (s, 1 H), 7.1 (s, 1 H), 7.3-7.4 (m, 2 H), 7.7-7.8 (m, 2 H), 7.9 (bs, 1 H), 11.6-11.8 (bs, 1 H).

Example 62

This example illustrates the preparation of 7-Methoxy-2,2-dimethyl-benzo[1,3]dioxole-5-carboxylic acid ((S)-1-cyclobutyl-pyrrolidin-2-ylmethyl)-isoquinolin-3-ylmethylamide.

Step 1: Isoquinoline-3-carboxylic acid methoxy-methyl-amide.

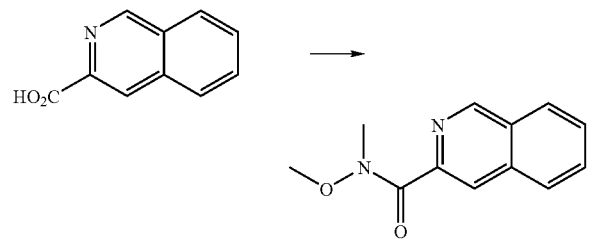

In 50 mL of acetonitrile was dissolved 0.49 g (2.60 mmol) of isoquinoline-3-carboxylic acid monohydrate. To this 0.28 g (2.87 mmol) of O,N-dimethyl-hydroxylamine hydrochloride, 0.4 mL (2.87 mmol) triethylamine and 0.921 g (3.13 mmol) of 4-(4,6-dimethoxy-[1,3,5]triazin-2-yl)-4-methyl-morpholin-4-ium chloride hydrate were added and stirred for 2 days and then evaporated. A mixture of dichloromethane and water was added to it and the organic layer was evaporated and purified using flash chromatography (0-20% methanol in dichloromethane). Fractions containing pure product were evaporated to yield 210 mg of the free base as a white solid. LC-MSD, m/z for $C_{12}H_{12}N_2O_2$ [M+H]$^+$: 217.4, [M+Na]$^+$: 239.4

Step 2: Isoquinoline-3-carbaldehyde

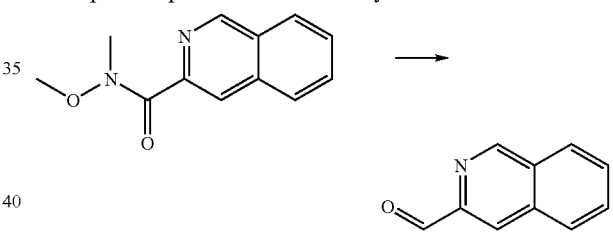

In 5 mL dry tetrahydrofuran 0.11 g (0.52 mmol) of isoquinoline-3-carboxylic acid methoxy-methyl-amide was dissolved, and cooled down to −78° C. under the atmosphere of nitrogen. 0.57 mL of 1M diisobutylaluminum hydride solution in heptane was added slowly. After the addition was complete, the solution was allowed to warm up to 0° C. over 2 hours and was quenched with ethyl acetate, and water was added, and extracted with dichloromethane. The organic solution was dried with anhydrous magnesium sulfate and evaporated in vacuum to give 60 mg of the crude aldehyde, which was used in the following steps without purification. LC-MSD, m/z for $C_{10}H_7NO$ [M+H]$^+$: 158.3.

Step 3: (S)-2-{[(Isoquinolin-3-ylmethyl)-amino]-methyl}-pyrrolidine-1-carboxylic acid tert-butyl ester.

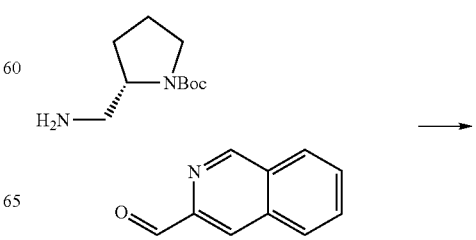

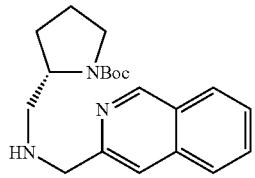

Experimental conditions analogous to Example 1, from 60 mg (0.38 mmol) of isoquinoline-3-carbaldehyde, 0.11 mg (0.57 mmol) of (S)-2-aminomethyl-pyrrolidine-1-carboxylic acid tert-butyl ester, 4 mL dichloromethane, and 0.12 g (0.57 mmol) of sodium triacetoxyborohydride. The residue was purified using reverse phase HPLC, mobile phase with a gradient 10-70% acetonitrile in 40 min, gave 190 mg off-white solid as trifluoroacetate. LC-MSD, m/z for $C_{20}H_{27}N_3O_2$ [M+H]$^+$: 342.5, [M+H-Boc]$^+$: 242.4.

Step 4: 7-Methoxy-2,2-dimethyl-benzo[1,3]dioxole-5-carboxylic acid isoquinolin-3-ylmethyl-(S)-1-pyrrolidin-2-ylmethyl-amide.

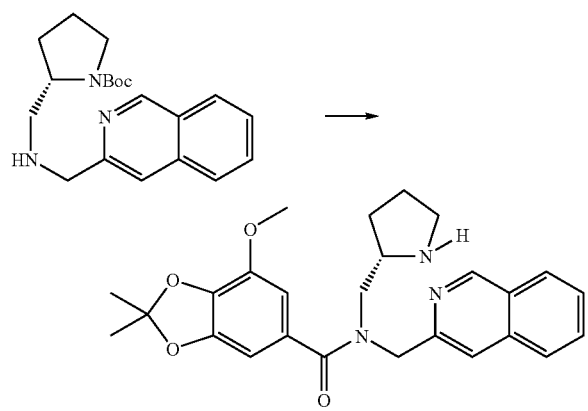

Experimental conditions analogous to Example 60, from 0.17 g (0.38 mmol) of (S)-2-{[(isoquinolin-3-ylmethyl)-amino]-methyl}-pyrrolidine-1-carboxylic acid tert-butyl ester (double trifluoroacetic acid salt), 6 mL dichloromethane, 159 μL (1.14 mmol) of triethylamine, 0.10 g (0.42 mmol) of 7-methoxy-2,2-dimethyl-benzo[1,3]dioxole-5-carbonyl chloride and 0.6 mL trifluoroacetic acid. Purification using reverse phase HPLC, mobile phase with a gradient 10-70% acetonitrile in 40 min, gave 74 mg of the product as the free base as a colorless solid. LC-MSD, m/z for $C_{26}H_{29}N_3O_4$ [M+H]$^+$: 448.6.

Step 5: 7-Methoxy-2,2-dimethyl-benzo[1,3]dioxole-5-carboxylic acid ((S)-1-cyclobutyl-pyrrolidin-2-ylmethyl)-isoquinolin-3-ylmethyl-amide.

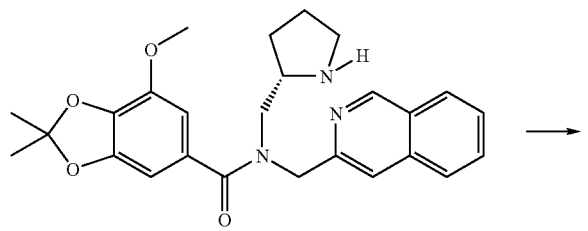

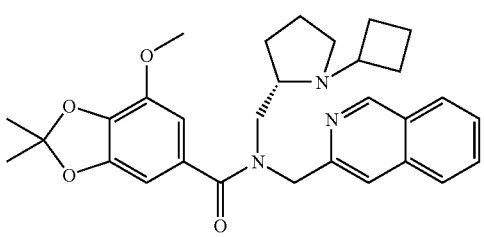

In 1 mL dichloromethane was dissolved 40 mg (0.089 mmol) of 7-methoxy-2,2-dimethyl-benzo[1,3]dioxole-5-carboxylic acid isoquinolin-3-ylmethyl-(S)-1-pyrrolidin-2-ylmethyl-amide, to this solution was added 20 mg (0.25 mmol) of cyclobutanone and 53 mg (0.25 mmol) of sodium triacetoxyborohydride. After overnight the reaction was quenched with aqueous sodium bicarbonate and purified using reverse phase HPLC, mobile phase with a gradient 10-70% acetonitrile in 40 min. Fractions containing pure product were evaporated, the residue was dissolved in dichloromethane, washed with aqueous sodium bicarbonate, dried with anhydrous magnesium sulfate and evaporated in vacuum to yield 27 mg of the product as the free base as a pale yellow solid. LC-MSD, m/z for $C_{30}H_{35}N_3O_4$ [M+H]$^+$: 502.7. $^1$H NMR (400 MHz, CDCl$_3$): δ 1.4-2.0 (m, 9 H), 1.7 (s, 6 H), 2.3-2.4 (m, 1 H), 2.8-3.5 (m, 5 H), 3.7 (bs, 3 H), 3.8-4.0 (m, 1 H), 4.9-5.1 (m, 2 H), 6.6 (s, 1 H), 6.7-6.9 (m, 1 H), 7.5 (bs, 1 H), 7.5-7.6 (m, 1 H), 7.6-7.7 (m, 1 H), 7.8-7.9 (m, 1 H), 7.9-8.0 (m, 1 H), 9.2 (s, 1 H).

Example 63

This example illustrates the preparation of 7-Methoxy-2,2-dimethyl-benzo[1,3]dioxole-5-carboxylic acid {(S)-1-[(1S,3S,5R)-1-(8-aza-bicyclo[3.2.1]oct-3-yl)methyl]-pyrrolidin-2-ylmethyl}-isoquinolin-3-ylmethyl-amide.

Step 1: (±)-(1S,5R)-3-[1-Methoxy-meth-(Z)-ylidene]-8-aza-bicyclo[3.2.1]octane-8-carboxylic acid tert-butyl ester.

To a solution of 3.9 g (11.3 mmol) of methoxymethyl-triphenyl-phosphonium chloride, which was dried on vacuum for 1 h prior to dissolving in 35 mL of dry tetrahydrofuran, 6 mL (12 mmol) of 2M lithium diisopropyl amide solution in heptane/tetrahydrofuran was added dropwise at r.t. and stirred for 30 minutes. To this solution was added a solution of 1.28 g (5.68 mmol) of N-Boc-nortropinone in 10 mL of dry tetrahydrofuran. After the addition was complete, the reaction mixture was stirred at 60° C. for 4 h and then evaporated, redissolved in dichloromethane and purified using flash chromatography using 0-30% ethyl acetate/hexane, yielding 0.97 g of the pure product. LC-MSD, m/z for $C_{14}H_{23}NO_3$ [M+Na]$^+$: 276.5, [M+H-isobutylene]$^+$: 198.4, [M+H-Boc]$^+$: 154.4, [2M+Na]$^+$: 529.7.

Step 2: (1S,3R,5R)-3-Formyl-8-aza-bicyclo[3.2.1]octane-8-carboxylic acid tert-butyl ester

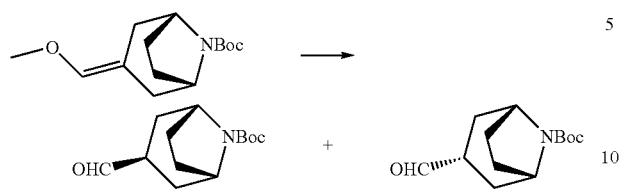

In a mixture of 10 mL dichloromethane and 5 mL water 0.97 g (3.83 mmol) of (±)-(1S,5R)-3-[1-methoxy-meth-(Z)-ylidene]-8-aza-bicyclo[3.2.1]octane-8-carboxylic acid tert-butyl ester was, followed by the addition of 2.5 g (15.3 mmol) of trichloroacetic acid. The mixture was stirred vigorously at r.t. until TLC showed the disappearance of the starting material. The mixture was neutralized by a slow addition of sodium bicarbonate and the organic layer was purified using flash chromatography using 0-30% ethyl acetate/hexane, yield 0.39 g of the first-eluting diastereoisomer and 0.37 g of the other isomer. The compounds are not stable at r.t. and have to be stored in freezer under inert atmosphere. LC-MSD, m/z for $C_{13}H_{22}NO_3$ [M+Na]$^+$: 262.4.

Step 3: 7-Methoxy-2,2-dimethyl-benzo[1,3]dioxole-5-carboxylic acid {(S)-1-[(1S,3S,5R)-1-(8-aza-bicyclo[3.2.1]oct-3-yl)methyl]-pyrrolidin-2-ylmethyl}-isoquinolin-3-ylmethyl-amide.

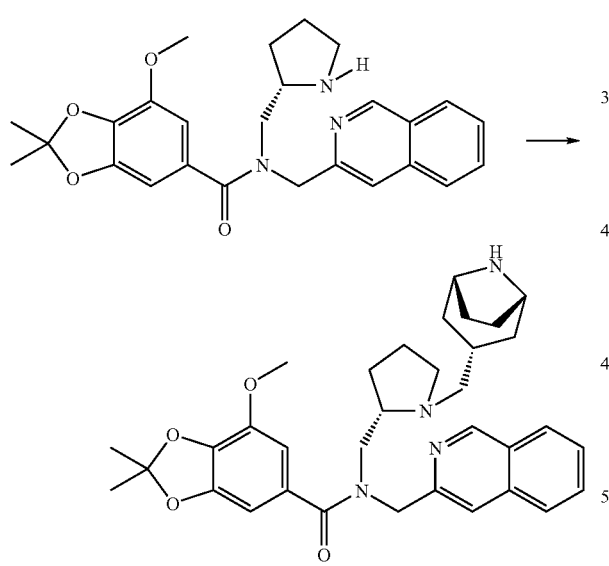

Experimental conditions were analogous to Example 1, from 28 mg (0.063 mmol) of 7-methoxy-2,2-dimethyl-benzo[1,3]dioxole-5-carboxylic acid isoquinolin-3-ylmethyl-(S)-1-pyrrolidin-2-ylmethyl-amide, 2 mL dichloromethane, 16 mg (0.063 mmol) of (1S,3S,5R)-3-formyl-8-aza-bicyclo[3.2.1]octane-8-carboxylic acid tert-butyl ester and 20 mg (0.095 mmol) of sodium triacetoxyborohydride. After overnight the reaction was quenched with aqueous sodium bicarbonate and purified using reverse phase HPLC, mobile phase with a gradient 15-80% acetonitrile in 50 min. The residue was dissolved in 3 mL of 10% trifluoroacetic acid in dichloromethane, and after 2 hours neutralized with aqueous sodium bicarbonate and purified using reverse phase HPLC, mobile phase with a gradient 5-60% acetonitrile in 50 min, gave 20 mg of white solid as the double trifluoroacetic acid salt. LC-MSD, m/z for $C_{34}H_{42}N_4O_4$ [M+H]$^+$: 571.7, [M+2H]$^{2+}$: 286.5. $^1$H NMR (400 MHz, CDCl$_3$): δ 1.7 (s, 6 H), 1.7-2.2 (m, 11 H), 2.4-2.5 (m, 1 H), 2.9-3.1 (m, 2 H), 3.3-3.5 (m, 1 H), 3.8 (s, 3 H), 3.8-4.4 (m, 7 H), 5.0-5.2 (m, 2 H), 6.7 (s, 1 H), 6.9 (bs, 1 H), 7.7-7.8 (m, 1 H), 7.9-8.0 (m, 2 H), 8.1-8.2 (m, 1 H), 9.0 (bs, 1 H), 9.3 (bs, 1 H), 9.4 (bs, 1 H).

Example 64

This example illustrates the preparation of 7-Methoxy-2,2-dimethyl-benzo[1,3]dioxole-5-carboxylic acid isoquinolin-3-ylmethyl-[(2S,3aS,7aS)-1-(octahydro-indol-2-yl)methyl]-amide.

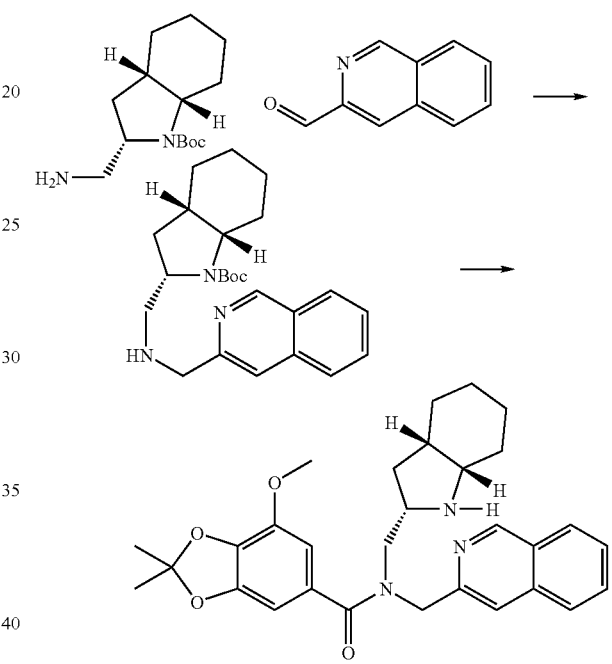

Experimental conditions analogous to Example 1, from 65 mg (0.41 mmol) of isoquinoline-3-carbaldehyde, 126 mg (0.50 mmol) of (2S,3aS,7aS)-2-aminomethyl-octahydro-indole-1-carboxylic acid tert-butyl ester, 3 mL dichloromethane, and 130 mg (0.62 mmol) of sodium triacetoxyborohydride. The reaction was quenched with aqueous sodium bicarbonate. The residue from the organic layer was purified using reverse phase HPLC, mobile phase with a gradient 10-70% acetonitrile in 40 min. Fractions containing pure product were evaporated in vacuum and dissolved in 3 mL dichloromethane followed by 239 μL (1.64 mmol) of triethylamine, 99 mg (0.41 mmol) of 7-methoxy-2,2-dimethyl-benzo[1,3]dioxole-5-carbonyl chloride and 0.3 mL trifluoroacetic acid. The residue from the organic layer was purified using reverse phase HPLC, mobile phase with a gradient 10-70% acetonitrile in 60 min. The residue was dissolved in dichloromethane, washed with aqueous sodium bicarbonate, dried with anhydrous magnesium sulfate and evaporated under vacuum to yield 61 mg pale yellow solid as the free base. LC-MSD, m/z for $C_{30}H_{35}N_3O_4$ [M+H]$^+$: 502.7, [M+2H]$^{2+}$: 251.9, also 207.3, 296.5. $^1$H NMR (400 MHz, CDCl$_3$/HCl): δ 1.3-1.7 (m, 7 H), 1.7 (s, 6 H), 1.8-2.0 (m, 2 H), 2.2-2.4 (m, 2 H), 3.6-3.7 (m, 1 H), 3.8-4.1 (m, 2 H), 3.9 (s, 3 H), 4.4-4.5 (m, 1 H), 5.4-5.6 (m, 2 H), 6.6 (s, 1 H), 7.1 (s, 1 H), 7.9-8.0 (m, 1 H), 8.1-8.2 (m, 1 H), 8.3-8.4 (m, 1 H), 8.4 (bs, 1 H), 8.6 (bs, 1 H), 9.6 (s, 1 H), 11.4-11.6 (bs, 1 H).

Example 65

This example illustrates the preparation of 7-Methoxy-2,2-dimethyl-benzo[1,3]dioxole-5-carboxylic acid [(2S,3aS,7aS)-1-(octahydro-indol-2-yl)methyl]-(2-oxy-isoquinolin-3-ylmethyl)-amide.

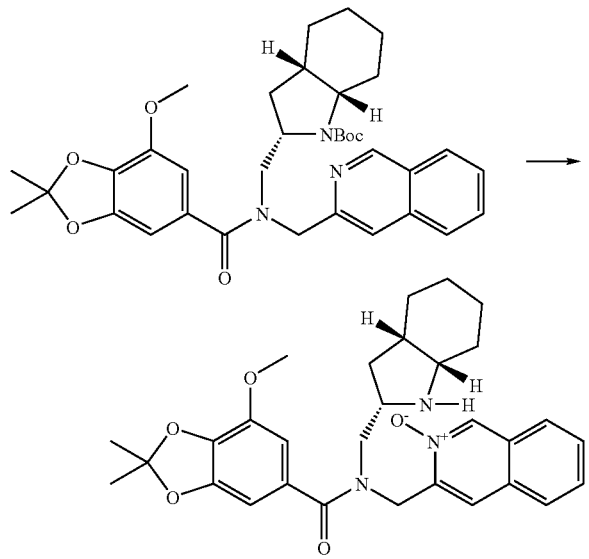

In 5 mL dichloromethane was dissolved 0.34 g (0.57 mmol) of (2S,3aS,7aS)-2-{[isoquinolin-3-ylmethyl-(7-methoxy-2,2-dimethyl-benzo[1,3]dioxole-5-carbonyl)-amino]-methyl}-octahydro-indole-1-carboxylic acid tert-butyl ester and 157 mg of 75% 3-chloroperbenzoic acid (0.68 mmol) were added. The reaction mixture was stirred at r.t. overnight. 0.3 mL of trifluoroacetic acid was subsequently added. The mixture was neutralized with aqueous sodium bicarbonate after 4 hours and purified using reverse phase HPLC, mobile phase with a gradient 10-70% acetonitrile in 50 min. The residue was lyophilized with 0.7 mL of 1 M aqueous acid chlorhydric, gave 115 mg of the pale yellow solid as a hydrochloric salt. LC-MSD, m/z for $C_{30}H_{35}N_3O_5$ [M+H]$^+$: 518.7. $^1$H NMR (400 MHz, CDCl$_3$): δ 1.4-1.7 (m, 5 H), 1.7 (s, 6 H), 1.8-1.9 (m, 1 H), 1.9-2.0 (m, 1 H), 2.0-2.2 (m, 2 H), 2.2-2.4 (m, 2 H), 3.6-3.7 (m, 2 H), 3.9 (s, 3 H), 4.0-4.1 (m, 1 H), 4.3-4.5 (m, 1 H), 5.4-5.5 (m, 2 H), 6.6 (s, 1 H), 7.0 (s, 1 H), 7.9-8.0 (m, 1 H), 8.1-8.2 (m, 1 H), 8.2-8.3 (m, 1 H), 8.3 (bs, 1 H), 8.5 (m, 1 H), 9.1 (bs, 1 H), 9.5 (s, 1 H), 10.4 (bs, 1 H).

Example 66

This example illustrates the preparation of 7-Methoxy-2,2-dimethyl-benzo[1,3]dioxole-5-carboxylic acid (1-isoquinolin-3-yl-ethyl)-[(2S,3aS,7aS)-1-(octahydro-indol-2-yl)methyl]-amide.

Step 1: 1-Isoquinolin-3-yl-ethanone

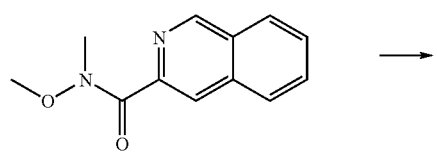

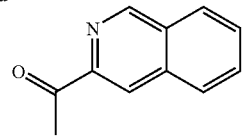

In 10 mL of anhydrous tetrahydrofurane was dissolved 0.28 g (1.32 mmol) of isoquinoline-3-carboxylic acid methoxy-methyl-amide and cooled to –78° C. under the atmosphere of nitrogen. To this mixture was added 0.8 mL of 3.1 M methylmagnesium bromide solution in diethyl ether was added slowly. After the addition was complete, the solution was allowed to warm up to 0° C. over 2 hours and was quenched with aqueous ammonium chloride and extracted with dichloromethane. The organic solution was dried with anhydrous magnesium sulfate and evaporated in vacuum and purified using reverse phase HPLC, mobile phase with a gradient 5-60% acetonitrile in 50 min, gave 201 mg of off white solid as the trifluoroacetate. LC-MSD, m/z for $C_{11}H_9NO$ [M+H]$^+$: 172.4.

Step 2: 7-Methoxy-2,2-dimethyl-benzo[1,3]dioxole-5-carboxylic acid (1-isoquinolin-3-yl-ethyl)-[(2S,3aS,7aS)-1-(octahydro-indol-2-yl)methyl]-amide.

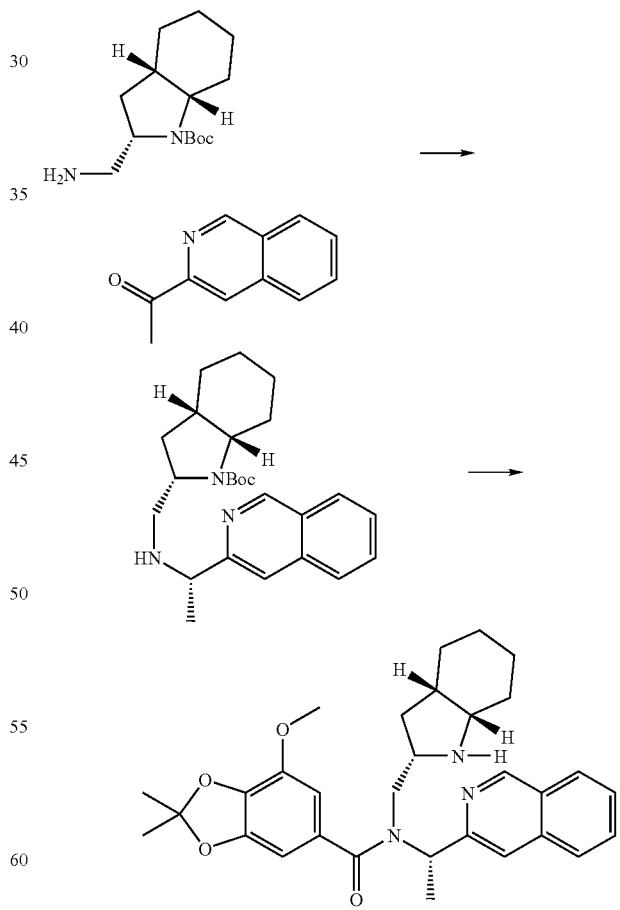

Experimental conditions analogous to Example 1, from 0.19 g (0.68 mmol) of 1-isoquinolin-3-yl-ethanone trifluoroacetic acid salt (neutralized in situ with 95 μL (0.68 mmol) of triethylamine, 0.20 g (0.82 mmol) of (2S,3aS,7aS)-2-aminomethyl-octahydro-indole-1-carboxylic acid tert-butyl ester, 6 mL dichloromethane, and 0.21 g (1.02 mmol) of sodium triacetoxyborohydride. The benzoylation/deprotection steps were done using 284 μL (2.04 mmol) of triethylamine and 0.15 g (0.61 mmol) of 7-methoxy-2,2-dimethyl-benzo[1,3]dioxole-5-carbonyl chloride. The residue from the organic layer was purified using reverse phase HPLC, mobile phase with a gradient 15-80% acetonitrile in 50 min. The residue was dissolved in dichloromethane, washed with aqueous sodium bicarbonate, dried with anhydrous magnesium sulfate and evaporated in vacuum to yield 17 mg of the product as the free base mixture of diastereoisomers. LC-MSD, m/z for $C_{31}H_{37}N_3O_4$ [M+H]$^+$: 516.7, [M+2H]$^{2+}$: 258.9. $^1$H NMR (400 MHz, CDCl$_3$): δ 1.2-2.1 (m, 20 H), 3.0-4.0 (m, 7 H), 5.4-5.5 (m, 1 H), 6.7-6.8 (m, 1 H), 7.0-7.1 (m, 1 H), 7.4-7.9 (m, 4 H), 7.9-8.0 (m, 1 H), 9.2-9.3 (m, 1 H).

Example 67

This example illustrates the preparation of 7-Methoxy-2,2-dimethyl-benzo[1,3]dioxole-5-carboxylic acid ((S)-1-cyclobutyl-pyrrolidin-2-ylmethyl)-quinoxalin-2-ylmethyl-amide.

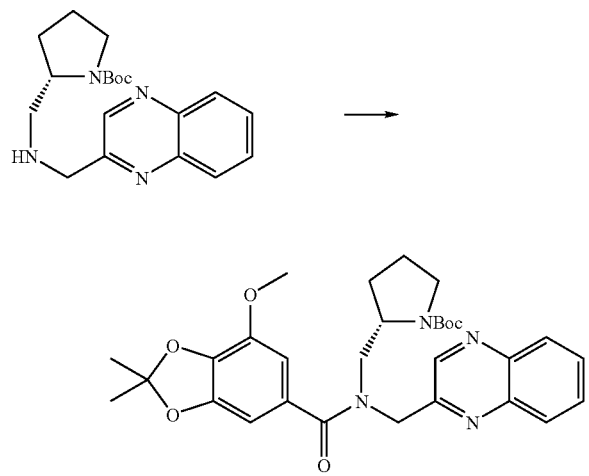

Step 1: (S)-2-{[(7-Methoxy-2,2-dimethyl-benzo[1,3]dioxole-5-carbonyl)-quinoxalin-2-ylmethyl-amino]-methyl}-pyrrolidine-1-carboxylic acid tert-butyl ester.

Experimental conditions analogous Example 1, 0.12 g (0.81 mmol) of quinoxaline-2-carbaldehyde, 0.24 g (1.22 mmol) of (S)-2-aminomethyl-pyrrolidine-1-carboxylic acid tert-butyl ester, 5 mL dichloromethane, and 0.25 g (1.22 mmol) of sodium triacetoxyborohydride. The reaction was quenched with aqueous sodium bicarbonate. The residue from the organic layer was purified using reverse phase HPLC, mobile phase with a gradient 10-70% acetonitrile in 40 min. Fractions containing pure product were evaporated in vacuum and dissolved in 3 mL dichloromethane. To this solution were added 0.34 mL (2.43 mmol) of triethylamine and 196 mg (0.81 mmol) of 7-methoxy-2,2-dimethyl-benzo[1,3]dioxole-5-carbonyl chloride. After 4 hours the reaction mixture was purified using flash chromatography (ethyl acetate in hexane), gave 280 mg as a yellow solid. LC-MSD, m/z for $C_{30}H_{36}N_4O_6$ [M+H]$^+$: 549.7.

Step 2: 7-Methoxy-2,2-dimethyl-benzo[1,3]dioxole-5-carboxylic acid ((S)-1-cyclobutyl-pyrrolidin-2-ylmethyl)-quinoxalin-2-ylmethyl-amide.

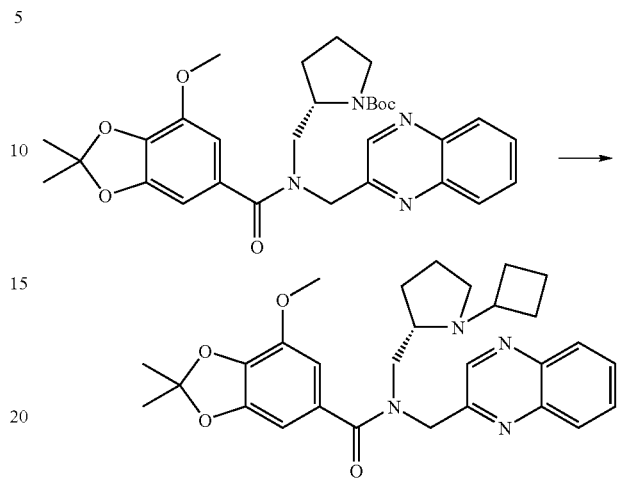

73 mg of (S)-2-{[(7-methoxy-2,2-dimethyl-benzo[1,3]dioxole-5-carbonyl)-quinoxalin-2-ylmethyl-amino]-methyl}-pyrrolidine-1-carboxylic acid tert-butyl ester were dissolved in 3 mL 10% trifluoroacetic acid/dichloromethane and neutralized with aqueous sodium bicarbonate after 2 hours. The crude material was submitted to reductive amination reaction in dichloromethane using 53 mg (0.67 mmol) of cyclobutanone and 0.14 g (0.67 mmol) sodium triacetoxyborohydride. After overnight the reaction was quenched with aqueous sodium bicarbonate and purified using reverse phase HPLC, mobile phase with a gradient 10-70% acetonitrile in 40 min. The residue was dissolved in dichloromethane, washed with aqueous sodium bicarbonate, dried with anhydrous magnesium sulfate and evaporated in vacuum to yield 42 mg pale yellow solid as the free base. LC-MSD, m/z for $C_{29}H_{34}N_4O_4$ [M+H]$^+$: 503.6. $^1$H NMR (400 MHz, CDCl$_3$.HCl): δ 1.7 (s, 6 H), 1.7-3.0 (m, 11 H), 3.6-4.2 (m, 8 H), 5.3-5.4 (m, 1 H), 5.8-5.9 (m, 1 H), 6.6 (s, 1 H), 6.8 (s, 1 H), 8.0 (bs, 2 H), 8.3 (bs, 1 H), 8.5-8.6 (m, 1 H), 9.1 (bs, 1 H), 12.0 (bs, 1 H).

Example 68

This Example illustrates the preparation of 7-Methoxy-2,2-dimethyl-benzo[1,3]dioxole-5-carboxylic acid [(2S,3aS,7aS)-1-(octahydro-indol-2-yl)methyl]-quinoxalin-2-ylmethyl-amide.

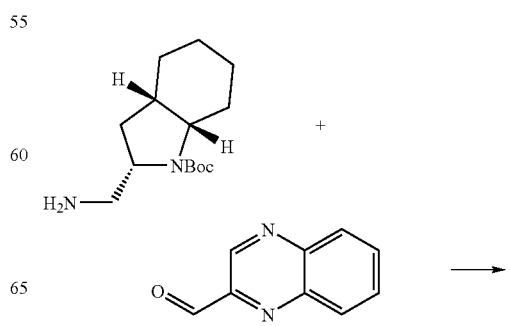

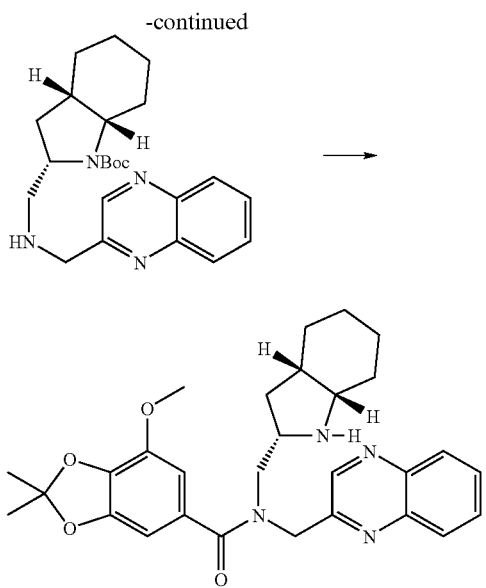

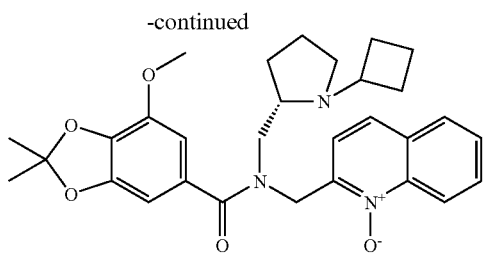

In 3 mL dichloromethane was dissolved 0.15 g (0.28 mmol) of (S)-2-{[(7-methoxy-2,2-dimethyl-benzo[1,3]dioxole-5-carbonyl)-quinolin-2-ylmethyl-amino]-methyl}-pyrrolidine-1-carboxylic acid tert-butyl ester and 77 mg of 75% 3-chloroperbenzoic acid (0.33 mmol) was added. The reaction mixture was stirred at r.t. for 3 hours. The mixture was purified using flash chromatography. The residue was dissolved in 3 mL 10% trifluoroacetic acid/dichloromethane and 0.11 g (1.4 mmol) cyclobutanone and 0.11 g (0.55 mmol) of sodium triacetoxyborohydride. The mixture was purified using reverse phase HPLC, mobile phase with a gradient 15-80% acetonitrile in 50 min, gave 82 mg of a yellow solid as the trifluoroacetate. LC-MSD, m/z for $C_{30}H_{35}N_3O_5$ [M+H]$^+$: 518.7. $^1$H NMR (400 MHz, CDCl$_3$): δ 1.7 (s, 6 H), 1.7-2.4 (m, 10 H), 2.9-3.0 (m, 1 H), 3.6-4.1 (m, 8 H), 5.2-5.4 (m, 2 H), 6.5 (s, 1 H), 6.7 (s, 1 H), 7.7-7.8 (bs, 1 H), 7.8-7.9 (m, 1 H), 7.9-8.0 (m, 1 H), 8.1-8.2 (m, 1 H), 8.6-8.7 (m, 1 H), 11.3 (bs, 1 H).

Experimental conditions analogous to example 1, from with 80 mg (0.51 mmol) of quinoxaline-2-carbaldehyde, 0.15 g (0.61 mmol) of (2S,3aS,7aS)-2-aminomethyl-octahydro-indole-1-carboxylic acid tert-butyl ester, 5 mL dichloromethane, and 0.16 g (0.77 mmol) of sodium triacetoxyborohydride. The benzoylation step was performed using 0.21 mL (1.53 mmol) of triethylamine and 124 mg (0.51 mmol) of 7-methoxy-2,2-dimethyl-benzo[1,3]dioxole-5-carbonyl chloride. After 4 hours the reaction mixture was purified using flash chromatography (ethyl acetate in hexane). The residue was dissolved in 3 mL of 10% trifluoroacetic acid in dichloromethane, and after 4 hours neutralized with aqueous sodium bicarbonate and purified using reverse phase HPLC, mobile phase with a gradient 10-70% acetonitrile in 60 min. The residue was dissolved in dichloromethane, washed with aqueous sodium bicarbonate, dried with anhydrous magnesium sulfate and evaporated under vacuum to yield 60 mg of pale yellow solid as a free base. LC-MSD, m/z for $C_{29}H_{34}N_4O_4$ [M+H]$^+$: 503.6. $^1$H NMR (400 MHz, CDCl$_3$/HCl): δ 1.2-1.9 (m, 15 H), 2.3-2.5 (m, 2 H), 3.6-3.7 (m, 1 H), 3.8 (s, 3 H), 4.0-4.2 (m, 2 H), 4.2-4.4 (m, 1 H), 5.5-5.9 (m, 2 H), 6.7 (s, 1 H), 7.0 (s, 1 H), 8.0-8.1 (m, 2 H), 8.3-8.4 (ms, 1 H), 8.5-8.6 (m, 1 H), 9.0 (bs, 1 H), 10.4 (bs, 1 H), 10.6 (bs, 1 H).

Example 69

This example illustrates the preparation of 7-Methoxy-2,2-dimethyl-benzo[1,3]dioxole-5-carboxylic acid ((S)-1-cyclobutyl-pyrrolidin-2-ylmethyl)-(1-oxy-quinolin-2-ylmethyl)-amide.

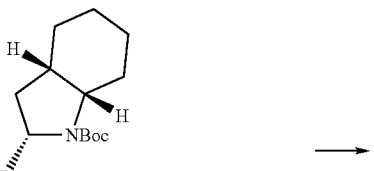

Example 70

This example illustrates the preparation of 7-Methoxy-2,2-dimethyl-benzo[1,3]dioxole-5-carboxylic acid [(2S,3aS,7aS)-1-(octahydro-indol-2-yl)methyl]-quinolin-2-ylmethyl-amide.

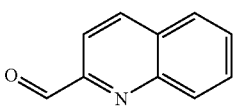

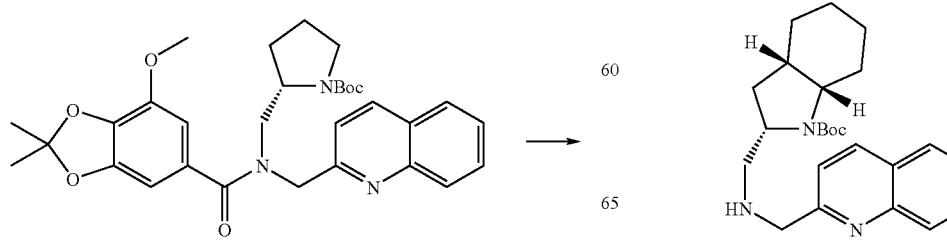

-continued

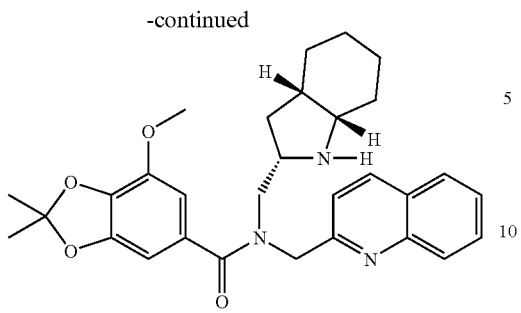

Experimental conditions analogous to Example 1, from 0.119 g (0.76 mmol) of quinoline-2-carbaldehyde, 0.23 g (0.91 mmol) of (2S,3aS,7aS)-2-aminomethyl-octahydro-indole-1-carboxylic acid tert-butyl ester, 5 mL dichloromethane, and 0.24 g (1.14 mmol) of sodium triacetoxyborohydride. The reaction was quenched with aqueous sodium bicarbonate. The residue from the organic layer was purified using flash chromatography (0-20% methanol in dichloromethane). The benzoylation step was performed using 0.13 mL (0.91 mmol) of triethylamine and 0.17 g (0.72 mmol) of 7-methoxy-2,2-dimethyl-benzo[1,3]dioxole-5-carbonyl chloride. After 4 hours the reaction mixture was purified using flash chromatography (ethyl acetate in hexane). The residue was dissolved in 8 mL of 10% trifluoroacetic acid in dichloromethane, and after 4 hours neutralized with aqueous sodium bicarbonate and purified using reverse phase HPLC, mobile phase with a gradient 10-70% acetonitrile in 50 min. The residue was dissolved in dichloromethane, washed with aqueous sodium bicarbonate, dried with anhydrous magnesium sulfate and evaporated under vacuum to yield 135 mg of off white solid as a free base. LC-MSD, m/z for $C_{30}H_{35}N_3O_4$ [M+H]$^+$: 502.7, [M+2H]$^{2+}$: 251.9. $^1$H NMR (400 MHz, CDCl$_3$/HCl): δ 1.4-2.4 (m, 15 H), 2.6-3.2 (m, 2 H), 3.6-3.8 (m, 2 H), 3.9-4.0 (m, 4H), 4.3-4.4 (m, 1 H), 5.6-5.8 (m, 2 H), 6.7 (s, 1 H), 7.1 (bs, 1 H), 7.8-7.9 (m, 1 H), 8.0-8.1 (m, 2 H), 8.2 (bs, 1 H), 8.8 (bs, 1 H), 8.9 (bs, 1 H), 11.8 (bs, 1 H).

Example 71

This example illustrates the preparation of 7-Methoxy-2,2-dimethyl-benzo[1,3]dioxole-5-carboxylic acid [(2S,3aS,7aS)-1-(octahydro-indol-2-yl)methyl]-(1-quinolin-2-yl-ethyl)-amide.

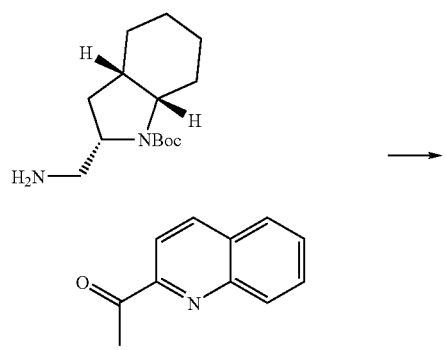

-continued

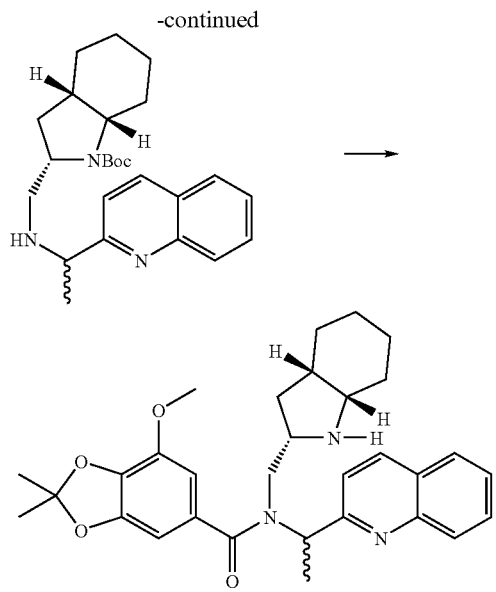

Experimental conditions analogous to Example 1, from 72 mg (0.41 mmol) of 1-quinolin-2-yl-ethanone, 0.1 g (0.41 mmol) of (2S,3aS,7aS)-2-aminomethyl-octahydro-indole-1-carboxylic acid tert-butyl ester, 4 mL dichloromethane, and 0.13 g (0.62 mmol) of sodium triacetoxyborohydride. The acylation was made using 207 μL (1.49 mmol) of triethylamine and 95 mg (0.39 mmol) of 7-methoxy-2,2-dimethyl-benzo[1,3]dioxole-5-carbonyl chloride. The mixture was purified using reverse phase HPLC, mobile phase with a gradient 35-95% acetonitrile in 50 min. The residue was submitted to deprotection analogous to Example 70. The mixture was purified using reverse phase HPLC, mobile phase with a gradient 15-80% acetonitrile in 50 min, gave 30 mg of off white solid as the trifluoroacetate. LC-MSD, m/z for $C_{31}H_{37}N_3O_4$ [M+H]$^+$: 516.7, [M+2H]$^{2+}$: 258.9. $^1$H NMR (400 MHz, CDCl$_3$): δ 1.4-1.8 (m, 14 H), 1.8-1.9 (m, 3 H), 1.9-2.0 (m, 1 H), 2.2-2.3 (m, 1 H), 2.4-2.5 (m, 1 H), 3.6-3.7 (m, 1 H), 3.7 (s, 3 H), 3.8-3.9 (m, 1 H), 4.2-4.4 (m, 2 H), 5.4-5.6 (m, 1 H), 6.5 (s, 1 H), 6.7 (s, 1 H), 7.2-7.3 (m, 1 H), 7.6-7.7 (m, 1 H), 7.8-7.9 (m, 2 H), 8.1-8.2 (m, 1 H), 8.2-8.3 (m, 1 H), 8.5 (bs, 1 H), 10.5 (bs, 1 H).

Example 72

This example illustrates the preparation of 7-Methoxy-2,2-dimethyl-benzo[1,3]dioxole-5-carboxylic acid (6-fluoro-quinolin-2-ylmethyl)-[(2S,3aS,7aS)-1-(octahydro-indol-2-yl)methyl]-amide.

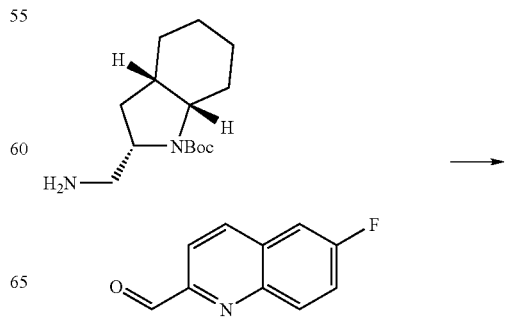

-continued

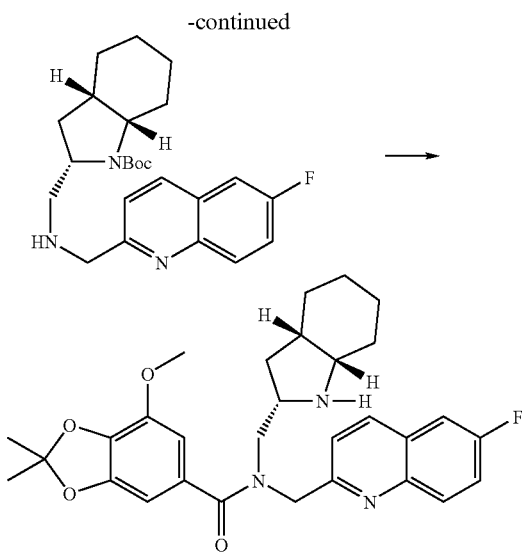

Experimental conditions analogous Example 1, from 76 mg (0.43 mmol) of 6-fluoro-quinoline-2-carbaldehyde, 0.132 g (0.52 mmol) of (2S,3aS,7aS)-2-aminomethyl-octahydro-indole-1-carboxylic acid tert-butyl ester, 3 mL dichloromethane, and 0.13 g (0.65 mmol) of sodium triacetoxyborohydride. The benzoylation step was made using 217 µL (1.56 mmol) of triethylamine and 0.1 g (0.41 mmol) of 7-methoxy-2,2-dimethyl-benzo[1,3]dioxole-5-carbonyl chloride. The mixture was purified using flash chromatography (5-65% ethyl acetate in hexane). The residue was deprotected analogous to Example 70. The mixture was purified using reverse phase HPLC, mobile phase with a gradient 15-80% acetonitrile in 50 min, gave 71 mg of pale yellow solid as trifluoroacetate. LC-MSD, m/z for $C_{30}H_{34}FN_3O_4$ [M+H]$^+$: 520.7, [M+2H]$^{2+}$: 260.9. $^1$H NMR (400 MHz, CDCl$_3$): δ 1.4-1.8 (m, 14 H), 1.9-2.2 (m, 2 H), 2.4-2.5 (m, 1 H), 3.5-3.6 (m, 1 H), 3.7 (s, 3 H), 3.7-3.8 (m, 1 H), 4.0-4.2 (m, 1 H), 4.3-4.4 (m, 1 H), 5.1 (s, 2 H), 6.6 (s, 1 H), 6.9 (s, 1 H), 7.5-7.7 (m, 3 H), 8.2-8.3 (m, 1 H), 8.3-8.4 (m, 2 H), 10.5 (bs, 1 H).

Example 73

This example illustrates the preparation of 7-Methoxy-2,2-dimethyl-benzo[1,3]dioxole-5-carboxylic acid (6-chloro-quinolin-2-ylmethyl)-[(2S,3aS,7aS)-1-(octahydro-indol-2-yl)methyl]-amide.

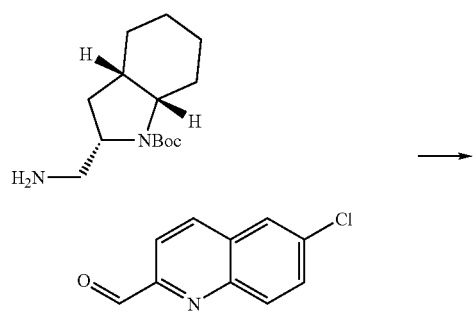

-continued

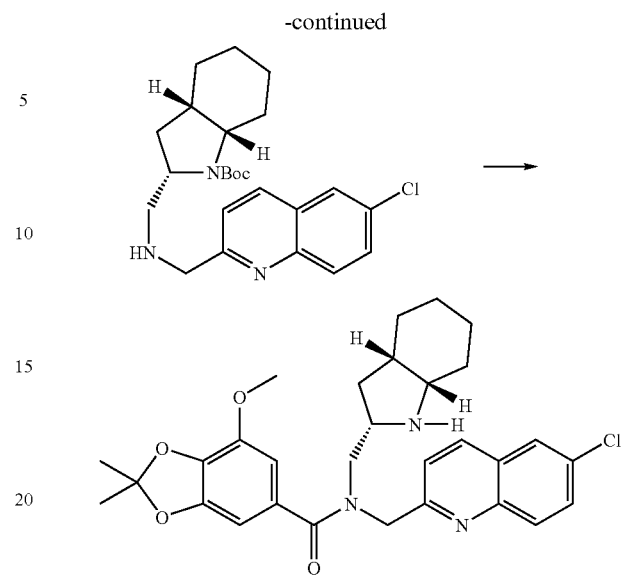

Experimental conditions analogous to Example 1, from 79 mg (0.41 mmol) of 6-chloro-quinoline-2-carbaldehyde, 0.12 g (0.50 mmol) of (2S,3aS,7aS)-2-aminomethyl-octahydro-indole-1-carboxylic acid tert-butyl ester, 3 mL dichloromethane, and 0.13 g (0.62 mmol) of sodium triacetoxyborohydride. The benzoylation step was performed using 207 µL (1.49 mmol) of triethylamine and 95 mg (0.39 mmol) of 7-methoxy-2,2-dimethyl-benzo[1,3]dioxole-5-carbonyl chloride. The mixture was purified using flash chromatography (5-70% ethyl acetate in hexane). The residue was deprotected analogous Example 70. The mixture was purified using reverse phase HPLC, mobile phase with a gradient 15-80% acetonitrile in 50 min, gave 58 mg of a pale yellow solid as trifluoroacetate. LC-MSD, m/z for $C_{30}H_{34}ClN_3O_4$ [M+H]$^+$: 536.6, 538.6 [M+2H]$^{2+}$: 268.9.

$^1$H NMR (400 MHz, CDCl$_3$): δ 1.4-1.8 (m, 14 H), 1.9-2.2 (m, 2 H), 2.4-2.5 (m, 1 H), 3.4-3.5 (m, 1 H), 3.6 (s, 3 H), 3.7-3.8 (m, 1 H), 4.2-4.4 (m, 2 H), 4.9-5.1 (m, 2 H), 6.6 (s, 1 H), 6.9 (s, 1 H), 7.3-0.74 (m, 1 H), 7.7-7.8 (m, 1 H), 7.8-7.9 (m, 1 H), 8.0-8.1 (m, 1 H), 8.1-8.2 (m, 1 H), 8.4 (bs, 1 H), 10.8 (bs, 1 H).

Example 74

This example illustrates the preparation of 7-Methoxy-2,2-dimethyl-benzo[1,3]dioxole-5-carboxylic acid cinnolin-3-ylmethyl-((S)-1-cyclobutyl-pyrrolidin-2-ylmethyl)-amide.

Step 1: (S)-2-{[Cinnolin-3-ylmethyl-(7-methoxy-2,2-dimethyl-benzo[1,3]dioxole-5-carbonyl)-amino]-methyl}-pyrrolidine-1-carboxylic acid tert-butyl ester.

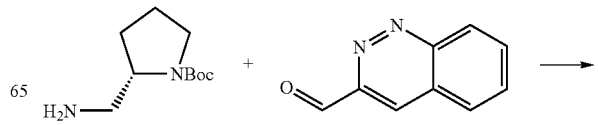

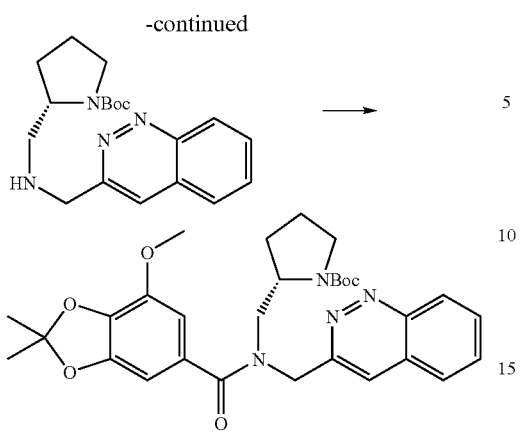

Experimental conditions analogous to Example 1, from 0.26 g (1.65 mmol) of cinnoline-3-carbaldehyde, 0.49 g (2.47 mmol) of (S)-2-aminomethyl-pyrrolidine-1-carboxylic acid tert-butyl ester, 10 mL dichloromethane, and 0.52 mg (2.47 mmol) of sodium triacetoxyborohydride. The reaction was quenched with aqueous sodium bicarbonate. The residue from the organic layer was purified using flash chromatography (0-20% methanol in dichloromethane). The organic layer was concentrated under vacuum and dissolved in 5 mL dichloromethane. To this solution were added 0.34 mL (2.47 mmol) of triethylamine and 0.4 g (1.65 mmol) of 7-methoxy-2,2-dimethyl-benzo[1,3]dioxole-5-carbonyl chloride. After 1 hour the reaction mixture was purified using flash chromatography (10-100% ethyl acetate in hexane), gave 182 mg as a yellow solid. LC-MSD, m/z for $C_{30}H_{36}N_4O_6$ [M+H]$^+$: 549.7

Step 2: 7-Methoxy-2,2-dimethyl-benzo[1,3]dioxole-5-carboxylic acid cinnolin-3-ylmethyl-((S)-1-cyclobutyl-pyrrolidin-2-ylmethyl)-amide.

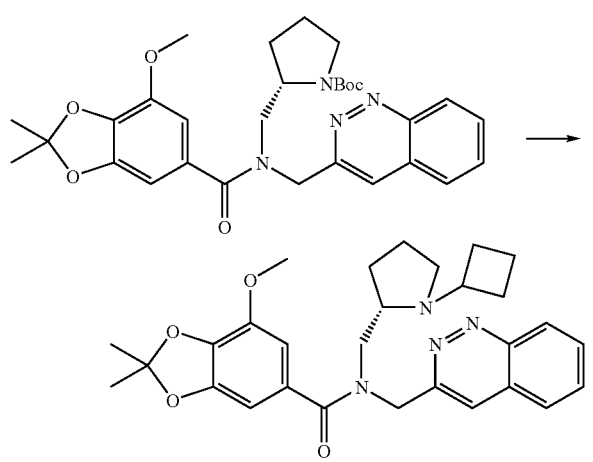

Experimental conditions analogous to Example 1, from 172 mg (0.31 mmol) of (S)-2-{[cinnolin-3-ylmethyl-(7-methoxy-2,2-dimethyl-benzo[1,3]dioxole-5-carbonyl)-amino]-methyl}-pyrrolidine-1-carboxylic acid tert-butyl ester and 3 mL 10% trifluoroacetic acid/dichloromethane. The crude deprotected material was submitted to reductive amination reaction in 5 mL dichloromethane using 108 mg (1.55 mmol) of cyclobutanone and 329 mg (1.55 mmol) sodium triacetoxyborohydride. The reaction mixture was purified using flash chromatography elution with 0-10% methanol in dichloromethane, gave 47 mg of pale yellow solid as the free base. LC-MSD, m/z for $C_{29}H_{34}N_4O_4$ [M+H]$^+$: 503.7. $^1$H NMR (400 MHz, CDCl$_3$): δ 1.6-2.5 (m, 16 H), 2.8-2.9 (m, 1 H), 3.5-3.8 (m, 3 H), 3.8 (s, 3 H), 3.9-4.0 (m, 2 H), 5.1-5.3 (m, 2 H), 6.8 (bs, 1 H), 7.2 (bs, 1 H), 7.7-7.9 (m, 4 H), 8.4-8.5 (m, 1 H).

Example 75

This example illustrates the preparation of N-((S)-1-Cyclohexylmethyl-pyrrolidin-2-ylmethyl)-3,4-dimethoxy-N-(3-pyrazol-1-yl-phenyl)-benzamide.

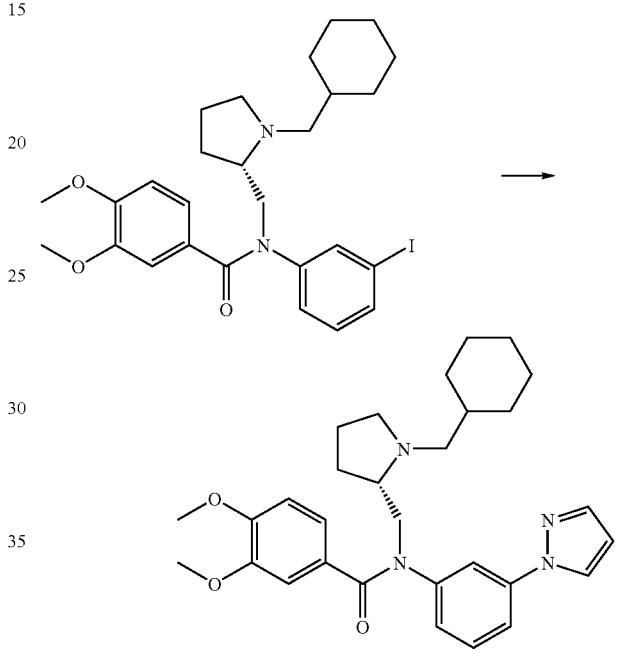

In 1 mL dimethyl sulfoxide were dissolved and suspended, 118 mg (0.21 mmol) of N-((S)-1-cyclohexylmethyl-pyrrolidin-2-ylmethyl)-N-(3-iodo-phenyl)-3,4-dimethoxy-benzamide, 43 mg (0.63 mmol) of 1H-pyrazole, 44 mg (0.32 mmol) of potassium carbonate, 8 mg (0.042 mmol) of copper(I) iodide and 6.1 mg (0.042 mmol) of 8-hydroxyquinoline. The reaction was stirred 1 hour at 110° C. under nitrogen atmosphere overnight. The mixture was cooled down and diluted with 15 mL with ethyl acetate, filtered through a celite and concentrated under vacuum. The compound was purified using reverse phase HPLC, mobile phase with a gradient 20-80% acetonitrile in 50 min. The fractions were lyophilized with 1 mL 1M hydrochloric acid, to yield 72 mg of pale yellow solid as hydrochloric salt. LC-MSD, m/z for $C_{30}H_{38}N_4O_3$ [M+H]$^+$: 503.4. $^1$H NMR (400 MHz, CD$_3$OD): δ 1.1-1.4 (m, 5H), 1.7-1.9 (m, 5H), 1.9-2.1 (m, 2 H), 2.1-2.2 (m, 2 H), 2.2-2.3 (m, 1 H), 3.0-3.1 (m, 1 H), 3.2-3.4 (m, 2 H), 3.6 (s, 3 H), 3.8 (s, 3 H), 3.8-3.9 (m, 2 H), 4.3-4.6 (m, 2 H), 6.5-6.6 (m, 1H), 6.8-6.9 (m, 1H), 6.9-7.0 (m, 1H), 7.0-7.1 (m, 1H), 7.1-7.2 (m, 1H), 7.4-7.5 (m, 1H), 7.6-7.7 (m, 1 H), 7.7-7.8 (m, 2 H), 8.2-8.3 (m, 1H).

Example 76

This example illustrates the preparation of N-((S)-1-Cyclohexylmethyl-pyrrolidin-2-ylmethyl)-3,4-dimethoxy-N-(3-[1,2,3]triazol-1-yl-phenyl)-benzamide

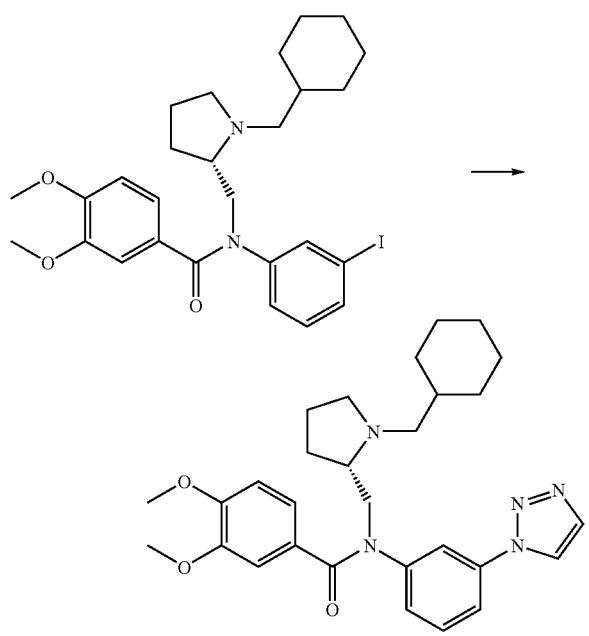

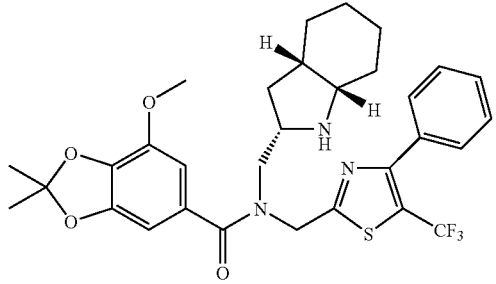

Experimental conditions analogous Example 75, from 95 mg (0.17 mmol) of N-((S)-1-cyclohexylmethyl-pyrrolidin-2-ylmethyl)-N-(3-iodo-phenyl)-3,4-dimethoxy-benzamide, 35 mg (0.51 mmol) of 1H-[1,2,3]triazole, 35 mg (0.25 mmol) of potassium carbonate, 6.4 mg (0.034 mmol) of copper(I) iodide, 4.9 mg (0.034 mmol) of 8-hydroxyquinoline and 0.7 mL dimethyl sulfoxide. Purification was achieved using reverse phase HPLC, mobile phase with a gradient 10-70% acetonitrile in 50 min, and the pure fractions were lyophilized with 1 mL 1M HCl, gave 13 mg of yellow solid as the hydrochloric salt. LC-MSD, m/z for $C_{29}H_{37}N_5O_3$ [M+H]+: 504.4. $^1$H NMR (400 MHz, CD$_3$OD): δ 1.1-1.4 (m, 5H), 1.7-1.9 (m, 5H), 1.9-2.1 (m, 2 H), 2.1-2.2 (m, 2 H), 2.2-2.3 (m, 1 H), 3.0-3.1 (m, 1 H), 3.2-3.4 (m, 2 H), 3.6 (s, 3 H), 3.8 (s, 3 H), 3.8-3.9 (m, 2 H), 4.3-4.6 (m, 2 H), 6.7-6.8 (m, 1H), 6.9-7.0 (m, 1H), 7.0-7.1 (m, 1H), 7.2-7.3 (m, 1H), 7.4-7.5 (m, 1H), 7.8-7.9 (s, 2 H), 7.9-8.0 (s, 2 H).

Example 77

This example illustrates the preparation of 7-Methoxy-2,2-dimethyl-benzo[1,3]dioxole-5-carboxylic acid [(2S,3aS,7aS)-1-(octahydro-indol-2-yl)methyl]-(4-phenyl-5-trifluoromethyl-thiazol-2-ylmethyl)-amide.

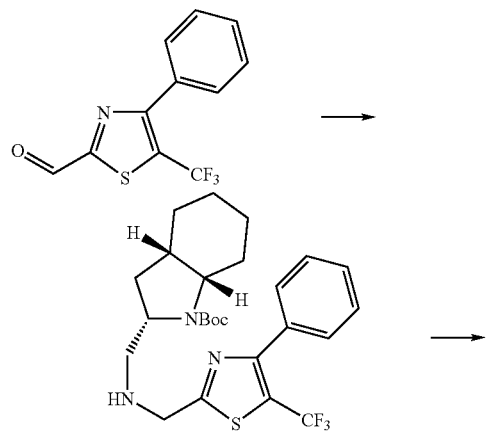

-continued

Experimental conditions analogous to Example 1, were used with 94 mg (0.60 mmol) 4-phenyl-5-trifluoromethyl-thiazole-2-carbaldehyde, 152 mg (0.60 mmol) of (2S,3aS,7aS)-2-aminomethyl-octahydro-indole-1-carboxylic acid tert-butyl ester, 3 mL dichloromethane, and 191 mg (0.90 mmol) of sodium triacetoxyborohydride. The crude (3-methyl-4-phenyl-5-trifluoromethyl-2,3-dihydro-thiazol-2-ylmethyl)-(octahydro-indol-2-ylmethyl)-amine was treated with 0.3 g (3 mmol) of triethylamine and 0.24 g (1 mmol) of 7-methoxy-2,2-dimethyl-benzo[1,3]dioxole-5-carbonyl chloride. The mixture was purified using flash chromatography (ethyl acetate in hexane), gave a yellow semi-solid residue. The residue was deprotected using 3 mL 10% trifluoroacetic acid/dichloromethane. The mixture was purified using reverse phase HPLC, mobile phase with a gradient 15-80% acetonitrile in 50 min, gave 14 mg of white solid as the trifluoroacetate. LC-MSD, m/z for $C_{31}H_{34}F_3N_3O_4S$ [M+H]+: 602.7. $^1$H NMR (400 MHz, CDCl$_3$): δ 1.4-1.8 (m, 15 H), 1.9-2.0 (m, 1 H), 2.2-2.3 (m, 1 H), 2.4-2.6 (m, 1 H), 3.4-3.5 (m, 1 H), 3.8 (s, 3 H), 4.3-4.5 (m, 2 H), 4.8-5.2 (m, 2 H), 6.6 (s, 1 H), 6.9 (s, 1 H), 7.4-7.5 (m, 3 H), 7.6-7.7 (m, 2 H), 8.0 (bs, 1 H), 11.4 (bs, 1 H).

Example 78

This example illustrates the preparation of 7-Methoxy-2,2-dimethyl-benzo[1,3]dioxole-5-carboxylic acid ((S)-1-cyclobutyl-pyrrolidin-2-ylmethyl)-(1-phenyl-1H-pyrazol-3-ylmethyl)-amide.

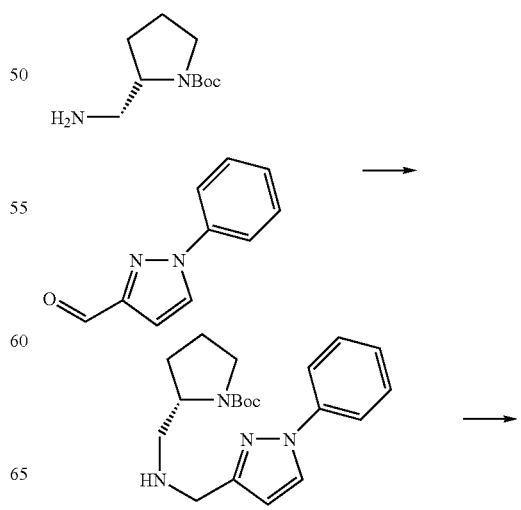

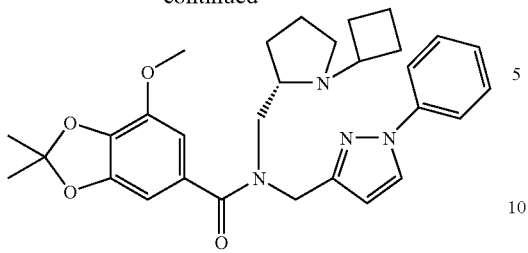

Experimental conditions analogous to Example 1, from 0.16 g (0.81 mmol) of (S)-2-aminomethyl-pyrrolidine-1-carboxylic acid tert-butyl ester, 70 mg (0.41 mmol) of 1-phenyl-1H-pyrazole-4-carbaldehyde, 4 mL dichloromethane, and 0.17 g (0.81 mmol) of sodium triacetoxyborohydride. (1-Phenyl-1H-pyrazol-3-ylmethyl)-pyrrolidin-2-ylmethyl-amine was treated with 566 µL (4.06 mmol) of triethylamine and 0.43 g (1.79 mmol) of 7-methoxy-2,2-dimethyl-benzo[1,3]dioxole-5-carbonyl chloride. The compound was deprotected using 3 mL of 10% TFA in dichloromethane. 7-Methoxy-2,2-dimethyl-benzo[1,3]-dioxolo-5-carboxylic acid (1-cyclobutyl-pyrrolidin-2-ylmethyl)-[1-(1-ethylidene-penta-2,4-dienyl)-1H-pyrazol-3-ylmethyl]-amide was alkylated using 98 mg (1.22 mmol) cyclobutanone and 0.25 g (1.22 mmol) of sodium triacetoxyborohydride. The compound was purified using reverse phase HPLC, mobile phase with a gradient 20-80% acetonitrile in 50 min, gave 50 mg of white solid as the trifluoroacetate. LC-MSD, m/z for $C_{30}H_{36}N_4O_4$ $[M+H]^+$: 517.7. $^1H$ NMR (400 MHz, CDCl$_3$): δ 1.7-2.4 (m, 17 H), 2.9-3.1 (m, 1 H), 3.6-3.8 (m, 2 H), 3.9 (s, 3 H), 3.9-4.0 (m, 2 H), 4.6-4.8 (m, 2 H), 6.6 (s, 1 H), 6.7 (s, 1 H), 7.3-7.4 (m, 1 H), 7.4-7.5 (m, 2 H), 7.5 (bs, 1 H), 7.6-7.8 (m, 4 H), 8.0 (s, 1 H), 11.1 (bs, 1 H).

Example 79

This example illustrates the preparation of 7-Methoxy-2,2-dimethyl-benzo[1,3]dioxole-5-carboxylic acid (5-chloro-2-phenyl-thiazol-4-ylmethyl)-[(2S,3aS,7 aS)-1-(octahydro-indol-2-yl)methyl]-amide.

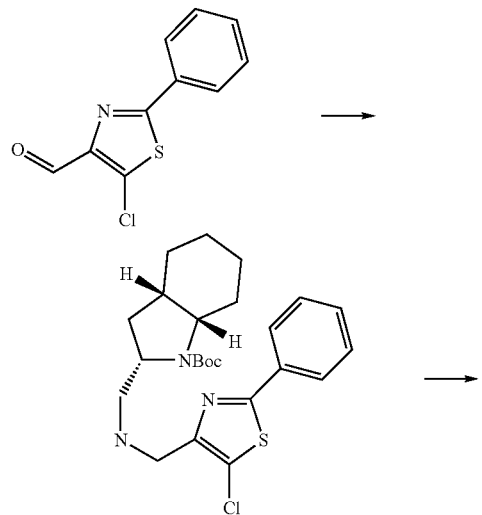

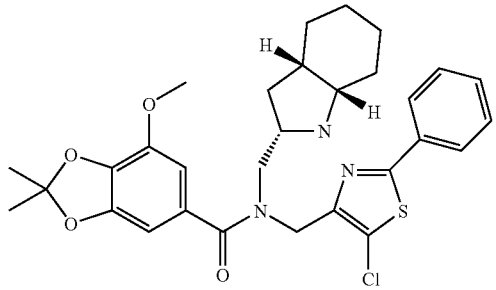

Experimental condition analogous to Example 1, from 70 mg (0.31 mmol) of 5-chloro-2-phenyl-thiazole-4-carbaldehyde, 80 mg (0.31 mmol) of (2S,3aS,7aS)-2-aminomethyl-octahydro-indole-1-carboxylic acid tert-butyl ester, 4 mL dichloromethane, and 110 mg (0.52 mmol) of sodium triacetoxyborohydride. The (5-chloro-2-phenyl-thiazole-4-ylmethyl)-(octahydro-indol-2-ylmethyl)-amine was acylated using 200 µL (1.43 mmol) of triethylamine and 100 mg (0.41 mmol) of 7-methoxy-2,2-dimethyl-benzo[1,3]dioxole-5-carbonyl chloride. The crude compound was deprotected in 5 mL 10% trifluoroacetic acid in dichloromethane. The compound was purified using reverse phase HPLC, mobile phase with a gradient 15-80% acetonitrile in 50 min gave 12 mg of white solid as the trifluoroacetate. LC-MSD, m/z for $C_{30}H_{34}ClN_3O_4S$ $[M+H]^+$: 568.6. $^1H$ NMR (400 MHz, CDCl$_3$): δ 1.4-1.8 (m, 15 H), 1.9-2.1 (m, 1 H), 2.1-2.2 (m, 1 H), 2.4-2.6 (m, 1 H), 3.4-3.5 (m, 1 H), 3.7-3.8 (m, 1 H), 3.8 (s, 3 H), 4.2-4.3 (m, 1 H), 4.4 (bs, 1 H), 4.5-4.9 (m, 2 H), 6.8 (s, 1 H), 7.0 (s, 1 H), 7.4-7.5 (m, 3 H), 7.8-7.9 (m, 2 H), 8.2 (bs, 1 H), 11.4 (bs, 1 H).

Example 80

To demonstrate that the compounds described above are useful modulators for chemokine binding to CCXCKR2, the compounds were screened in vitro to determine their ability to displace SDF-1 from the CCXCKR2 receptor at multiple concentrations. The compounds were combined with mammary gland cells expressing the CCXCKR2 receptor in the presence of the $^{125}I$-labeled chemokine as detailed in *Determination of IC$_{50}$ values, Reagents and Cells* (see below). The ability of the compounds to displace the labeled chemokine from the CCXCKR2 receptor sites at multiple concentrations was then determined with the screening process.

Compounds that were deemed effective modulators were able to displace at least 50% of the SDF-1 from the CCX-CKR2 receptor at concentrations at or below 10 micromolar (µM) and more preferably at concentrations at or below 2 micromolar. At present, especially preferred compounds can displace at least 50% of the SDF-1 from the CCXCKR2 receptor at concentrations at or below 500 nM. Exemplary compounds that met these criteria are reproduced in Table B below. All compounds were prepared as described in the Examples above, or by related methods substituting readily available starting materials.

TABLE B

| No. | Compound | Activity | No. | Compound | Activity |
|---|---|---|---|---|---|
| 17 | | +++ | 18 | | +++ |
| 5 | | +++ | 6 | | ++ |
| 19 | | ++ | 20 | | ++ |

TABLE B-continued

| No. | Compound | Activity | No. | Compound | Activity |
|---|---|---|---|---|---|
| 10 | (structure) | + | 11 | (structure) | +++ |
| 7 | (structure) | +++ | 9 | (structure) | +++ |
| 8 | (structure) | +++ | | (structure) | +++ |

TABLE B-continued

| No. | Compound | Activity | No. | Compound | Activity |
|---|---|---|---|---|---|
| 12 | | ++ | 13 | | +++ |
| | | | 14 | | + |
| | | | 15 | | ++ |
| 4 | | +++ | | | |

TABLE B-continued

| No. | Compound | Activity | No. | Compound | Activity |
|---|---|---|---|---|---|
| 1 | | +++ | 2 | | ++ |
| 1a | | +++ | 21 | | ++ |
| 22 | | +++ | 23 | | +++ |

TABLE B-continued

| No. | Compound | Activity | No. | Compound | Activity |
|---|---|---|---|---|---|
| 24 | | +++ | 28 | | +++ |
| 26 | | +++ | 25 | | ++ |
| 27 | | +++ | 30 | | +++ |

TABLE B-continued

| No. | Compound | Activity | No. | Compound | Activity |
|---|---|---|---|---|---|
| 31 | | +++ | 33 | | +++ |
| 32 | | +++ | 75 | | + |
|  |  |  | 29 | | ++ |

TABLE B-continued

| No. | Compound | Activity | No. | Compound | Activity |
|---|---|---|---|---|---|
| 76 | | + | 34 | | + |
| 35 | | ++ | 36 | | + |
| 38 | | + | 37 | | + |
| 39 | | ++ | | | +++ |

TABLE B-continued

| No. | Compound | Activity | No. | Compound | Activity |
|---|---|---|---|---|---|
| 57 | | +++ | 58 | | +++ |
| 59 | | +++ | 60 | | +++ |
| 61 | | +++ | 62 | | +++ |

TABLE B-continued

| No. | Compound | Activity | No. | Compound | Activity |
|---|---|---|---|---|---|
| | | + | 50 | | +++ |
| | | ++ | 67 | | ++ |
| 51 | | +++ | 63 | | +++ |

TABLE B-continued

| No. | Compound | Activity | No. | Compound | Activity |
|---|---|---|---|---|---|
| 68 | | +++ | 64 | | +++ |
| 39 | | ++ | 40 | | +++ |
| 70 | | +++ | 52 | | +++ |

TABLE B-continued
| No. | Compound | Activity | No. | Compound | Activity |
|---|---|---|---|---|---|
| 44 | 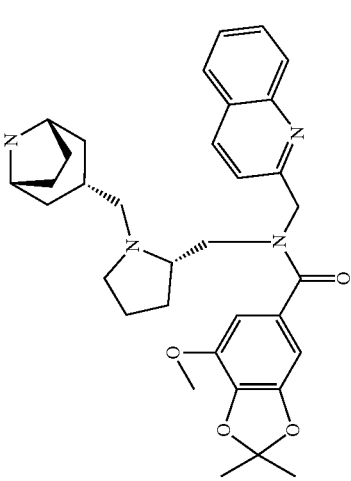 | +++ | 45 | 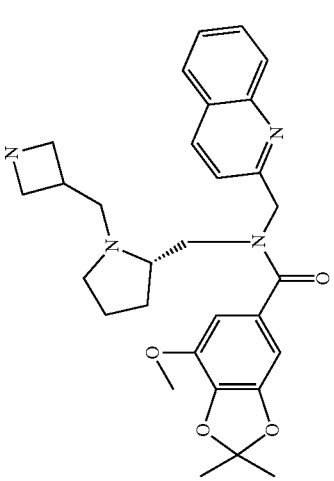 | +++ |
| 46 | 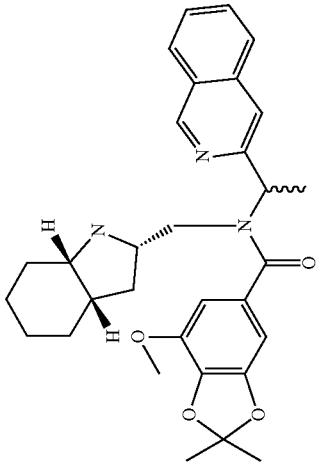 | +++ | 99 | 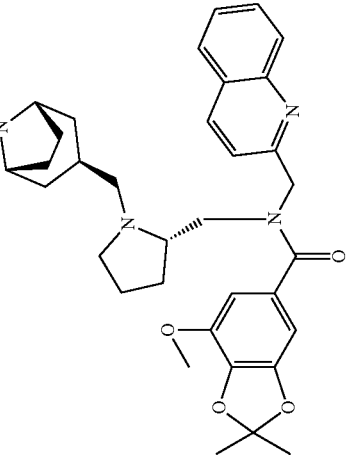 | ++ |

TABLE B-continued

| No. | Compound | Activity | No. | Compound | Activity |
|---|---|---|---|---|---|
| 53 | | +++ | 54 | | +++ |
| 42 | | +++ | 41 | | +++ |
| 65 | | ++ | 74 | | ++ |

TABLE B-continued

| No. | Compound | Activity | No. | Compound | Activity |
|---|---|---|---|---|---|
| 43 | | +++ | 69 | | + |
| 48 | | +++ | 49 | | +++ |
| 47 | | +++ | 72 | | +++ |

TABLE B-continued
| No. | Compound | Activity | No. | Compound | Activity |
|---|---|---|---|---|---|
| 71 | 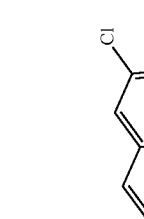 | +++ | 73 | 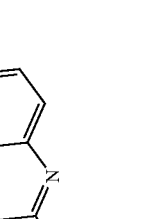 | +++ |
| 77 |  | +++ | 79 |  | +++ |
| 78 | 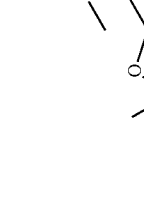 | ++ | 55 | 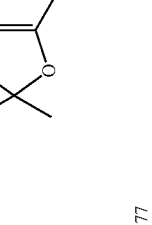 | +++ |

TABLE B-continued

| No. | Compound | Activity | No. | Compound | Activity |
|---|---|---|---|---|---|
| 56 | | +++ | | | + |
| 3 | | ‡‡‡ | | | |

1. Determination of $IC_{50}$ Values.

Reagents and Cells. $^{125}$I-labeled SDF-1 was purchased from Perkin-Elmer Life Sciences, Inc. (Boston, Mass.). The MCF-7 (adenocarcinoma; mammary gland) cell line was obtained from the American Type Culture Collection (Manassas, Va.) or and was cultured in DMEM (Mediatech, Herndon, Va.) supplemented with 10% fetal bovine serum (FBS) (Hy-Clone Logan, Utah) and bovine insulin (0.01 mg/mL) (Sigma, St. Louis, Mo.) at 37° C. in a humidified incubator at a 5% $CO_2$/air mixture. CCXCKR2 transfected MDA-MB-435S were produced as described below. MDA-MB-435S human breast cancer line, was purchased from ATCC, and cultured in DMEM/10% FBS medium. The complete coding sequence of the gene encoding CCXCKR2 (a.k.a.CXCR7, hRDC1), was isolated from MCF-7 cells using µMACs mRNA isolation kit (Miltenyi Biotec, Auburn, Calif.). DNA contamination was removed by DNase digestion via RNeasy columns (Qiagen, Inc., Valencia, Calif.) and cDNA was generated using GeneAmp RNA PCR Core Kit (Applied Biosystems, Foster City, Calif.). PCR of cDNA samples was performed using Taq PCR Master Mix kit (Qiagen, Inc.) and hRDC1 primers harboring 5' and 3' Not I sites (hRDC1F 5'-GAATGCGGCCGCTATGGATCTG-CATCTCTTCGACT-3' (SEQ ID NO:1), hRDC1R 5'-GAAT-GCGGCCGCTCATTTGGTGCTCTGCTCCAAG-3' (SEQ ID NO:2)) Not I digested PCR product was ligated into Not I digested pcDNA3.1(+)(Invitrogen, Carlsbad, Calif.) and screened for orientation and sequence confirmed. Plasmid DNA was then isolated from overnight bacterial cultures by Maxiprep (Qiagen, Inc.). Plasmid DNA (10 µg) was added to MDA-MB-435s cells and cells were electroporated (0.22 kV, 960 uF) via Gene Pulser (Biorad laboratories, Hercules, Calif.). 48 hr post-electroporation, cells were transferred to selection medium (1000 ug/ml G418).

Binding Analysis. Target compounds were tested to determine their ability to bind with CCXCKR2 sites on MCF-7 and/or MDA-MB-435S cells. Efficiency-maximized radioligand binding using filtration protocols as described in Dairaghi D J, et al., *HHV8-encoded vMIP-I selectively engages chemokine receptor CCR5. Agonist and antagonist profiles of viral chemokines.*, J. Biol. Chem. 1999 Jul. 30; 274(31): 21569-74 and Gosling J, et al., *Cutting edge: identification of a novel chemokine receptor that binds dendritic cell-and T cell-active chemokines including ELC, SLC, and TECK.*, J. Immunol. 2000 Mar. 15; 164(6):2851-6 was used.

In these assays, MCF-7 and/or MDA-MB-435S cells were interrogated with the target compounds and the ability of these compounds to displace $^{125}$I radiolabeled SDF-1 was assessed using the protocol described in Dairaghi and Gosling. The target compounds were added to the plate to the indicated concentration and were then incubated with cells followed by the addition of radiolabeled chemokine ($^{125}$I SDF-1) for 3 hr at 4° C. in the following binding medium (25 mM HEPES, 140 mM NaCl, 1 mM $CaCl_2$, 5 mM $MgCl_2$ and 0.2% bovine serum albumin, adjusted to pH 7.1). All assays were then incubated for 3 hrs at 4° C. with gentle agitation. Following incubation in all binding assays, reactions were aspirated onto PEI-treated GF/B glass filters (Packard) using a cell harvester (Packard) and washed twice (25 mM HEPES, 500 mM NaCl, 1 mM $CaCl_2$, 5 mM $MgCl_2$, adjusted to pH 7.1). Scintillant (MicroScint 10, Packard) was added to the wells, and the filters were counted in a Packard Topcount scintillation counter. Data were analyzed and plotted using Prism (GraphPad Prism version 3.0a for Macintosh, Graph-Pad Software, www.graphpad.com).

One of ordinary skill in the art will recognize from the provided description, figures, and examples, that modifications and changes can be made to the various embodiments of the invention without departing from the scope of the invention defined by the following claims and their equivalents.

What is claimed is:

1. A compound having the formula:

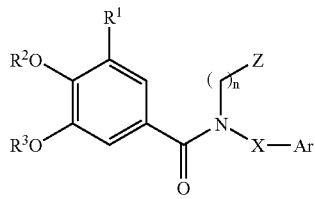

and all pharmaceutically acceptable salts thereof, wherein
the subscript n is an integer of from 1 to 3;
$R^1$ is a member selected from the group consisting of hydrogen, halogen, $C_{1-8}$ alkoxy, $C_{1-8}$ alkyl, $C_{1-8}$ haloalkyl, $C_{3-6}$ cycloalkyl, $C_{3-6}$ cycloalkoxy, $C_{3-6}$ cycloalkyl $C_{1-4}$ alkyl and $C_{3-6}$ cycloalkyl $C_{1-4}$ alkoxy;
$R^2$ and $R^3$ are each members independently selected from $C_{1-8}$ alkyl and $C_{1-8}$ haloalkyl, or are optionally combined with the oxygen atoms to which each is attached to form a five- to ten-membered ring optionally substituted with from one to four substituents selected from the group consisting of $C_{1-4}$ alkyl and $C_{1-4}$ haloalkyl;
X is a member selected from the group consisting of a bond, $CH_2$ and $—C(CH_3)—$;
Ar is a substituted or unsubstituted fused bicyclic aromatic ring system selected from the group consisting of naphthyl, quinolinyl, benzothienyl, isoquinolinyl, benzofuranyl, indolyl, benzothiazolyl, benzimidazolyl, 1,4-benzodioxan, quinoxalinyl, quinazolinyl, cinnolinyl and naphthyridinyl, or is a substituted or unsubstituted linked aromatic ring system selected from the group consisting of biphenyl, phenylthiazolyl, phenylpyrazolyl, pyridylthiazolyl and phenyl substituted with a 5- or 6-membered heteroaryl moiety selected from the group consisting of thiazolyl, thienyl, imidazolyl, pyrazolyl, furyl, oxazolyl, pyridyl, pyrimidinyl and pyrazinyl; and
Z is a pyrrolidine ring that is optionally substituted with from one to four $R^4$ substituents independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, $—COR^a$, $—CO_2R^a$, $—CONR^aR^b$, $NR^aCOR^b$, $—SO_2R^a$, $—X^1COR^a$, $—X^1CO_2R^a$, $—X^1CONR^aR^b$, $—X^1NR^aCOR^b$, $—X^1SO_2R^a$, $—X^1SO_2NR^aR^b$, $—X^1NR^aR^b$, $—X^1OR^a$ and $—X^1R^a$, wherein $X^1$ is a member selected from the group consisting of $C_{1-4}$ alkylene and $C_{2-4}$ alkenylene and each $R^a$ and $R^b$ is independently selected from the group consisting of hydrogen, $C_{1-8}$ alkyl, $C_{1-8}$ haloalkyl, $C_{3-6}$ cycloalkyl, $C_{3-9}$ heterocyclo-alkyl and aryl-$C_{1-4}$alkyl, and wherein the aliphatic portions of each of said $R^4$ substituents is optionally substituted with from one to three members selected from the group consisting of $—OH$, $—OR^m$, $—OC(O)NHR^m$, $—OC(O)N(R^m)_2$, $—SH$, $—SR^m$, $—S(O)R^m$, $—S(O)_2R^m$, $—SO_2NH_2$, $—S(O)_2NHR^m$, $—S(O)_2N(R^m)_2$, $—NHS(O)_2R^m$, $—NR^mS(O)_2R^m$, $—C(O)NH_2$, $—C(O)NHR^m$, $—C(O)N(R^m)_2$, $—C(O)R^m$, $—NHC(O)R^m$, $—NR^mC(O)R^m$, $—NHC(O)NH_2$, $—NR^mC(O)NH_2$, $—NR^mC(O)NHR^m$, $—NHC(O)NHR^m$, $—NR^mC(O)N(R^m)_2$, $—NHC(O)N(R^m)_2$, $—CO_2H$, $—CO_2R^m$, $—NHCO_2R^m$, $—NR^mCO_2R^m$, $—CN$, $—NO_2$, $—NH_2$, $—NHR^m$, $—N(R^m)_2$, $—NR^mS(O)NH_2$ and $—NR^mS(O)_2NHR^m$, wherein each $R^m$ is independently an unsubstituted $C_{1-6}$ alkyl; and optionally, two $R^4$ substituents on adjacent carbon atoms are combined to form a fused six-membered ring that is saturated.

2. A compound of claim 1, wherein Z is a member selected from the group consisting of

wherein the wavy line indicates the point of attachment to the remainder of the compound, and each of said Z groups is optionally substituted with from one to four $R^4$ substituents.

3. A compound of claim 1, wherein Z is

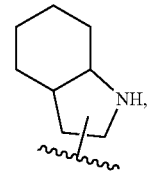

wherein the wavy line indicates the point of attachment to the remainder of the compound, and said Z group is optionally substituted with from one to two $R^4$ substituents.

4. A compound of claim 1, wherein Ar is a fused bicyclic aromatic ring system selected from the group consisting of naphthyl, quinolinyl, benzothienyl, isoquinolinyl, benzofuranyl, indolyl, benzothiazolyl, benzimidazolyl, 1,4-benzodioxan, quinoxalinyl, quinazolinyl, cinnolinyl and naphthyridinyl.

5. A compound of claim 1, wherein Ar is a linked-bicyclic aromatic ring system selected from the group consisting of biphenyl, phenylthiazolyl, phenylpyrazolyl, pyridylthiazolyl and phenyl substituted with a 5- or 6-membered heteroaryl group.

6. A compound of claim 5, wherein said 5- or 6-membered heteroaryl group is selected from the group consisting of pyrazolyl, thiazolyl, 1,2,3-triazolyl and pyridyl.

7. A compound of claim 1, wherein n is 1 or 2.

8. A compound of claim 1, wherein $R^1$ is selected from the group consisting of hydrogen and $C_{1-8}$ alkoxy.

9. A compound of claim 1, wherein $R^2$ and $R^3$ are each independently selected from the group consisting of methyl, ethyl, propyl, isopropyl, butyl, sec-butyl, isobutyl, tert-butyl and $C_{1-4}$ haloalkyl.

10. A compound of claim 1, wherein $R^2$ and $R^3$ are combined with the oxygen atoms to which each is attached to form a 5- or 6-membered ring optionally substituted with from one to four methyl groups.

11. A compound of claim 1, wherein n is 1 or 2; $R^1$ is selected from the group consisting of hydrogen and $C_{1-8}$ alkoxy; $R^2$ and $R^3$ are each independently selected from the group consisting of methyl, ethyl, propyl, isopropyl, butyl, sec-butyl, isobutyl, tert-butyl and $C_{1-4}$ haloalkyl; X is $CH_2$ or a bond; wherein when X is $CH_2$, Ar is a substituted or unsubstituted fused bicyclic aromatic ring system selected from the group consisting of naphthyl, quinolinyl, benzothienyl, isoquinolinyl, benzofuranyl, indolyl, benzothiazolyl, benzimidazolyl, 1,4-benzodioxan, quinoxalinyl, quinazolinyl, cinnolinyl and naphthyridinyl; and wherein when X is a bond, Ar is a substituted or unsubstituted linked-bicyclic aromatic ring system selected from the group consisting of biphenyl, phenylthiazolyl, phenylpyrazolyl, pyridylthiazolyl and phenyl substituted with a 5- or 6-membered heteroaryl group; Z is a member selected from the group consisting of

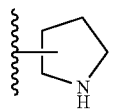 and 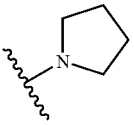

wherein the wavy line indicates the point of attachment to the remainder of the compound and each Z is optionally substituted with one or two $R^4$ substituents independently selected from the group consisting of $C_{1-8}$ alkyl, $C_{3-6}$ cycloalkyl, —$X^1OR^a$ and —$X^1R^a$, wherein $X^1$ is a member selected from the group consisting of $C_{1-4}$ alkylene and $C_{2-4}$ alkenylene and $R^a$ is selected from the group consisting of $C_{1-8}$ alkyl, $C_{3-6}$ cycloalkyl and $C_{3-9}$ heterocycloalkyl.

12. A compound of claim 1, wherein said compound is selected from the group consisting of:

- N—(S)-(1-Cyclohexylmethyl-pyrrolidine-2-ylmethyl)-3,4-dimethoxy-N-naphthalen-2-ylmethyl-benzamide;
- N—(S)-(1-Cyclohexylmethyl-pyrrolidin-2-ylmethyl)-3,4-dimethoxy-N-quinolin-3-ylmethyl-benzamide;
- N-benzofuran-2-ylmethyl-N—(S)-(1-cyclohexylmethyl-pyrrolidin-2-ylmethyl)-3,4-dimethoxy-benzamide;
- N-Benzofuran-2-ylmethyl-N—(S)-(1-cyclohexylmethyl-pyrrolidin-2-ylmethyl)-3,4,5-trimethoxy-benzamide;
- 3,4,5-Trimethoxy-N-[2-(1-methyl-pyrrolidin-2-yl)-ethyl]-N-naphthalen-2-ylmethyl-benzamide;
- 3,4,5-Trimethoxy-N-[2-(1-methyl-pyrrolidin-2-yl)-ethyl]-N-naphthalen-1-ylmethyl-benzamide;
- N-Benzofuran-2-ylmethyl-3,4,5-trimethoxy-N-[2-(1-methyl-pyrrolidin-2-yl)-ethyl]-benzamide;
- N-Benzo[b]thiophen-2-ylmethyl-3,4,5-trimethoxy-N-[2-(1-methyl-pyrrolidin-2-yl)-ethyl]-benzamide;
- N-(2,3-Dihydro-benzo[1,4]dioxin-6-ylmethyl)-3,4,5-trimethoxy-N-[2-(1-methyl-pyrrolidin-2-yl)-ethyl]-benzamide;
- 3,4,5-Trimethoxy-N-[2-(1-methyl-pyrrolidin-2yl)-N-quinolin-3-ylmethyl-benzamide;
- 3,4,5-Trimethoxy-N-[2-(1-methyl-pyrrolidin-2yl)-N-quinolin-2-ylmethyl-benzamide;
- N-Benzo[b]thiophen-3-ylmethyl-3,4,5-trimethoxy-N-[2-(1-methyl-pyrrolidin-2-yl)-ethyl]-benzamide;
- N-Benzothiazol-2-ylmethyl-3,4,5-trimethoxy-N-[2-(1-methyl-pyrrolidin-2-yl)-ethyl]-benzamide;
- 3,4,5-Trimethoxy-N-(1-methyl-1H-benzoimidazol-2-yl-methyl)-N-[2-(1-methyl-pyrrolidin-2-yl)-ethyl]-benzamide;
- N-(1H-Indol-2ylmethyl)-3,4,5-trimethoxy-N-[2-(1-methyl-pyrrolidin-2-yl)-ethyl]-benzamide;
- 3,4-Dimethoxy-(S)—N-pyrrolidin-2ylmethyl-N-(1-styryl-propenyl)-benzamide;
- N-Biphenyl-3-yl-(S)—N[1-(2-hydroxy-ethyl)-pyrrolidin-2ylmethyl]-3,4-dimethoxy-benzamide;
- N-Biphenyl-3-yl-(S)—N-(1-isopropyl-pyrrolidin-2-ylmethyl)-3,4-dimethoxy-benzamide;
- N-biphenyl-3-yl-(S)—N-(1-cyclohexylmethyl-pyrrolidin-2-ylmethyl)-3,4-dimethoxy-benzamide;
- N-Benzothiazol-2-ylmethyl-3,4 dimethoxy-N—(S)-pyrrolidin-2-ylmethyl-benzamide;
- N-Benzothiazol-2-ylmethyl-(S)—N-[1-(2-hydroxy-ethyl)-pyrrolidin-2-ylmethyl]-3,4-dimethoxy-benzamide;
- N-Benzothiazol-2-ylmethyl-(S)—N-(1-cyclohexylmethyl-pyrrolidin-2-ylmethyl)-3,4-dimethoxy-benzamide;
- N-Benzothiazol-2-ylmethyl-(S)—N-(1-isopropyl-pyrrolidin-2-ylmethyl)-3,4-dimethoxy-benzamide;
- N-Benzo[b]thiophene-2-ylmethyl-3,4-dimethoxy-N—(S)-pyrrolidin-2-ylmethyl-benzamide;
- N-Benzo[b]thiophen-2-ylmethyl-(S)—N-(1-cyclohexylmethyl-pyrrolidin-2-ylmethyl)-3,4-dimethoxy-benzamide;
- N-Biphenyl-3-yl-4-difluoromethoxy-3-methoxy-(S)—N-pyrrolidin-2-ylmethyl-benzamide;
- N-Biphenyl-3-yl-(S)—N-(1-cyclopropylmethyl-pyrrolidin-2-ylmethyl)-4-difluoromethoxy-3-methoxy-benzamide;
- N-biphenyl-3-yl-(S)—N-(1-cyclohexylmethyl-pyrrolidin-2-ylmethyl)-4-difluoromethoxy-3-methoxy-benzamide;
- N-(3'-Cyano-biphenyl-3-yl)-(S)—N-(1-cyclopropylmethyl-pyrrolidin-2-ylmethyl)-3,4-dimethoxy-benzamide;
- (S)—N-(1-Cyclopropylmethyl-pyrrolidin-2-ylmethyl)-3,4-dimethoxy-N-(3-pyridin-3-yl-phenyl)-benzamide;
- (S)-3'-[(1-Cyclopropylmethyl-pyrrolidin-2-ylmethyl)-(3,4-dimethoxy-benzoyl)-amino]-biphenyl-4-carboxylic acid ethyl ester;
- (S)—N-(1-Cyclopropylmethyl-pyrrolidin-2-ylmethyl)-N-(4'-dimethylamino-biphenyl-3-yl)-3,4-dimethoxy-benzamide;
- N-(3'-Chloro-4'-fluoro-biphenyl-3-yl)-(S)—N-(1-cyclopropylmethyl-pyrrolidin-2-ylmethyl)-3,4-dimethoxy-benzamide;
- 7-Methoxy-2,2-dimethyl-benzo[1,3]dioxole-5-carboxylic acid ((S)-1-azetidin-3-ylmethyl-pyrrolidin-2-ylmethyl)-isoquinolin-3-ylmethyl-amide;
- 7-Methoxy-2,2-dimethyl-benzo[1,3]dioxole-5-carboxylic acid [1-(3-aza-bicyclo[3.2.1]oct-8-ylmethyl)-(S)-1-pyrrolidin-2-ylmethyl]-isoquinolin-3-ylmethyl-amide;
- 7-Methoxy-2,2-dimethyl-benzo[1,3]dioxole-5-carboxylic acid [1-(3-aza-bicyclo[3.2.1]oct-8-ylmethyl)-pyrrolidin-2-ylmethyl]-[1,8]naphthyridin-2-ylmethyl-amide;
- 7-Methoxy-2,2-dimethyl-benzo[1,3]dioxole-5-carboxylic acid [1-(3-aza-bicyclo[3.2.1]oct-8-ylmethyl)-(S)-1-pyrrolidin-2-ylmethyl]-[1,8]naphthyridin-2-ylmethyl-amide;
- 7-Methoxy-2,2-dimethyl-benzo[1,3]dioxole-5-carboxylic acid [1,8]naphthyridin-2-ylmethyl-[(2S,3aS,7aS)-1-(octahydro-indol-2-yl)methyl]-amide;
- 7-Methoxy-2,2-dimethyl-benzo[1,3]dioxole-5-carboxylic acid ((S)-1-cyclobutyl-pyrrolidin-2-ylmethyl)-quinolin-2-ylmethyl-amide;
- 7-Methoxy-2,2-dimethyl-benzo[1,3]dioxole-5-carboxylic acid ((S)-1-azetidin-3-ylmethyl-pyrrolidin-2-ylmethyl)-quinolin-2-ylmethyl-amide;
- 7-Methoxy-2,2-dimethyl-benzo[1,3]dioxole-5-carboxylic acid [1-(3-aza-bicyclo[3.2.1]oct-8-ylmethyl)-(S)-1-pyrrolidin-2-ylmethyl]-quinolin-2-ylmethyl-amide;
- 7-Methoxy-2,2-dimethyl-benzo[1,3]dioxole-5-carboxylic acid [1-(3-aza-bicyclo[3.2.1]oct-8-ylmethyl)-(S)-1pyrrolidin-2-ylmethyl]-quinolin-2-ylmethyl-amide;
- 7-Methoxy-2,2-dimethyl-benzo[1,3]dioxole-5-carboxylic acid {(S)-1-[2-(2-methoxy-ethoxy)-ethyl]-pyrrolidin-2-ylmethyl}-quinolin-2-ylmethyl-amide;

7-Methoxy-2,2-dimethyl-benzo[1,3]dioxole-5-carboxylic acid ((S)-1-cyclobutyl-pyrrolidin-2-ylmethyl)-(4-phenyl-thiazol-2-ylmethyl)-amide;

7-Methoxy-2,2-dimethyl-benzo[1,3]dioxole-5-carboxylic acid (octahydro-indol-2-ylmethyl)-(4-phenyl-thiazol-2-ylmethyl)-amide;

7-Methoxy-2,2-dimethyl-benzo[1,3]dioxole-5-carboxylic acid ((S)-1-azetidin-3-ylmethyl-pyrrolidin-2-ylmethyl)-(4-phenyl-thiazol-2-ylmethyl)-amide;

7-Methoxy-2,2-dimethyl-benzo[1,3]dioxole-5-carboxylic acid [1-(3-aza-bicyclo[3.2.1]oct-8-ylmethyl)-pyrrolidin-2-ylmethyl]-benzo[b]thiophen-2-ylmethyl-amide;

7-Methoxy-2,2-dimethyl-benzo[1,3]dioxole-5-carboxylic acid [1-(3-aza-bicyclo[3.2.1]oct-8-ylmethyl)-(S)-1-pyrrolidin-2-ylmethyl]-benzo[b]thiophen-2-ylmethyl-amide;

7-Methoxy-2,2-dimethyl-benzo[1,3]dioxole-5-carboxylic acid (2-phenyl-thiazol-4-ylmethyl)-pyrrolidin-2-ylmethyl-amide;

7-Methoxy-2,2-dimethyl-benzo[1,3]dioxole-5-carboxylic acid ((S)-1-methyl-pyrrolidin-2-ylmethyl)-(2-phenyl-thiazol-4-ylmethyl)-amide;

7-Methoxy-2,2-dimethyl-benzo[1,3]dioxole-5-carboxylic acid benzofuran-2-ylmethyl-[(2S,3aS,7aS)-1-(octahydro-indol-2-yl)methyl]-amide;

7-Methoxy-2,2-dimethyl-benzo[1,3]dioxole-5-carboxylic acid benzofuran-2-ylmethyl-((S)-1-cyclobutyl-pyrrolidin-2-ylmethyl)-amide;

7-Methoxy-2,2-dimethyl-benzo[1,3]dioxole-5-carboxylic acid ((S)-1-cyclobutyl-pyrrolidin-2-ylmethyl)-naphthalen-2-ylmethyl-amide;

7-Methoxy-2,2-dimethyl-benzo[1,3]dioxole-5-carboxylic acid benzo[b]thiophen-2-ylmethyl-((S)-1-cyclobutyl-pyrrolidin-2-ylmethyl)-amide;

7-Methoxy-2,2-dimethyl-benzo[1,3]dioxole-5-carboxylic acid benzo[b]thiophen-2-ylmethyl-[(2S,3aS,7aS)-1-(octahydro-indol-2-yl)methyl]-amide;

7-Methoxy-2,2-dimethyl-benzo[1,3]dioxole-5-carboxylic acid ((S)-1-cyclobutyl-pyrrolidin-2-ylmethyl)-isoquinolin-3-ylmethyl-amide;

7-Methoxy-2,2-dimethyl-benzo[1,3]dioxole-5-carboxylic acid {(S)-1-[(1S,3S,5R)-1-(8-aza-bicyclo[3.2.1]oct-3-yl)methyl]-pyrrolidin-2-ylmethyl}-isoquinolin-3-ylmethyl-amide;

7-Methoxy-2,2-dimethyl-benzo[1,3]dioxole-5-carboxylic acid isoquinolin-3-ylmethyl-[(2S,3aS,7aS)-1-(octahydro-indol-2-yl)methyl]-amide;

7-Methoxy-2,2-dimethyl-benzo[1,3]dioxole-5-carboxylic acid [(2S,3aS,7aS)-1-(octahydro-indol-2-yl)methyl]-(2-oxy-isoquinolin-3-ylmethyl)-amide;

7-Methoxy-2,2-dimethyl-benzo[1,3]dioxole-5-carboxylic acid (1-isoquinolin-3-yl-ethyl)-[(2S,3aS,7aS)-1-(octahydro-indol-2-yl)methyl]-amide;

7-Methoxy-2,2-dimethyl-benzo[1,3]dioxole-5-carboxylic acid ((S)-1-cyclobutyl-pyrrolidin-2-ylmethyl)-quinoxalin-2-ylmethyl-amide;

7-Methoxy-2,2-dimethyl-benzo[1,3]dioxole-5-carboxylic acid [(2S,3aS,7aS)-1-(octahydro-indol-2-yl)methyl]-quinoxalin-2-ylmethyl-amide;

7-Methoxy-2,2-dimethyl-benzo[1,3]dioxole-5-carboxylic acid ((S)-1-cyclobutyl-pyrrolidin-2-ylmethyl)-(1-oxy-quinolin-2-ylmethyl)-amide;

7-Methoxy-2,2-dimethyl-benzo[1,3]dioxole-5-carboxylic acid [(2S,3aS,7aS)-1-(octahydro-indol-2-yl)methyl]-quinolin-2-ylmethyl-amide;

7-Methoxy-2,2-dimethyl-benzo[1,3]dioxole-5-carboxylic acid [(2S,3aS,7aS)-1-(octahydro-indol-2-yl)methyl]-(1-quinolin-2-yl-ethyl)-amide;

7-Methoxy-2,2-dimethyl-benzo[1,3]dioxole-5-carboxylic acid (6-fluoro-quinolin-2-ylmethyl)-[(2S,3aS,7aS)-1-(octahydro-indol-2-yl)methyl]-amide;

7-Methoxy-2,2-dimethyl-benzo[1,3]dioxole-5-carboxylic acid (6-chloro-quinolin-2-ylmethyl)-[(2S,3aS,7aS)-1-(octahydro-indol-2-yl)methyl]-amide;

7-Methoxy-2,2-dimethyl-benzo[1,3]dioxole-5-carboxylic acid cinnolin-3-ylmethyl-((S)-1-cyclobutyl-pyrrolidin-2-ylmethyl)-amide;

N-((S)-1-Cyclohexylmethyl-pyrrolidin-2-ylmethyl)-3,4-dimethoxy-N-(3-pyrazol-1-yl-phenyl)-benzamide;

N-((S)-1-Cyclohexylmethyl-pyrrolidin-2-ylmethyl)-3,4-dimethoxy-N-(3-[1,2,3]triazol-1-yl-phenyl)-benzamide;

7-Methoxy-2,2-dimethyl-benzo[1,3]dioxole-5-carboxylic acid [(2S,3aS,7aS)-1-(octahydro-indol-2-yl)methyl]-(4-phenyl-5-trifluoromethyl-thiazol-2-ylmethyl)-amide;

7-Methoxy-2,2-dimethyl-benzo[1,3]dioxole-5-carboxylic acid ((S)-1-cyclobutyl-pyrrolidin-2-ylmethyl)-(1-phenyl-1H-pyrazol-3-ylmethyl)-amide; and 7-Methoxy-2,2-dimethyl-benzo[1,3]dioxole-5-carboxylic acid (5-chloro-2-phenyl-thiazol-4-ylmethyl)-[(2S,3aS,7aS)-1-(octahydro-indol-2-yl)methyl]-amide.

13. A pharmaceutical composition comprising a compound having the formula:

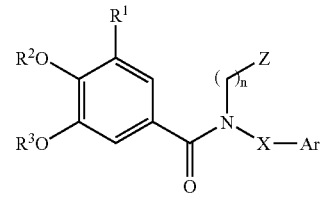

and all pharmaceutically acceptable salts thereof, wherein
the subscript n is an integer of from 1 to 3;
$R^1$ is a member selected from the group consisting of hydrogen, halogen, $C_{1-8}$ alkoxy, $C_{1-8}$ alkyl, $C_{1-8}$ haloalkyl, $C_{3-6}$ cycloalkyl, $C_{3-6}$ cycloalkoxy, $C_{3-6}$ cycloalkyl $C_{1-4}$ alkyl and $C_{3-6}$ cycloalkyl $C_{1-4}$ alkoxy;
$R^2$ and $R^3$ are each members independently selected from $C_{1-8}$ alkyl and $C_{1-8}$ haloalkyl, or are optionally combined with the oxygen atoms to which each is attached to form a five- to ten-membered ring optionally substituted with from one to four substituents selected from the group consisting of $C_{1-4}$ alkyl and $C_{1-4}$ haloalkyl;
X is a member selected from the group consisting of a bond, $CH_2$ and —$CH(CH_3)$—;
Ar is a substituted or unsubstituted fused bicyclic aromatic ring system selected from the group consisting of naphthyl, quinolinyl, benzothienyl, isoquinolinyl, benzofuranyl, indolyl, benzothiazolyl, benzimidazolyl, 1,4-benzodioxan, quinoxalinyl, quinazolinyl, cinnolinyl and naphthyridinyl, or is a substituted or unsubstituted linked aromatic ring system selected from the group consisting of biphenyl, phenylthiazolyl, phenylpyrazolyl, pyridylthiazolyl and phenyl substituted with a 5- or 6-membered heteroaryl moiety selected from the group consisting of thiazolyl, thienyl, imidazolyl, pyrazolyl, furyl, oxazolyl, pyridyl, pyrimidinyl and pyrazinyl; and Z is a pyrrolidine ring that is optionally substituted with from one to four $R^4$ substituents independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, —$COR^a$, —$CO_2R^a$, —$CONR^aR^b$, —$NR^aCOR^b$, —$SO_2R^a$, —$X^1COR^a$, —$X^1CO_2R^a$, —$X^1CONR^aR^b$, —$X^1NR^aCOR^b$, —$X^1SO_2R^a$, —$X^1SO_2NR^aR^b$, —$X^1NR^aR^b$, —$X^1OR^a$ and —$X^1R^a$, wherein $X^1$ is a member selected from the group consisting of $C_{1-4}$ alkylene and $C_{2-4}$ alkenylene and each $R^a$ and $R^b$ is independently selected from the group consisting of hydrogen, $C_{1-8}$ alkyl, $C_{1-8}$ haloalkyl, $C_{3-6}$ cycloalkyl, $C_{3-9}$ heterocyclo-alkyl and aryl-$C_{1-4}$alkyl, and wherein the aliphatic portions of each of said $R^4$ substituents is optionally substituted with from one to three members selected from the group consisting of —OH, —$OR^m$, —OC(O)$NHR^m$, —OC(O)N($R^m$)$_2$, —SH, —$SR^m$, —S(O)$R^m$, —S(O)$_2R^m$, —$SO_2NH_2$, —S(O)$_2NHR^m$, —S(O)$_2N$($R^m$)$_2$, —NHS(O)$_2R^m$, —$NR^mS(O)_2R^m$, —C(O)$NH_2$, —C(O)$NHR^m$, —C(O)N($R^m$)$_2$, —C(O)$R^m$, —NHC(O)$R^m$, —$NR^mC(O)R^m$, —NHC(O)$NH_2$, —$NR^mC(O)NH_2$, —$NR^mC(O)NHR^m$, —NHC(O)$NHR^m$, —$NR^mC(O)N(R^m)_2$, —NHC(O)N($R^m$)$_2$, —$CO_2H$, —$CO_2R^m$, —$NHCO_2R^m$, —$NR^mCO_2R^m$, —CN, —$NO_2$, —$NH_2$, —$NHR^m$, —N($R^m$)$_2$, —$NR^mS(O)NH_2$ and —$NR^mS(O)_2NHR^m$, wherein each $R^m$ is independently an unsubstituted $C_{1-6}$ alkyl; and optionally, two $R^4$ substituents on adjacent carbon atoms are combined to form a fused six-membered ring that is saturated; and a pharmaceutically acceptable excipient.

14. A pharmaceutical composition of claim 13, wherein-n is 1 or 2; $R^1$ is selected from the group consisting of hydrogen and $C_{1-8}$ alkoxy; $R^2$ and $R^3$ are each independently selected from the group consisting of methyl, ethyl, propyl, isopropyl, butyl, sec-butyl, isobutyl, tert-butyl and $C_{1-4}$ haloalkyl; X is $CH_2$ or a bond; wherein when X is $CH_2$, Ar is a substituted or unsubstituted fused bicyclic aromatic ring system selected from the group consisting of naphthyl, quinolinyl, benzothienyl, isoquinolinyl, benzofuranyl, indolyl, benzothiazolyl, benzimidazolyl, 1,4-benzodioxan, quinoxalinyl and naphthyridinyl; and wherein when X is a bond, Ar is a substituted or unsubstituted linked-bicyclic aromatic ring system selected from the group consisting of biphenyl, phenylthiazolyl, phenylpyrazolyl, pyridylthiazolyl and phenyl substituted with a 5- or 6-membered heteroaryl group; Z is a member selected from the group consisting of

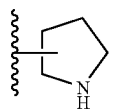 and 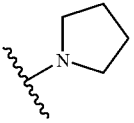

wherein the wavy line indicates the point of attachment to the remainder of the compound and each Z is optionally substituted with one or two $R^4$ substituents independently selected from the group consisting of $C_{1-8}$ alkyl, $C_{3-6}$ cycloalkyl, —$X^1OR^a$ and —$X^1R^a$, wherein $X^1$ is a member selected from the group consisting of $C_{1-4}$ alkylene and $C_{2-4}$ alkenylene and $R^a$ is selected from the group consisting of $C_{1-8}$ alkyl, $C_{3-6}$ cycloalkyl and $C_{3-9}$ heterocycloalkyl.

15. A pharmaceutical composition of claim 13, wherein said compound is selected from the group consisting of:

N—(S)-(1-Cyclohexylmethyl-pyrrolidine-2-ylmethyl)-3,4-dimethoxy-N-naphthalen-2-ylmethyl-benzamide;
N—(S)-(1-Cyclohexylmethyl-pyrrolidin-2-ylmethyl)-3,4-dimethoxy-N-quinolin-3-ylmethyl-benzamide;
N-benzofuran-2-ylmethyl-N—(S)-(1-cyclohexylmethyl-pyrrolidin-2-ylmethyl)-3,4-dimethoxy-benzamide;
N-Benzofuran-2-ylmethyl-N—(S)-(1-cyclohexylmethyl-pyrrolidin-2-ylmethyl)-3,4,5-trimethoxy-benzamide;
3,4,5-Trimethoxy-N-[2-(1-methyl-pyrrolidin-2-yl)-ethyl]-N-naphthalen-2-ylmethyl-benzamide;
3,4,5-Trimethoxy-N-[2-(1-methyl-pyrrolidin-2-yl)-ethyl]-N-naphthalen-1-ylmethyl-benzamide;
N-Benzofuran-2-ylmethyl-3,4,5-trimethoxy-N-[2-(1-methyl-pyrrolidin-2-yl)-ethyl]-benzamide;
N-Benzo[b]thiophen-2-ylmethyl-3,4,5-trimethoxy-N-[2-(1-methyl-pyrrolidin-2-yl)-ethyl]-benzamide;
N-(2,3-Dihydro-benzo[1,4]dioxin-6-ylmethyl)-3,4,5-trimethoxy-N-[2-(1-methyl-pyrrolidin-2-yl)-ethyl]-benzamide;
3,4,5-Trimethoxy-N-[2-(1-methyl-pyrrolidin-2yl)-N-quinolin-3-ylmethyl-benzamide;
3,4,5-Trimethoxy-N-[2-(1-methyl-pyrrolidin-2yl)-N-quinolin-2-ylmethyl-benzamide;
N-Benzo[b]thiophen-3-ylmethyl-3,4,5-trimethoxy-N-[2-(1-methyl-pyrrolidin-2-yl)-ethyl]-benzamide;
N-Benzothiazol-2-ylmethyl-3,4,5-trimethoxy-N-[2-(1-methyl-pyrrolidin-2-yl)-ethyl]-benzamide;
3,4,5-Trimethoxy-N-(1-methyl-1H-benzoimidazol-2-ylmethyl)-N-[2-(1-methyl-pyrrolidin-2-yl)-ethyl]-benzamide;
N-(1H-Indol-2ylmethyl)-3,4,5-trimethoxy-N-[2-(1-methyl-pyrrolidin-2-yl)-ethyl]-benzamide;
3,4-Dimethoxy-(S)—N-pyrrolidin-2ylmethyl-N-(1-styryl-propenyl)-benzamide;
N-Biphenyl-3-yl-(S)—N[1-(2-hydroxy-ethyl)-pyrrolidin-2ylmethyl]-3,4-dimethoxy-benzamide;
N-Biphenyl-3-yl-(S)—N-(1-isopropyl-pyrrolidin-2-ylmethyl)-3,4-dimethoxy-benzamide;
N-biphenyl-3-yl-(S)—N-(1-cyclohexylmethyl-pyrrolidin-2-ylmethyl)-3,4-dimethoxy-benzamide;
N-Benzothiazol-2-ylmethyl-3,4 dimethoxy-N—(S)-pyrrolidin-2-ylmethyl-benzamide;
N-Benzothiazol-2-ylmethyl-(S)—N-[1-(2-hydroxy-ethyl)-pyrrolidin-2-ylmethyl]-3,4-dimethoxy-benzamide;
N-Benzothiazol-2-ylmethyl-(S)—N-(1-cyclohexylmethyl-pyrrolidin-2-ylmethyl)-3,4-dimethoxy-benzamide;
N-Benzothiazol-2-ylmethyl-(S)—N-(1-isopropyl-pyrrolidin-2-ylmethyl)-3,4-dimethoxy-benzamide;
N-Benzo[b]thiophene-2-ylmethyl-3,4-dimethoxy-N—(S)-pyrrolidin-2-ylmethyl-benzamide;
N-Benzo[b]thiophen-2-ylmethyl-(S)—N-(1-cyclohexylmethyl-pyrrolidin-2-ylmethyl)-3,4-dimethoxy-benzamide;
N-Biphenyl-3-yl-4-difluoromethoxy-3-methoxy-(S)—N-pyrrolidin-2-ylmethyl-benzamide;
N-Biphenyl-3-yl-(S)—N-(1-cyclopropylmethyl-pyrrolidin-2-ylmethyl)-4-difluoromethoxy-3-methoxy-benzamide;
N-biphenyl-3-yl-(S)—N-(1-cyclohexylmethyl-pyrrolidin-2-ylmethyl)-4-difluoromethoxy-3-methoxy-benzamide;
N-(3'-Cyano-biphenyl-3-yl)-(S)—N-(1-cyclopropylmethyl-pyrrolidin-2-ylmethyl)-3,4-dimethoxy-benzamide;

(S)—N-(1-Cyclopropylmethyl-pyrrolidin-2-ylmethyl)-3,4-dimethoxy-N-(3-pyridin-3-yl-phenyl)-benzamide;

(S)-3'-[(1-Cyclopropylmethyl-pyrrolidin-2-ylmethyl)-(3,4-dimethoxy-benzoyl)-amino]-biphenyl-4-carboxylic acid ethyl ester;

(S)—N-(1-Cyclopropylmethyl-pyrrolidin-2-ylmethyl)-N-(4'-dimethylamino-biphenyl-3-yl)-3,4-dimethoxy-benzamide;

N-(3'-Chloro-4'-fluoro-biphenyl-3-yl)-(S)—N-(1-cyclopropylmethyl-pyrrolidin-2-ylmethyl)-3,4-dimethoxy-benzamide;

7-Methoxy-2,2-dimethyl-benzo[1,3]dioxole-5-carboxylic acid ((S)-1-azetidin-3-ylmethyl-pyrrolidin-2-ylmethyl)-isoquinolin-3-ylmethyl-amide;

7-Methoxy-2,2-dimethyl-benzo[1,3]dioxole-5-carboxylic acid [1-(3-aza-bicyclo[3.2.1]oct-8-ylmethyl)-(S)-1-pyrrolidin-2-ylmethyl]-isoquinolin-3-ylmethyl-amide;

7-Methoxy-2,2-dimethyl-benzo[1,3]dioxole-5-carboxylic acid [1-(3-aza-bicyclo[3.2.1]oct-8-ylmethyl)-pyrrolidin-2-ylmethyl]-[1,8]naphthyridin-2-ylmethyl-amide;

7-Methoxy-2,2-dimethyl-benzo[1,3]dioxole-5-carboxylic acid [1-(3-aza-bicyclo[3.2.1]oct-8-ylmethyl)-(S)-1-pyrrolidin-2-ylmethyl]-[1,8]naphthyridin-2-ylmethyl-amide;

7-Methoxy-2,2-dimethyl-benzo[1,3]dioxole-5-carboxylic acid [1,8]naphthyridin-2-ylmethyl-[(2S,3aS,7aS)-1-(octahydro-indol-2-yl)methyl]-amide;

7-Methoxy-2,2-dimethyl-benzo[1,3]dioxole-5-carboxylic acid ((S)-1-cyclobutyl-pyrrolidin-2-ylmethyl)-quinolin-2-ylmethyl-amide;

7-Methoxy-2,2-dimethyl-benzo[1,3]dioxole-5-carboxylic acid ((S)-1-azetidin-3-ylmethyl-pyrrolidin-2-ylmethyl)-quinolin-2-ylmethyl-amide;

7-Methoxy-2,2-dimethyl-benzo[1,3]dioxole-5-carboxylic acid [1-(3-aza-bicyclo[3.2.1]oct-8-ylmethyl)-(S)-1-pyrrolidin-2-ylmethyl]-quinolin-2-ylmethyl-amide;

7-Methoxy-2,2-dimethyl-benzo[1,3]dioxole-5-carboxylic acid [1-(3-aza-bicyclo[3.2.1]oct-8-ylmethyl)-(S)-1pyrrolidin-2-ylmethyl]-quinolin-2-ylmethyl-amide;

7-Methoxy-2,2-dimethyl-benzo[1,3]dioxole-5-carboxylic acid {(S)-1-[2-(2-methoxy-ethoxy)-ethyl]-pyrrolidin-2-ylmethyl}-quinolin-2-ylmethyl-amide;

7-Methoxy-2,2-dimethyl-benzo[1,3]dioxole-5-carboxylic acid ((S)-1-cyclobutyl-pyrrolidin-2-ylmethyl)-(4-phenyl-thiazol-2-ylmethyl)-amide;

7-Methoxy-2,2-dimethyl-benzo[1,3]dioxole-5-carboxylic acid (octahydro-indol-2-ylmethyl)-(4-phenyl-thiazol-2-ylmethyl)-amide;

7-Methoxy-2,2-dimethyl-benzo[1,3]dioxole-5-carboxylic acid ((S)-1-azetidin-3-ylmethyl-pyrrolidin-2-ylmethyl)-(4-phenyl-thiazol-2-ylmethyl)-amide;

7-Methoxy-2,2-dimethyl-benzo[1,3]dioxole-5-carboxylic acid [1-(3-aza-bicyclo[3.2.1]oct-8-ylmethyl)-pyrrolidin-2-ylmethyl]-benzo[b]thiophen-2-ylmethyl-amide;

7-Methoxy-2,2-dimethyl-benzo[1,3]dioxole-5-carboxylic acid [1-(3-aza-bicyclo[3.2.1]oct-8-ylmethyl)-(S)-1-pyrrolidin-2-ylmethyl]-benzo[b]thiophen-2-ylmethyl-amide;

7-Methoxy-2,2-dimethyl-benzo[1,3]dioxole-5-carboxylic acid (2-phenyl-thiazol-4-ylmethyl)-pyrrolidin-2-ylmethyl-amide;

7-Methoxy-2,2-dimethyl-benzo[1,3]dioxole-5-carboxylic acid ((S)-1-methyl-pyrrolidin-2-ylmethyl)-(2-phenyl-thiazol-4-ylmethyl)-amide;

7-Methoxy-2,2-dimethyl-benzo[1,3]dioxole-5-carboxylic acid benzofuran-2-ylmethyl-[(2S,3aS,7aS)-1-(octahydro-indol-2-yl)methyl]-amide;

7-Methoxy-2,2-dimethyl-benzo[1,3]dioxole-5-carboxylic acid benzofuran-2-ylmethyl-((S)-1-cyclobutyl-pyrrolidin-2-ylmethyl)-amide;

7-Methoxy-2,2-dimethyl-benzo[1,3]dioxole-5-carboxylic acid ((S)-1-cyclobutyl-pyrrolidin-2-ylmethyl)-naphthalen-2-ylmethyl-amide;

7-Methoxy-2,2-dimethyl-benzo[1,3]dioxole-5-carboxylic acid benzo[b]thiophen-2-ylmethyl-((S)-1-cyclobutyl-pyrrolidin-2-ylmethyl)-amide;

7-Methoxy-2,2-dimethyl-benzo[1,3]dioxole-5-carboxylic acid benzo[b]thiophen-2-ylmethyl-[(2S,3aS,7aS)-1-(octahydro-indol-2-yl)methyl]-amide;

7-Methoxy-2,2-dimethyl-benzo[1,3]dioxole-5-carboxylic acid ((S)-1-cyclobutyl-pyrrolidin-2-ylmethyl)-isoquinolin-3-ylmethyl-amide;

7-Methoxy-2,2-dimethyl-benzo[1,3]dioxole-5-carboxylic acid {(S)-1-[(1S,3S,5R)-1-(8-aza-bicyclo[3.2.1]oct-3-yl)methyl]-pyrrolidin-2-ylmethyl}-isoquinolin-3-ylmethyl-amide;

7-Methoxy-2,2-dimethyl-benzo[1,3]dioxole-5-carboxylic acid isoquinolin-3-ylmethyl-[(2S,3aS,7aS)-1-(octahydro-indol-2-yl)methyl]-amide;

7-Methoxy-2,2-dimethyl-benzo[1,3]dioxole-5-carboxylic acid [(2S,3aS,7aS)-1-(octahydro-indol-2-yl)methyl]-(2-oxy-isoquinolin-3-ylmethyl)-amide;

7-Methoxy-2,2-dimethyl-benzo[1,3]dioxole-5-carboxylic acid (1-isoquinolin-3-yl-ethyl)-[(2S,3aS,7aS)-1-(octahydro-indol-2-yl)methyl]-amide;

7-Methoxy-2,2-dimethyl-benzo[1,3]dioxole-5-carboxylic acid ((S)-1-cyclobutyl-pyrrolidin-2-ylmethyl)-quinoxalin-2-ylmethyl-amide;

7-Methoxy-2,2-dimethyl-benzo[1,3]dioxole-5-carboxylic acid [(2S,3aS,7aS)-1-(octahydro-indol-2-yl)methyl]-quinoxalin-2-ylmethyl-amide;

7-Methoxy-2,2-dimethyl-benzo[1,3]dioxole-5-carboxylic acid ((S)-1-cyclobutyl-pyrrolidin-2-ylmethyl)-(1-oxy-quinolin-2-ylmethyl)-amide;

7-Methoxy-2,2-dimethyl-benzo[1,3]dioxole-5-carboxylic acid [(2S,3aS,7aS)-1-(octahydro-indol-2-yl)methyl]-quinolin-2-ylmethyl-amide;

7-Methoxy-2,2-dimethyl-benzo[1,3]dioxole-5-carboxylic acid [(2S,3aS,7aS)-1-(octahydro-indol-2-yl)methyl]-(1-quinolin-2-yl-ethyl)-amide;

7-Methoxy-2,2-dimethyl-benzo[1,3]dioxole-5-carboxylic acid (6-fluoro-quinolin-2-ylmethyl)-[(2S,3aS,7aS)-1-(octahydro-indol-2-yl)methyl]-amide;

7-Methoxy-2,2-dimethyl-benzo[1,3]dioxole-5-carboxylic acid (6-chloro-quinolin-2-ylmethyl)-[(2S,3aS,7aS)-1-(octahydro-indol-2-yl)methyl]-amide;

7-Methoxy-2,2-dimethyl-benzo[1,3]dioxole-5-carboxylic acid cinnolin-3-ylmethyl-((S)-1-cyclobutyl-pyrrolidin-2-ylmethyl)-amide;

N-((S)-1-Cyclohexylmethyl-pyrrolidin-2-ylmethyl)-3,4-dimethoxy-N-(3-pyrazol-1-yl-phenyl)-benzamide;

N-((S)-1-Cyclohexylmethyl-pyrrolidin-2-ylmethyl)-3,4-dimethoxy-N-(3-[1,2,3]triazol-1-yl-phenyl)-benzamide;

7-Methoxy-2,2-dimethyl-benzo[1,3]dioxole-5-carboxylic acid [(2S,3aS,7aS)-1-(octahydro-indol-2-yl)methyl]-(4-phenyl-5-trifluoromethyl-thiazol-2-ylmethyl)-amide;

7-Methoxy-2,2-dimethyl-benzo[1,3]dioxole-5-carboxylic acid ((S)-1-cyclobutyl-pyrrolidin-2-ylmethyl)-(1-phenyl-1H-pyrazol-3-ylmethyl)-amide; and 7-Methoxy-2,2-dimethyl-benzo[1,3]dioxole-5-carboxylic acid (5-chloro-2-phenyl-thiazol-4-ylmethyl)-[(2S,3aS,7aS)-1-(octahydro-indol-2-yl)methyl]-amide.

\* \* \* \* \*

UNITED STATES PATENT AND TRADEMARK OFFICE
CERTIFICATE OF CORRECTION

PATENT NO. : 7,417,062 B2  Page 1 of 1
APPLICATION NO. : 11/202961
DATED : August 26, 2008
INVENTOR(S) : Anita Melikian et al.

It is certified that error appears in the above-identified patent and that said Letters Patent is hereby corrected as shown below:

In the Claims:

Claim 1, Column 139, Line 26: please insert H between C and (in "-C(CH$_3$)-"

Claim 1, Column 139, Line 45: please insert - in front of "NR$^a$COR$^b$,"

Signed and Sealed this

Eleventh Day of November, 2008

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence:hRDC1
      (CCXCKR2 G-protein coupled receptor (GPCR)) cDNA PCR primer
      hRDC1F

<400> SEQUENCE: 1
gaatgcggcc gctatggatc tgcatctctt cgact                             35

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence:hRDC1
      (CCXCKR2 G-protein coupled receptor (GPCR)) cDNA PCR primer
      hRDC1R

<400> SEQUENCE: 2
gaatgcggcc gctcatttgg tgctctgctc caag                              34
```